United States Patent
Wada

(10) Patent No.: US 9,051,403 B2
(45) Date of Patent: Jun. 9, 2015

(54) PHOTOSENSITIVE COMPOSITION, PATTERN FORMING METHOD USING THE PHOTOSENSITIVE COMPOSITION AND COMPOUND FOR USE IN THE PHOTOSENSITIVE COMPOSITION

(75) Inventor: Kenji Wada, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 891 days.

(21) Appl. No.: 12/679,140

(22) PCT Filed: Sep. 18, 2008

(86) PCT No.: PCT/JP2008/066887
§ 371 (c)(1),
(2), (4) Date: Mar. 19, 2010

(87) PCT Pub. No.: WO2009/038148
PCT Pub. Date: Mar. 26, 2009

(65) Prior Publication Data
US 2010/0233617 A1    Sep. 16, 2010

(30) Foreign Application Priority Data

Sep. 21, 2007 (JP) ................................. 2007-245332
Jan. 18, 2008 (JP) ................................. 2008-009840

(51) Int. Cl.
| | | |
|---|---|---|
| G03F 7/004 | (2006.01) | |
| G03F 7/028 | (2006.01) | |
| C08F 20/10 | (2006.01) | |
| C08F 214/18 | (2006.01) | |
| C08F 220/34 | (2006.01) | |
| C08F 220/26 | (2006.01) | |
| C08F 220/38 | (2006.01) | |
| C07D 211/96 | (2006.01) | |
| C07D 243/04 | (2006.01) | |
| C07D 295/26 | (2006.01) | |
| G03F 7/039 | (2006.01) | |
| G03F 7/20 | (2006.01) | |

(52) U.S. Cl.
CPC ............ *C08F 20/10* (2013.01); *C08F 214/18* (2013.01); *C08F 220/34* (2013.01); *C08F 220/26* (2013.01); *C08F 220/38* (2013.01); *C07D 211/96* (2013.01); *C07D 243/04* (2013.01); *C07D 295/26* (2013.01); *G03F 7/0045* (2013.01); *G03F 7/0046* (2013.01); *G03F 7/0397* (2013.01); *G03F 7/2022* (2013.01); *G03F 7/2041* (2013.01)

(58) Field of Classification Search
CPC .... C08F 214/18; C08F 220/26; C08F 220/34; C08F 220/38; G03F 7/004
USPC .................. 430/270.1; 528/173; 564/192.85; 526/243, 242, 248, 318; 558/51
See application file for complete search history.

(56) References Cited

U.S. PATENT DOCUMENTS

| | | | |
|---|---|---|---|
| 4,480,910 A | 11/1984 | Takanashi et al. | |
| 5,696,224 A * | 12/1997 | Benrabah et al. | ............. 528/491 |
| 2005/0014090 A1 | 1/2005 | Hirayama et al. | |
| 2006/0154171 A1 | 7/2006 | Hirayama et al. | |
| 2006/0166135 A1 * | 7/2006 | Wada | ......................... 430/270.1 |
| 2007/0082289 A1 | 4/2007 | Wada | |
| 2007/0141512 A1 * | 6/2007 | Wada et al. | ................. 430/270.1 |
| 2007/0149702 A1 * | 6/2007 | Ando et al. | .................... 524/556 |
| 2007/0178394 A1 | 8/2007 | Hirayama et al. | |
| 2008/0102407 A1 * | 5/2008 | Ohsawa et al. | ............ 430/286.1 |
| 2009/0130605 A1 | 5/2009 | Hirayama et al. | |

FOREIGN PATENT DOCUMENTS

| | | | |
|---|---|---|---|
| EP | 1 897 869 A1 | 3/2008 | |
| JP | 57-153433 A | 9/1982 | |
| JP | 7-220990 A | 8/1995 | |
| JP | 2002-075857 A | 3/2002 | |
| JP | 2006178317 A * | 7/2006 | |
| JP | 2006-215526 A | 8/2006 | |
| JP | 2006-234938 A | 9/2006 | |
| JP | 2006-301145 A | 11/2006 | |
| JP | 2006-330099 A | 12/2006 | |
| JP | 2007-003619 A | 1/2007 | |
| JP | 2007-163606 A | 6/2007 | |
| JP | 2007-187887 A | 7/2007 | |
| JP | 2007-197718 A | 8/2007 | |

(Continued)

OTHER PUBLICATIONS

Machine translation of KR 10-2007-0069068, published on Jul. 2, 2007.*
Extended European Search Report dated Mar. 24, 2011 in EP Application No. 08832644.2.
Communication dated Feb. 6, 2012, issued by the European Patent Office in corresponding European Patent Application No. 11184820.6.
Wang, Mingxing et al. "Novel Anionic Photoacid Generators (PAGs) and Corresponding PAG Bound Polymers", Macromolecular Rapid Communications, 27, p. 1590-1595, 2006.

(Continued)

*Primary Examiner* — Anca Eoff
(74) *Attorney, Agent, or Firm* — Sughrue Mion, PLLC

(57) ABSTRACT

A photosensitive composition includes: (A) a resin containing a repeating unit corresponding to a compound represented by the following formula (I); the resin being capable of producing an acid group upon irradiation with an actinic ray or radiation:

Z-A-X-B-R    (I)

wherein Z represents a group capable of becoming an acid group resulting from leaving of a cation upon irradiation with an actinic ray or radiation; A represents an alkylene group; X represents a single bond or a heteroatom-containing divalent linking group; B represents a single bond, an oxygen atom or —N(Rx)-; Rx represents a hydrogen atom or a monovalent organic group; R represents a monovalent organic group substituted by Y; when B represents —N(Rx)-, R and Rx may combine with each other to form a ring; and Y represents a polymerizable group.

13 Claims, 1 Drawing Sheet

(56) References Cited

FOREIGN PATENT DOCUMENTS

| JP | 2007-219471 A | | 8/2007 |
|----|---------------|---|--------|
| JP | 2008-133448 A | | 6/2008 |
| KR | 10-2007-0069 | * | 7/2007 |
| WO | 2004/068242 A1 | | 8/2004 |
| WO | 2004/077158 A1 | | 9/2004 |
| WO | 2006/121096 A1 | | 11/2006 |
| WO | 2008/056796 A1 | | 5/2008 |

OTHER PUBLICATIONS

Lin, B.J. "Semiconductor Foundry, Lithography, and Partners", Proceedings of SPIE vol. 4688, 2002, , p. 11-24.
International Search Report [PCT/Isa/210] for PCT/JP2008/066887, dated Oct. 28, 2008.
International Preliminary Examination Report [PCT/Isa/237] for PCT/JP2008/066887, dated Oct. 28, 2008.
Office Action issued Jul. 2, 2013, by the Taiwan Intellectual Property Office in counterpart Taiwanese Application No. 097135984.
Office Action dated Apr. 2, 2013 from the Japanese Patent Office, in counterpart Japanese Application No. 2008-009840.
Office Action issued on Jun. 25, 2013 in corresponding Japanese Application No. 2008-009840.
Decision on Examination, dated Mar. 28, 2014, issued by the Taiwanese Patent Office in counterpart Taiwanese Application No. 097135984.
Office Action dated Oct. 28, 2014 issued by the Japanese Patent Office, in counterpart Japanese Patent Application No. 2013/198915.
Office Action from the Korean Intellectual Property Office dated Jan. 30, 2015, in counterpart Korean Application No. 10-2010-7006125.
Office Action issued Apr. 14, 2015 by the Japanese Patent Office in corresponding Japanese Application No. JP 2013-198915.

* cited by examiner

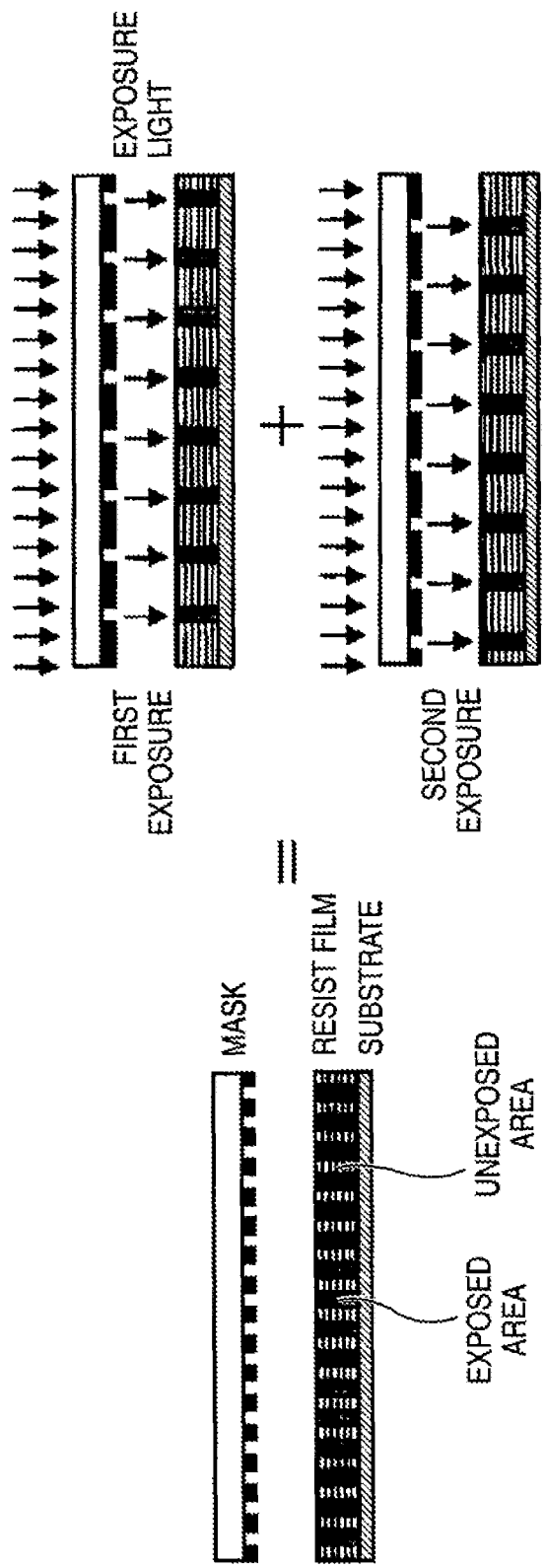

US 9,051,403 B2

PHOTOSENSITIVE COMPOSITION, PATTERN FORMING METHOD USING THE PHOTOSENSITIVE COMPOSITION AND COMPOUND FOR USE IN THE PHOTOSENSITIVE COMPOSITION

TECHNICAL FIELD

The present invention relates to a photosensitive composition that undergoes a reaction upon irradiation with an actinic ray or radiation to change in the property, a pattern forming method using the photosensitive composition, and a compound for use in the photosensitive composition. More specifically, the present invention relates to a photosensitive composition for use in the production process of a semiconductor such as IC, in the production of a liquid crystal device or a circuit board such as thermal heads, in other photofabrication processes, or in a lithographic printing plate or an acid-curable composition, a pattern forming method using the photosensitive composition, and a compound for use in the photosensitive composition.

BACKGROUND ART

A chemical amplification resist composition is a pattern forming material of forming a pattern on a substrate by producing an acid in the exposed area upon irradiation with an actinic ray or radiation such as far ultraviolet light and through a reaction using the acid as a catalyst, changing the developer solubility of the area irradiated with an actinic ray or radiation and that of the non-irradiated area.

A so-called immersion method of filling a high refractive-index liquid (hereinafter sometimes referred to as an "immersion liquid") between a projection lens and a sample has been conventionally known as a technique for enhancing the resolution in an optical microscope.

As for the "effect of immersion", assuming that $NA_0 = \sin\theta$, the resolution and the depth of focus in immersion can be expressed by the following formulae:

$$(\text{Resolution}) = k_1 \cdot (\lambda_0/n)/NA_0$$

$$(\text{Depth of focus}) = \pm k_2 \cdot (\lambda_0/n)/NA_0^2$$

wherein $\lambda_0$ is the wavelength of exposure light in air, n is the refractive index of the immersion liquid based on air, and $\theta$ is the convergence half-angle of beam.

That is, the effect of immersion is equal to use of an exposure wavelength of 1/n. In other words, when the projection optical system has the same NA, the depth of focus can be made n times larger by the immersion. This is effective for all pattern profiles and furthermore, can be combined with the super-resolution technology under study at present, such as phase-shift method and modified illumination method.

Examples of the apparatus where the effect above is applied to the transfer of a fine image pattern of a semiconductor device is described in Patent Document 1 (JP-A-57-153433 (the term "JP-A" as used herein means an "unexamined published Japanese patent application") and Patent Document 2.

Recent technical progress of the immersion exposure is reported, for example, in Non-Patent Document 1 and Patent Document 3. In the case of using an ArF excimer laser as a light source, pure water (refractive index at 193 nm: 1.44) is considered to be most promising as the immersion liquid in view of safety in handling as well as transmittance and refractive index at 193 nm. In the case of using an $F_2$ excimer laser as a light source, a fluorine-containing solution is being studied from the aspect of balance between transmittance and refractive index at 157 nm, but a sufficient solution in terms of environmental safety and refractive index has not yet been found. Considering the degree of immersion effect and the perfection of resist, the immersion exposure technique is expected to be most soon mounted on an ArF exposure machine.

Also, it is pointed out that when the chemical amplification resist is applied to immersion exposure, the resist layer comes into contact with the immersion liquid at the exposure, as a result, the resist layer deteriorates or a component adversely affecting the immersion liquid bleeds out from the resist layer. Patent Document 4 describes a case where when a resist for ArF exposure is dipped in water before and after exposure, the resist performance is changed, and this is indicated as a problem in the immersion exposure.

As for the medium filled between a projection lens and a semiconductor substrate, which is used in the immersion exposure, as described above, water having a refractive index of 1.44 is employed in view of easy availability and safety and by using an exposure machine having a projection lens with NA of 1.2 to 1.35, pattern formation of a semiconductor device in a design dimension up to the 45 nm generation is considered to be possible.

The generation next to the design dimension of 45 nm is 32 nm, and it is considered that NA of 1.65 is necessary for the pattern formation of a 32 nm-generation semiconductor device and in this case, the medium filled between a projection lens and a semiconductor substrate must have a refractive index of 1.8 or more.

Meanwhile, the material of a projection lens having NA of 1.65 is required to have a refractive index of 1.9 or more, and LuAg is currently supposed to be a promising candidate therefor, but its problem of absorbing a large amount of the passing light has not yet been solved.

Furthermore, a candidate medium having a refractive index of 1.8 or more has also not yet been found.

For these reasons, attention is directed toward a method where a special pattern forming method using an exposure machine with a projection lens having NA of 1.2 to 1.35 is used for the pattern formation of a 32 nm-generation semiconductor device.

Several methods have been proposed for this special pattern forming method, and one of these methods is a double exposure process.

The double exposure process is, as described in Patent Document 5, a process of exposing the same photoresist film two times, and this is a method where the pattern in the exposure field is divided into two pattern groups and the exposure is preformed in twice for respective pattern groups divided.

Patent Document 5 indicates that this method inevitably requires a property like a two-photon absorption resist, that is, a property of the photosensitivity or developer solubility being changed in proportion to the square of exposure intensity, but a resist having such a property has not yet been developed.

On the other hand, with miniaturization of a semiconductor, the diffusibility of an acid produced in the exposed area need to be deadly reduced. In Non-Patent Document 2, a compound obtained by fixing an acid to a polymer is reported, but many insufficient points still remain, and improvement of pattern profile, LER, pattern collapse, development defect and the like is demanded.

Patent Document 1: JP-A-57-153433

Patent Document 2: JP-A-7-220990

Patent Document 3: International Publication No. 04/077158, pamphlet
Patent Document 4: International Publication No. 04/068242, pamphlet
Patent Document 5: JP-A-2002-75857
Non-Patent Document 1: Proc. SPIE, Vol. 4688, page 11 (2002)
Non-Patent Document 2: Macromol Rapid Commun., 27, 1590-1595 (2006)

DISCLOSURE OF THE INVENTION

Problems that the Invention is to Solve

An object of the present invention is to provide a photosensitive composition ensuring good performance in terms of pattern profile and line edge roughness not only in normal exposure (dry exposure) but also in immersion exposure, a pattern forming method using the photosensitive composition, and a compound for use in the photosensitive composition. Another object of the present invention is to provide a photosensitive composition suitable for double exposure and ensuring good performance in terms of pattern profile and line edge roughness in double exposure, a pattern forming method using the photosensitive composition, and a compound for use in the photosensitive composition.

Means for Solving the Problems

The present invention is as follows.
[1] A photosensitive composition, comprising:
(A) a resin containing a repeating unit corresponding to a compound represented by the following formula (I), the resin being capable of producing an acid group upon irradiation with an actinic ray or radiation:

Z-A-X-B-R    (I)

wherein
Z represents a group capable of becoming an acid group resulting from leaving of a cation upon irradiation with an actinic ray or radiation;
A represents an alkylene group;
X represents a single bond or a heteroatom-containing divalent linking group;
B represents a single bond, an oxygen atom or —N(Rx)-;
Rx represents a hydrogen atom or a monovalent organic group;
R represents a monovalent organic group substituted by Y;
when B represents —N(Rx)-, R and Rx may combine with each other to form a ring; and
Y represents a polymerizable group.
[2] The photosensitive composition as described in [1] above,
wherein B in formula (I) represents an oxygen atom or —N(Rx)-.
[3] The photosensitive composition as described in [1] or [2] above,
wherein A in formula (I) contains a fluorine atom.
[4] The photosensitive composition as described in any one of [1] to [3] above,
wherein X in formula (I) represents a linking group selected from a single bond, —SO$_2$—, —SO— and —CO—.
[5] The photosensitive composition as described in any one of [1] to [4] above,
wherein Z in formula (I) represents a salt of an organic acid group selected from a sulfonic acid group, an imide acid group and a methide acid group.
[6] The photosensitive composition as described in any one of [1] to [5] above,
wherein Y in formula (I) is a group having a radical polymerizable unsaturated bond.
[7] The photosensitive composition as described in any one of [1] to [6] above,
wherein Y in formula (I) is selected from structures each having one addition-polymerizable unsaturated bond selected from an acrylic acid ester, a methacrylic acid ester, an acrylamide, a methacrylamide, an allyl, a vinyl ether and a vinyl ester.
[8] The photosensitive composition as described in any one of [1] to [7] above,
wherein the compound represented by formula (I) is a sulfonium salt compound or an iodonium salt compound.
[9] The photosensitive composition as described in any one of [1] to [8] above, which further comprises:
a hydrophobic resin (HR).
[10] The photosensitive composition as described in any one of [1] to [9] above, which further comprises:
(C) a compound capable of decomposing by an action of an acid to generate an acid.
[11] A pattern forming method, comprising:
steps of forming a photosensitive film from the photosensitive composition according to any one of [1] to [10] above; and
exposing and developing the photosensitive film.
[12] A pattern forming method, comprising:
steps of forming a photosensitive film from the photosensitive composition described in any one of [1] to [10] above;
further forming a hydrophobic resin as an overlayer of the photosensitive film; and
subjecting the photosensitive film to immersion exposure and development.
[13] A pattern forming method, comprising:
steps of forming a photosensitive film from the photosensitive composition described in any one of [1] to [10] above; and
subjecting the photosensitive film to immersion exposure and development.
[14] A pattern forming method, comprising:
steps of forming a photosensitive film from the photosensitive composition described in any one of [1] to [10] above; and
subjecting the photosensitive film to double exposure and development.
[15] A pattern forming method, comprising:
steps of forming a photosensitive film from the photosensitive composition described in any one of [1] to [10] above; and
subjecting the photosensitive film to immersion double exposure and development.
[16] A pattern forming method, comprising:
steps of forming a photosensitive film from the photosensitive composition described in any one of [1] to [10] above;
further forming a surface hydrophobizing resin as an overlayer of the photosensitive film; and
subjecting the photosensitive film to immersion double exposure and development.
[17] A compound represented by formula (I):

Z-A-X-B-R    (I)

wherein
Z represents a group capable of becoming an acid group resulting from leaving of a cation upon irradiation with an actinic ray or radiation;
A represents an alkylene group;

X represents a single bond or a heteroatom-containing divalent linking group;

B represents a single bond, an oxygen atom or —N(Rx)-;

Rx represents a hydrogen atom or a monovalent organic group;

R represents a monovalent organic group substituted by Y;

when B represents —N(Rx)-, R and Rx may combine with each other to form a ring; and Y represents a polymerizable group.

[18] A resin obtained by polymerizing a compound represented by formula (I) as at least one polymerization component:

Z-A-X-B-R            (I)

wherein

Z represents a group capable of becoming an acid group resulting from leaving of a cation upon irradiation with an actinic ray or radiation;

A represents an alkylene group;

X represents a single bond or a heteroatom-containing divalent linking group;

B represents a single bond, an oxygen atom or —N(Rx)-;

Rx represents a hydrogen atom or a monovalent organic group;

R represents a monovalent organic group substituted by Y;

when B represents —N(Rx)-, R and Rx may combine with each other to form a ring; and Y represents a polymerizable group.

Furthermore, the preferred embodiment of the present invention includes the following constructions.

[19] The photosensitive composition as described in any one of [1] to [10] above, which further comprises:

(B) a compound capable of generating an acid upon irradiation with an actinic ray or radiation.

[20] The photosensitive composition as described in [19] above, wherein the compound of the (B) compound component capable of generating an acid upon irradiation with an actinic ray or radiation is a sulfonium salt of an alkanesulfonic acid, a benzenesulfonic acid, an imide acid or a methide acid.

[21] The photosensitive composition as described in [19] or [20] above, wherein the compound of the (B) compound component capable of generating an acid upon irradiation with an actinic ray or radiation is a sulfonium salt of a fluoro-substituted alkanesulfonic acid, a fluorine-substituted benzenesulfonic acid, a fluorine-substituted imide acid or a fluorine-substituted methide acid.

[22] The photosensitive composition as described in [1] to [10] or [19] to [21] above, which further comprises:

(A') a resin not containing a repeating unit corresponding to the compound represented by formula (I).

[23] The photosensitive composition as described in [22] above, wherein the (A') resin not containing a repeating unit corresponding to the compound represented by formula (I) is a resin capable of increasing a solubility in an alkali developer by an action of an acid.

[24] The photosensitive positive resist composition as described in [1] to [10] or [19] to [23] above, wherein the resin of the component (A) or (A') further contains an acid-decomposable repeating unit having a monocyclic or polycyclic alicyclic hydrocarbon structure.

[25] The photosensitive composition as described in [1] to [10] or [19] to [24] above, wherein the resin of the component (A) or (A') further contains a repeating unit having a lactone structure.

[26] The photosensitive composition as described in [1] to [10] or [19] to [25] above, wherein the resin of the component (A) or (A') further contains a repeating unit having a hydroxyl group or a cyano group.

[27] The photosensitive composition as described in [1] to [10] or [19] to [26] above, wherein the resin of the component (A) or (A') further contains a repeating unit having a carboxyl group.

[28] The photosensitive composition as described in [1] to [10] or [19] to [27] above, wherein the resin of the component (A) or (A') further contains a repeating unit having a hexafluoroisopropanol structure.

[29] The photosensitive composition as described in [1] to [10] or [19] to [28] above, which further comprises:

a dissolution inhibiting compound having a molecular weight of 3,000 or less and being capable of decomposing by an action of an acid to increase a solubility in an alkali developer.

[30] The photosensitive composition as described in [1] to [10] or [19] to [29] above, which further comprises:

a basic compound; and at least one member selected from fluorine-containing and/or silicon-containing surfactants.

[31] The photosensitive composition as described in [30] above, wherein the basic compound is a compound having a structure selected from an imidazole structure, a diazabicyclo structure, an onium hydroxide structure, an onium carboxylate structure, a trialkylamine structure, an aniline structure and a pyridine structure, an alkylamine derivative having a hydroxyl group and/or an ether bond, or an aniline derivative having a hydroxyl group and/or an ether bond.

Advantage of the Invention

According to the present invention, a photosensitive composition ensuring good performance in terms of pattern profile and line edge roughness and reduction of pattern collapse and development defect not only in normal exposure (dry exposure) but also in immersion exposure, a pattern forming method using the photosensitive composition, and a compound for use in the photosensitive composition can be provided. Also, a photosensitive composition suitable for double exposure, ensuring good performance in terms of pattern profile and line edge roughness and reduction of pattern collapse and development defect in double exposure, a pattern forming method using the photosensitive composition, and a compound for use in the photosensitive composition can be provided.

BRIEF DESCRIPTION OF THE DRAWING

FIG. 1 is a schematic view showing the state in the double exposure process according to the present invention.

BEST MODE FOR CARRYING OUT THE INVENTION

The best mode for carrying out the present invention is described below.

Incidentally, in the present invention, when a group (atomic group) is denoted without specifying whether substituted or unsubstituted, the group includes both a group having no substituent and a group having a substituent. For example, an "alkyl group" includes not only an alkyl group having no substituent (unsubstituted alkyl group) but also an alkyl group having a substituent (substituted alkyl group).

(A) Resin Capable of Generating an Acid Group Upon Irradiation with an Actinic Ray or Radiation The photosensitive composition of the present invention contains a resin capable of generating an acid group upon irradiation with an actinic ray or radiation (hereinafter sometimes referred to as an "acid-generating resin").

In the present invention, the (A) resin capable of generating an acid group upon irradiation with an actinic ray or radiation contains a repeating unit corresponding to a compound represented by the following formula (I):

Z-A-X-B-R    (I)

In formula (I), Z represents a group capable of becoming an acid group resulting from leaving of a cation upon irradiation with an actinic ray or radiation.

A represents an alkylene group.

X represents a single bond or a heteroatom-containing divalent linking group.

B represents a single bond, an oxygen atom or —N(Rx)-.

Rx represents a hydrogen atom or a monovalent organic group.

R represents a monovalent organic group substituted by Y.

In the case where B represents —N(Rx)-, R and Rx may combine with each other to form a ring.

Y represents a polymerizable group.

A represents an alkylene group and is preferably an alkylene group having a carbon number of 1 to 8. The carbon number thereof is more preferably from 1 to 6, still more preferably from 1 to 4. The alkylene chain may contain a linking group such as oxygen atom and sulfur atom. The alkylene group may be substituted by a fluorine atom and in this case, an alkylene group where from 30 to 100% by number of the hydrogen atoms are replaced by a fluorine atom is preferred. It is more preferred that the carbon atom bonded to the Z site has a fluorine atom. A is still more preferably a perfluoroalkylene group and most preferably a perfluoromethylene group, a perfluoroethylene group, a perfluoropropylene group or a perfluorobutylene group. Thanks to such an alkylene group, the sensitivity is enhanced.

Z represents a group capable of becoming an acid group resulting from leaving of a cation upon irradiation with an actinic ray or radiation, and examples of the organic acid group that is produced from Z include an organic acid group such as carboxylic acid group, sulfonic acid group, imide acid group and methide acid group. Z is preferably a salt of an organic acid group selected from a sulfonic acid group, an imide acid group and a methide acid group, and in this case, the sensitivity is enhanced.

Examples of the heteroatom-containing divalent linking group of X include —SO$_2$—, —SO— and —CO—. X is preferably a linking group selected from a single bond, —SO$_2$—, —SO— and —CO—.

The monovalent organic group substituted by Y of R preferably has a carbon number of 4 to 30, and examples thereof include an alkyl group, a cycloalkyl group, an aryl group, an aralkyl group, an alkenyl group, an alkoxyl group and an alkoxycarbonylamino group.

The alkyl group as the organic group R may have a substituent and is preferably a linear or branched alkyl group having a carbon number of 1 to 30. The alkyl chain may contain an oxygen atom, a sulfur atom or a nitrogen atom. Specific examples of the alkyl group include a linear alkyl group such as methyl group, ethyl group, n-propyl group, n-butyl group, n-pentyl group, n-hexyl group, n-octyl group, n-dodecyl group, n-tetradecyl group and n-octadecyl group, and a branched alkyl group such as isopropyl group, isobutyl group, tert-butyl group, neopentyl group and 2-ethylhexyl group.

The cycloalkyl group as the organic group R may have a substituent and is preferably a cycloalkyl group having a carbon number of 3 to 20. The cycloalkyl group may be polycyclic and may contain an oxygen atom in the ring. Specific examples thereof include a cyclopropyl group, a cyclopentyl group, a cyclohexyl group, a norbornyl group and an adamantyl group.

The aryl group as the organic group R may have a substituent and is preferably an aryl group having a carbon number of 6 to 14, and examples thereof include a phenyl group and a naphthyl group.

The aralkyl group as the organic group R may have a substituent and is preferably an aralkyl group having a carbon number of 7 to 20, and examples thereof include a benzyl group, a phenethyl group, a naphthylmethyl group and a naphthylethyl group.

Examples of the alkenyl group as the organic group R include a group having a double bond at an arbitrary position of the above-described alkyl or cycloalkyl group.

The alkoxy group as the organic group R and the alkoxyl group in the alkoxycarbonylamino group are preferably an alkoxy group having a carbon number of 1 to 30, and examples thereof include a methoxy group, an ethoxy group, a propoxy group, an n-butoxy group, a pentyloxy group, a hexyloxy group and a heptyloxy group.

The monovalent organic group as Rx preferably has a carbon number of 1 to 40, more preferably a carbon number of 4 to 30, and examples thereof include an alkyl group, a cycloalkyl group, an aryl group, an aralkyl group, an alkenyl group, an alkoxy group, an alkoxycarbonylamino group and a cyano group. Details of the monovalent organic group as Rx are the same as those for R.

When B is —N(Rx)-, R and Rx may combine with each other to form a ring. By forming a ring structure, the stability is enhanced, and the composition using this compound is also enhanced in the storage stability. The carbon number of the ring formed is preferably from 4 to 20, and the ring may be monocyclic or polycyclic.

B preferably represents an oxygen atom or —N(Rx)-.

In the case where the organic group R is an aryl group or an aralkyl group or combines with Rx to form a ring, the organic group R and/or the organic group Rx preferably have a substituent Q. Examples of the substituent Q include a halogen atom, a nitro group, a cyano group, a carbonyl group, an alkyl group (preferably having a carbon number of 3 to 15), a cycloalkyl group (preferably having a carbon number of 3 to 10), an aryl group (preferably having a carbon number of 6 to 14), an alkoxy group (preferably having a carbon number of 1 to 10) and an acyl group (preferably having a carbon number of 2 to 20). Of these, a halogen atom, a nitro group, a cyano group, an alkyl group, a cycloalkyl group, an alkoxy group and an acyl group are preferred. The number of substituents is preferably 1 or more, and the substitution site is preferably on a carbon adjacent to the carbon bonded to B. Thanks to such a construction, the solvent solubility is more enhanced.

The polymerizable group as Y is preferably a group having a radical polymerizable unsaturated bond. R preferably has a carbon number of 1 to 20, more preferably a carbon number of 2 to 20, and examples thereof include a structure having one addition-polymerizable unsaturated bond selected from an acrylic acid ester, a methacrylic acid ester, an acrylamide, a methacrylamide, an allyl, a vinyl ether and a vinyl ester. Y is preferably an acrylic acid ester, a methacrylic acid ester, an acrylamide, a methacrylamide, an allyl or a vinyl ester.

Thanks to such a structure, an acid component capable of causing a deprotection reaction upon irradiation with an actinic ray or radiation can be generated on the side chain of a polymer, whereby diffusibility of an acid at the heating is deadly reduced as compared with a low molecular acid and the pattern profile, LER and pattern collapse are greatly improved.

With respect to the compound represented by formula (I), examples of the unit having an organic acid that is produced resulting from leaving of a cation upon irradiation with an actinic ray or radiation are set forth below.
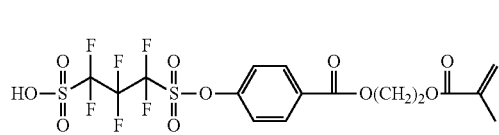
(X-1)
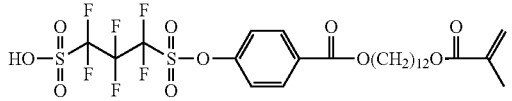
(X-2)
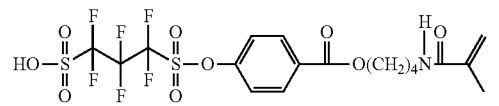
(X-3)
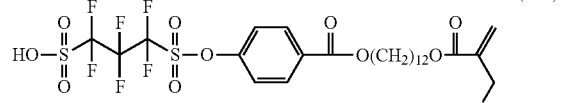
(X-4)
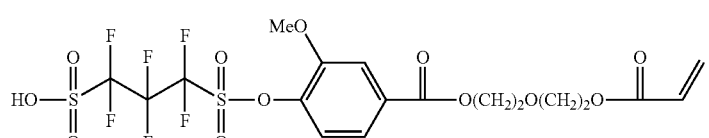
(X-5)
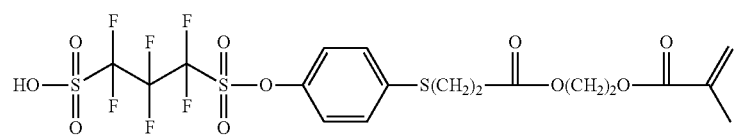
(X-6)
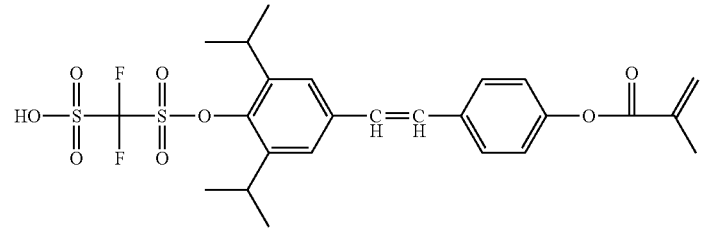
(X-7)
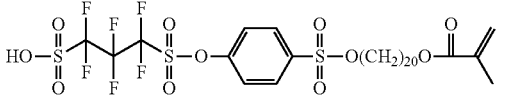
(X-8)
(X-9)
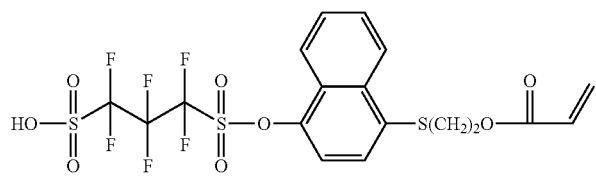
(X-10)
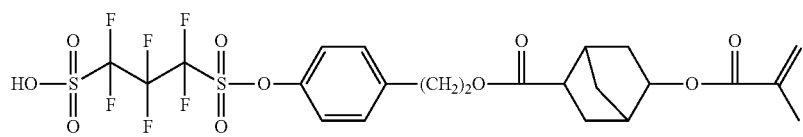
(X-11)
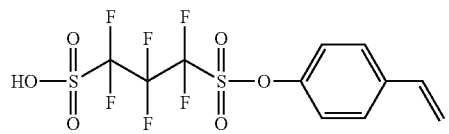
(X-12)
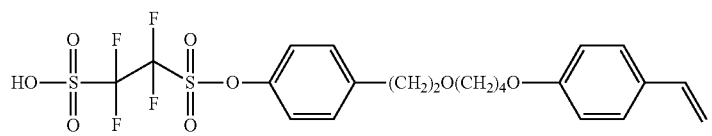
(X-13)

-continued
(X-14)
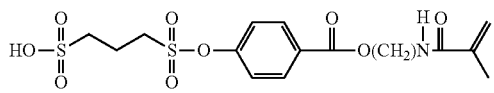
(X-15)
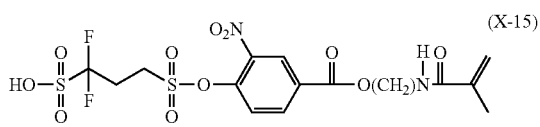
(X-16)
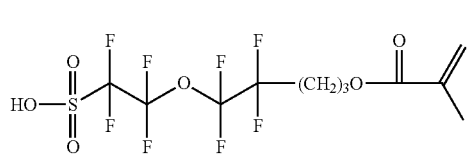
(X-17)
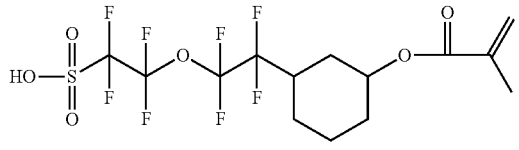
(X-18)
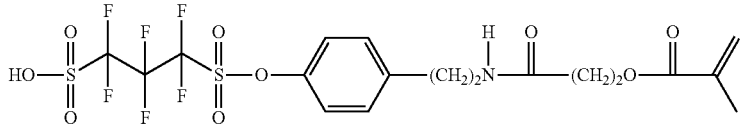
(X-19)
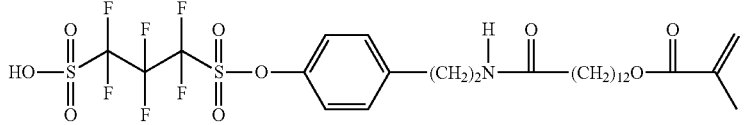
(X-20)
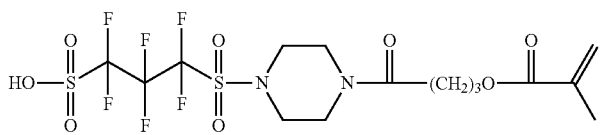
(X-21)
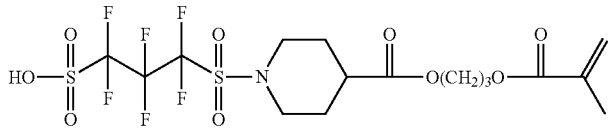
(X-22)
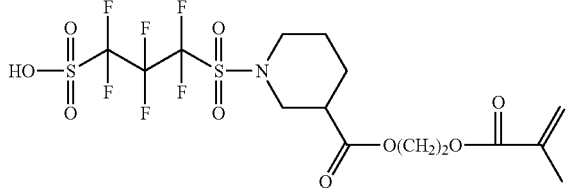
(X-23)
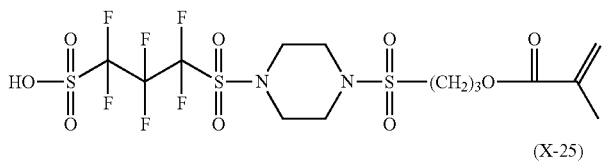
(X-24)
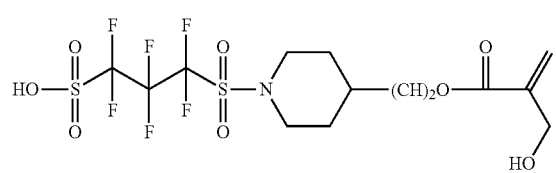
(X-25)
(X-26)
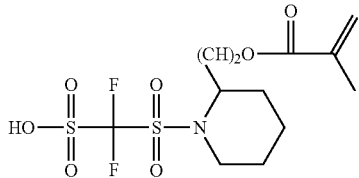

-continued
(X-27) 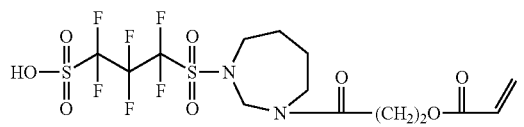
(X-28) 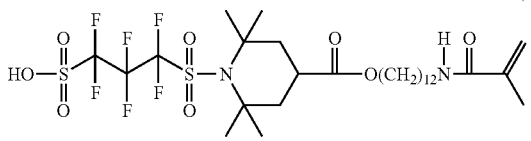
(X-29) 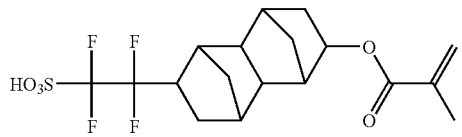
(X-30) 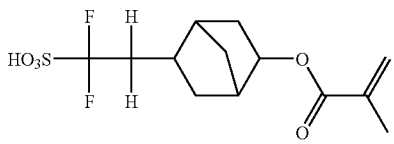
(X-31) 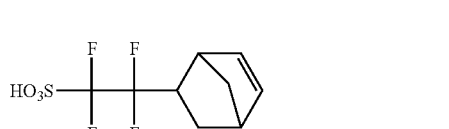
(X-32) 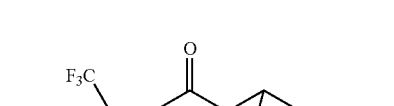
(X-33) 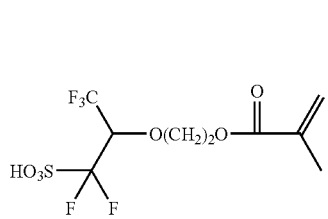
(X-34) 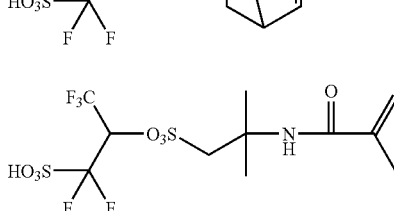
(X-35) 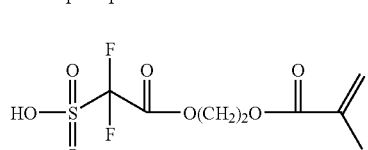
(X-36) 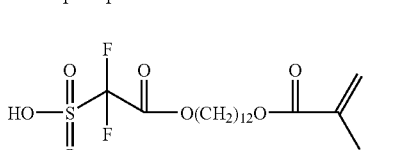
(X-37) 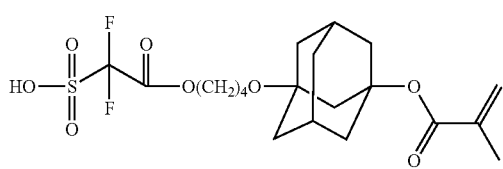
(X-38) 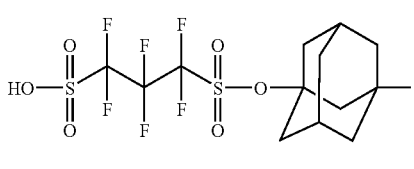
(X-39) 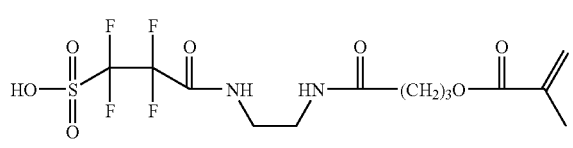
(X-40) 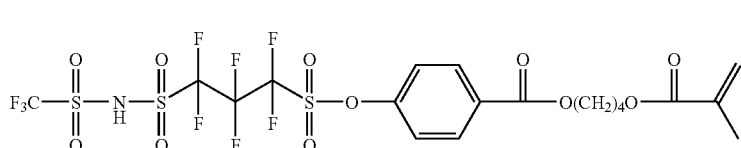
(X-41) 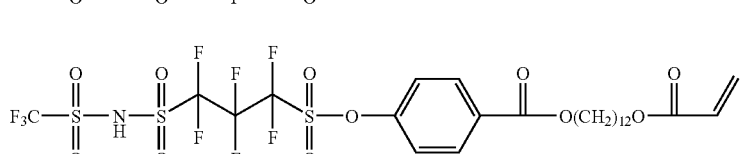
(X-42) 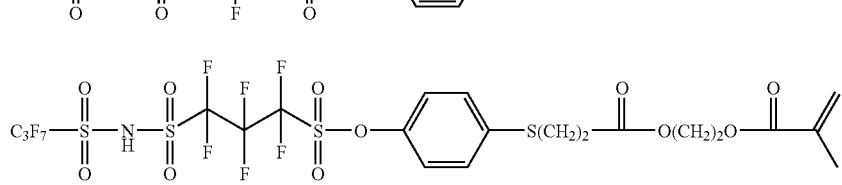

-continued
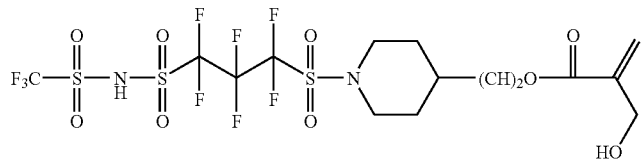
(X-43)
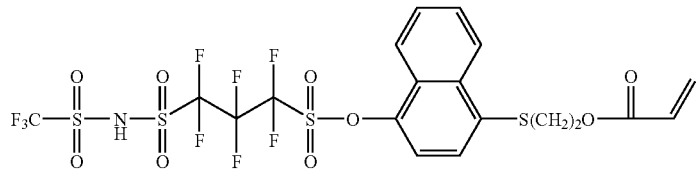
(X-44)
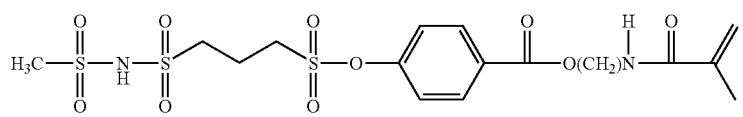
(X-45)
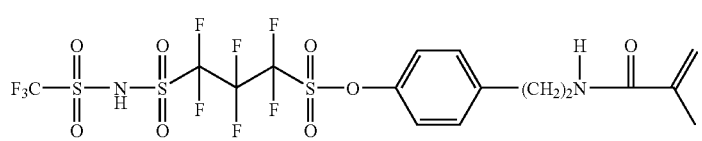
(X-46)
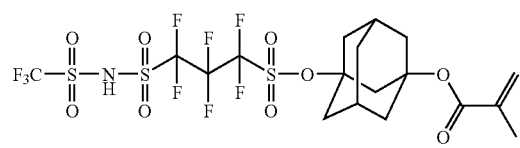
(X-47)
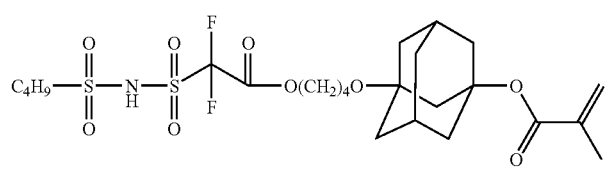
(X-48)
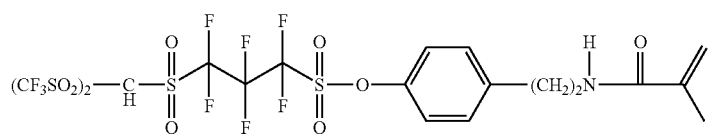
(X-49)
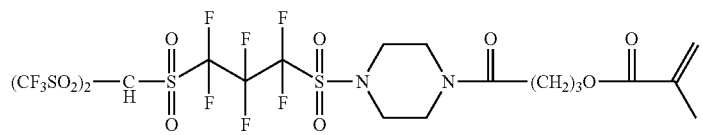
(X-50)
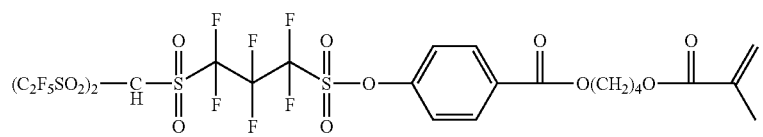
(X-51)
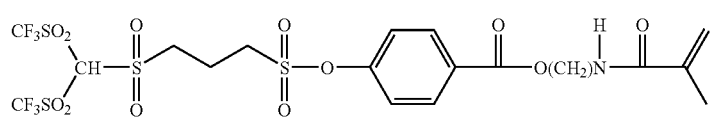
(X-52)
(X-53)

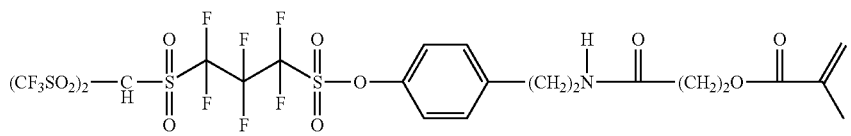
(X-54)

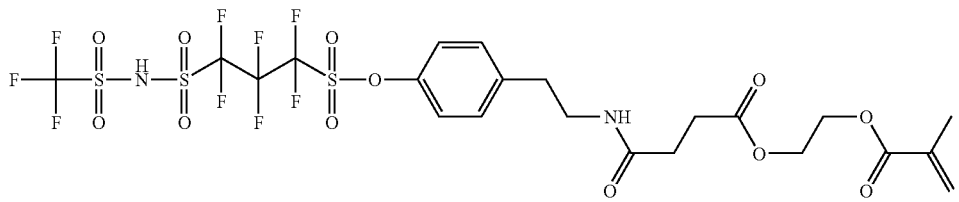
(X-55)

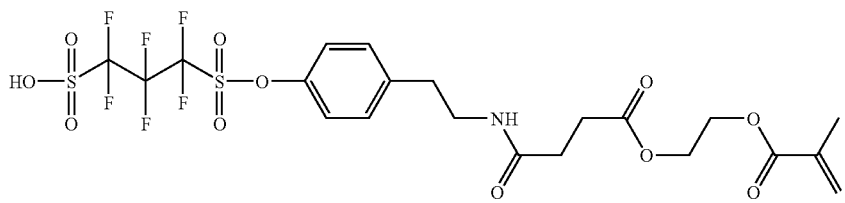
(X-56)

The compound represented by formula (I) can be synthesized using a general sulfonic acid esterification reaction or sulfonamidation reaction. For example, the organic acid corresponding to the compound represented by formula (I) may be obtained by a method of selectively reacting one sulfonyl halide moiety of a bis-sulfonyl halide compound with an amine, alcohol or the like containing a partial structure represented by formula (I) to form a sulfonamide bond or a sulfonic acid ester bond and then hydrolyzing the other sulfonyl halide moiety, or a method of ring-opening a cyclic sulfonic anhydride by an amine or alcohol containing a partial structure represented by formula (I). The compound may also be easily synthesized using the methods described in U.S. Pat. No. 5,554,664, J. Fluorine Chem., 105, 129-136 (2000), and J. Fluorine Chem., 116, 45-48 (2002).

The compound represented by formula (I) is preferably a sulfonium salt compound or an iodonium salt compound.

The sulfonium salt compound or iodonium salt compound of an organic acid corresponding to the compound represented by formula (I) can be easily synthesized from a lithium, sodium or potassium salt of the organic acid and a hydroxide, bromide, chloride or the like of iodonium or sulfonium, by utilizing the salt exchange method described in JP-T-11-501909 (the term "JP-T" as used herein means a "published Japanese translation of a PCT patent application") or JP-A-2003-246786.

Specific examples of the cation in the compound represented by formula (I) set forth below.

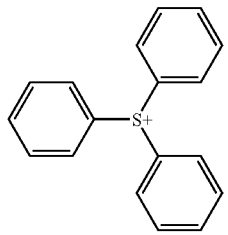
(I-1)

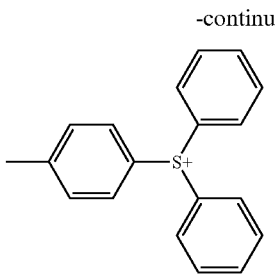
(I-2)

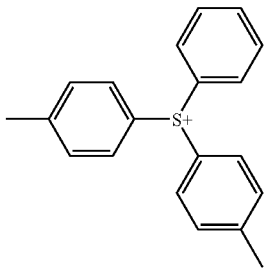
(I-3)

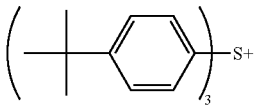
(I-4)

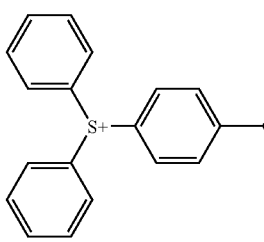
(I-5)

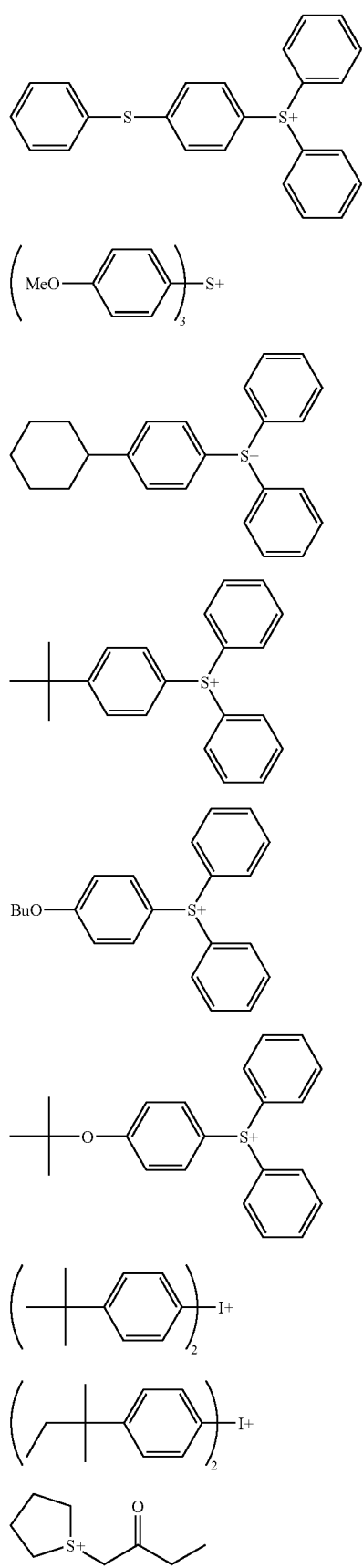
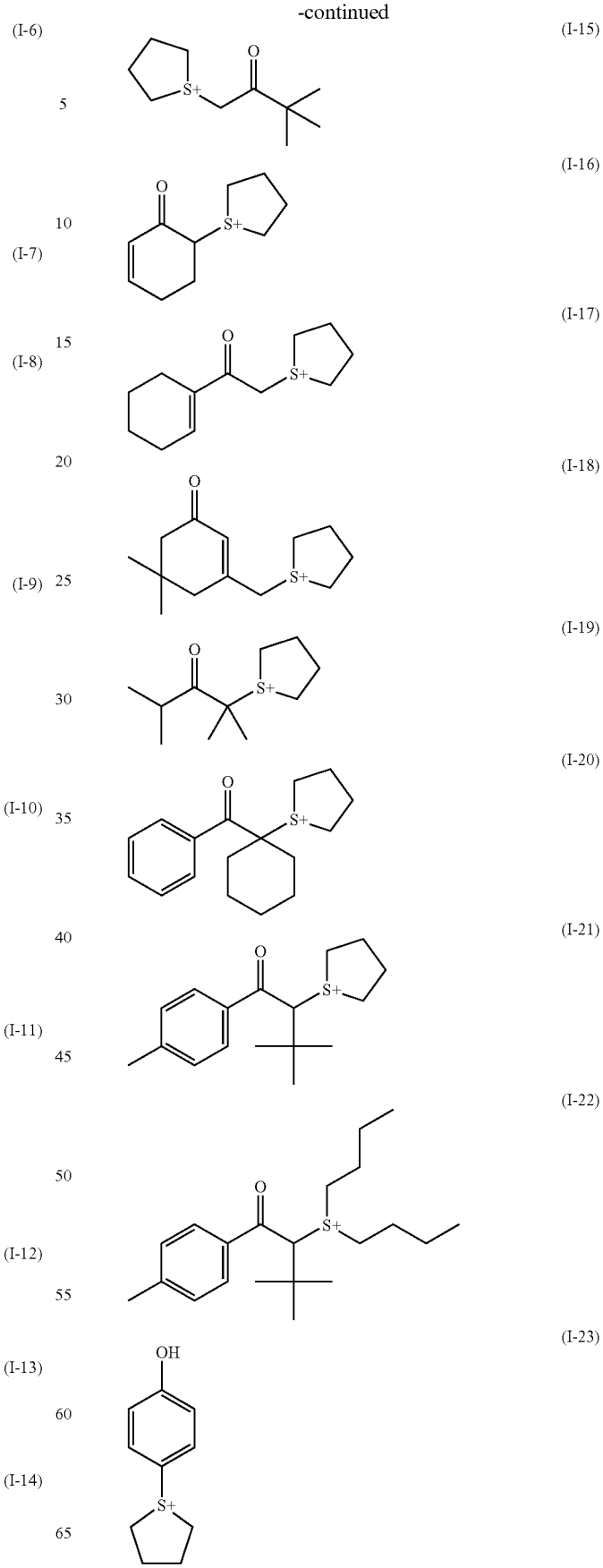

(I-24) 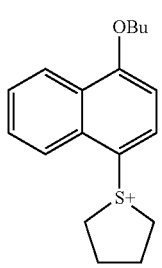
(I-25) 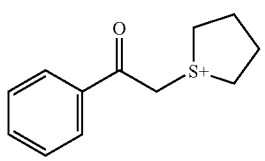
(I-26) 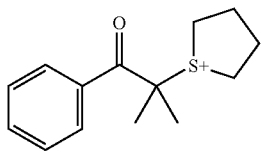
(I-27) 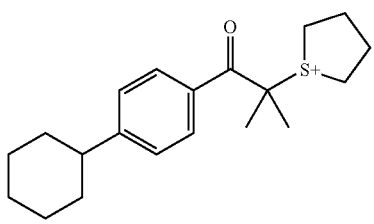
(I-28) 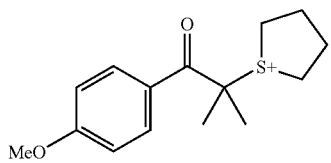
(I-29) 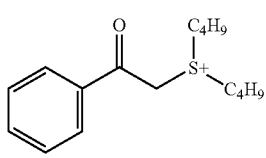
(I-30) 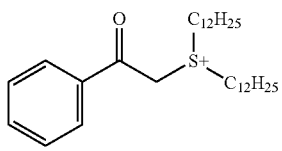
(I-31) 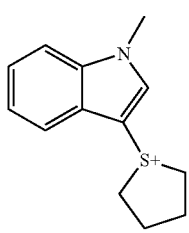
(I-32) 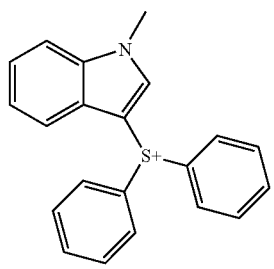
(I-33) 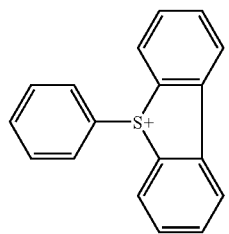
(I-34) 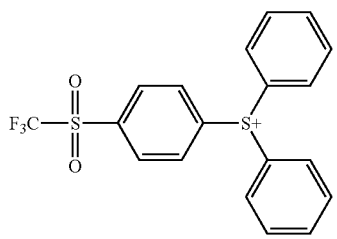
(I-35) 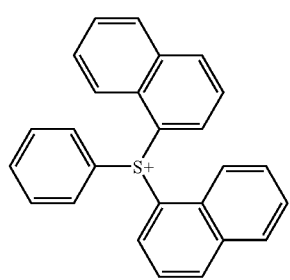
(I-36) 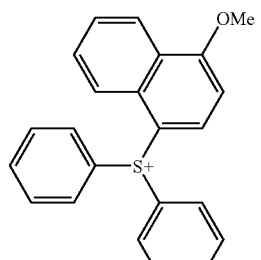
(I-37) 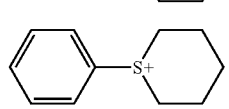
(I-38) 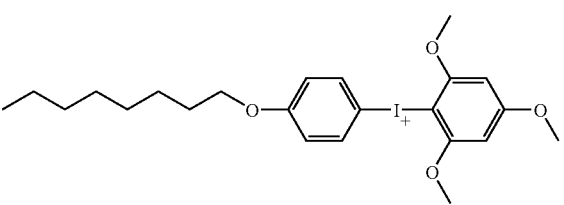

Also, specific example of the compound represented by formula (I) are shown in Table 1 below by the combination of a cation structure and an anion structure (an anion formed by removing a hydrogen atom of an organic acid in X-1 to X-56 above).

TABLE 1

| Cation Structure | Anion Structure | Compound A |
| --- | --- | --- |
| I-1 | X 1 | A-1 |
| I-1 | X 2 | A-2 |
| I-1 | X 3 | A-3 |
| I-1 | X 4 | A-4 |
| I-1 | X 5 | A-5 |
| I-1 | X 6 | A-6 |
| I-1 | X 7 | A-7 |
| I-1 | X 8 | A-8 |
| I-1 | X 9 | A-9 |
| I-1 | X 10 | A-10 |
| I-1 | X 11 | A-11 |
| I-1 | X 12 | A-12 |
| I-1 | X 13 | A-13 |
| I-1 | X 14 | A-14 |
| I-1 | X 15 | A-15 |
| I-1 | X 16 | A-16 |
| I-1 | X 17 | A-17 |
| I-1 | X 18 | A-18 |
| I-1 | X 19 | A-19 |
| I-1 | X 20 | A-20 |
| I-1 | X 21 | A-21 |
| I-1 | X 22 | A-22 |
| I-1 | X 23 | A-23 |
| I-1 | X 24 | A-24 |
| I-1 | X 25 | A-25 |
| I-1 | X 26 | A-26 |
| I-1 | X 27 | A-27 |
| I-1 | X 28 | A-28 |
| I-1 | X 29 | A-29 |
| I-1 | X 30 | A-30 |
| I-1 | X 31 | A-31 |
| I-1 | X 32 | A-32 |
| I-1 | X 33 | A-33 |
| I-1 | X 34 | A-34 |
| I-1 | X 35 | A-35 |
| I-1 | X 36 | A-36 |
| I-1 | X 37 | A-37 |
| I-1 | X 38 | A-38 |
| I-1 | X 39 | A-39 |
| I-1 | X 40 | A-40 |
| I-1 | X 41 | A-41 |
| I-1 | X 42 | A-42 |
| I-1 | X 43 | A-43 |
| I-1 | X 44 | A-44 |
| I-1 | X 45 | A-45 |
| I-1 | X 46 | A-46 |
| I-1 | X 47 | A-47 |
| I-1 | X 48 | A-48 |
| I-1 | X 49 | A-49 |
| I-1 | X 50 | A-50 |
| I-1 | X 51 | A-51 |
| I-1 | X 52 | A-52 |
| I-1 | X 53 | A-53 |
| I-1 | X 54 | A-54 |
| I-24 | X 29 | A-55 |
| I-34 | X 30 | A-56 |
| I-11 | X 32 | A-57 |
| I-11 | X 33 | A-58 |
| I-25 | X 34 | A-59 |
| I-25 | X 35 | A-60 |
| I-4 | X 37 | A-61 |
| I-4 | X 32 | A-62 |
| I-35 | X 35 | A-63 |
| I-36 | X 37 | A-64 |
| I-37 | X 32 | A-65 |
| I-2 | X 10 | A-66 |
| I-2 | X 18 | A-67 |
| I-2 | X 23 | A-68 |
| I-2 | X 43 | A-69 |
| I-2 | X 46 | A-70 |

TABLE 1-continued

| Cation Structure | Anion Structure | Compound A |
| --- | --- | --- |
| I-2 | X 50 | A-71 |
| I-4 | X 2 | A-72 |
| I-4 | X 18 | A-73 |
| I-4 | X 23 | A-74 |
| I-4 | X 43 | A-75 |
| I-4 | X 46 | A-76 |
| I-4 | X 50 | A-77 |
| I-8 | X 2 | A-78 |
| I-8 | X 18 | A-79 |
| I-8 | X 23 | A-80 |
| I-8 | X 43 | A-81 |
| I-8 | X 46 | A-82 |
| I-8 | X 50 | A-83 |
| I-9 | X 2 | A-84 |
| I-9 | X 18 | A-85 |
| I-9 | X 23 | A-86 |
| I-9 | X 43 | A-87 |
| I-9 | X 46 | A-88 |
| I-9 | X 50 | A-89 |
| I-25 | X 2 | A-90 |
| I-25 | X 18 | A-91 |
| I-25 | X 23 | A-92 |
| I-25 | X 43 | A-93 |
| I-25 | X 46 | A-94 |
| I-25 | X 50 | A-95 |
| I-27 | X 2 | A-96 |
| I-27 | X 18 | A-97 |
| I-27 | X 23 | A-98 |
| I-27 | X 43 | A-99 |
| I-27 | X 46 | A-100 |
| I-27 | X 50 | A-101 |
| I-29 | X 18 | A-102 |
| I-29 | X 46 | A-103 |
| I-31 | X 2 | A-104 |
| I-31 | X 18 | A-105 |
| I-31 | X 23 | A-106 |
| I-31 | X 43 | A-107 |
| I-31 | X 46 | A-108 |
| I-31 | X 50 | A-109 |
| I-38 | X 18 | A-110 |
| I-38 | X 46 | A-111 |
| I-11 | X 18 | A-112 |
| I-11 | X 46 | A-113 |
| I-33 | X 18 | A-114 |
| I-33 | X 46 | A-115 |
| I-1 | X 55 | A-116 |
| I-2 | X 55 | A-117 |
| I-4 | X 55 | A-118 |
| I-8 | X 55 | A-119 |
| I-9 | X 55 | A-120 |
| I-33 | X 55 | A-121 |
| I-31 | X 56 | A-122 |

In the photosensitive composition of the present invention, the resin of the component (A) preferably contains a repeating unit having a group capable of decomposing by the action of an acid to produce an alkali-soluble group (hereinafter sometimes referred to as an "acid-decomposable group"), on either one or both of the main chain and the side chain of the resin.

Examples of the alkali-soluble group include a phenolic hydroxyl group, a carboxyl group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis (alkylcarbonyl)methylene group, a bis(alkylcarbonyl)imide group, a bis(alkylsulfonyl)methylene group, a bis(alkylsulfonyl)imide group, a tris(alkylcarbonyl)methylene group and a tris(alkylsulfonyl)methylene group.

Preferred examples of the alkali-soluble group include a carboxyl group, a fluorinated alcohol group (preferably hexafluoroisopropanol) and a sulfonic acid group.

The group preferred as the acid-decomposable group is a group where a hydrogen atom of the alkali-soluble group above is replaced by a group capable of leaving by the action of an acid.

Examples of the group capable of leaving by the action of an acid include —C($R_{36}$)($R_{37}$)($R_{38}$), —C($R_{36}$)($R_{37}$)(O$R_{39}$) and —C($R_{01}$)($R_{02}$)(O$R_{39}$).

In the formulae, each of $R_{36}$ to $R_{39}$ independently represents an alkyl group, a cycloalkyl group, an aryl group, an aralkyl group or an alkenyl group, and $R_{36}$ and $R_{37}$ may combine with each other to form a ring.

Each of $R_{01}$ and $R_{02}$ independently represents a hydrogen atom, an alkyl group, a cycloalkyl group, an aryl group, an aralkyl group or an alkenyl group.

The acid-decomposable group is preferably a cumyl ester group, an enol ester group, an acetal ester group, a tertiary alkyl ester group or the like, more preferably a tertiary alkyl ester group.

The resin of the component (A) preferably contains a repeating unit having an acid-decomposable group. The repeating unit having an acid-decomposable group is preferably a repeating unit represented by the following formula (AI):

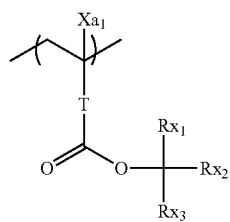

(AI)

In formula (AI), $Xa_1$ represents a hydrogen atom, a methyl group, a trifluoromethyl group or a hydroxymethyl group.

T represents a single bond or a divalent linking group.

Each of $Rx_1$ to $Rx_3$ independently represents an alkyl group (linear or branched) or a cycloalkyl group (monocyclic or polycyclic).

At least two members out of $Rx_1$ to $Rx_3$ may combine with each other to form a cycloalkyl group (monocyclic or polycyclic).

Examples of the divalent linking group of T include an alkylene group, a —COO-Rt- group and a —O-Rt- group, wherein Rt represents an alkylene group or a cycloalkylene group.

T is preferably a single bond or a —COO-Rt- group. Rt is preferably an alkylene group having a carbon number of 1 to 5, more preferably a —CH$_2$— group or a —(CH$_2$)$_3$— group.

The alkyl group of $Rx_1$ to $Rx_3$ is preferably an alkyl group having a carbon number of 1 to 4, such as methyl group, ethyl group, n-propyl group, isopropyl group, n-butyl group, isobutyl group and tert-butyl group.

The cycloalkyl group of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

The cycloalkyl group formed by combining at least two members out of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

An embodiment where $Rx_1$ is a methyl group or an ethyl group and $Rx_2$ and $Rx_3$ are combined to form the above-described cycloalkyl group is preferred.

The content of the repeating unit having an acid-decomposable group is preferably from 20 to 50 mol %, more preferably from 25 to 45 mol %, based on all repeating units in the polymer.

Specific preferred examples of the repeating unit having an acid-decomposable group are set forth below, but the present invention is not limited thereto.

(In formulae, Rx represents H, CH$_3$, CF$_3$ or CH$_2$OH, and each of Rxa and Rxb represents an alkyl group having a carbon number of 1 to 4.)

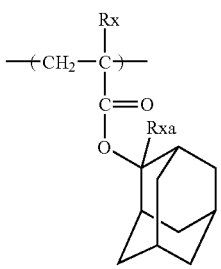

1

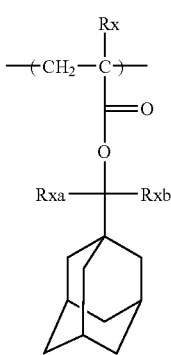

2

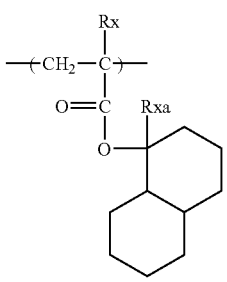

3

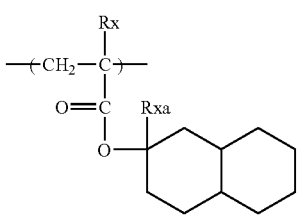

4

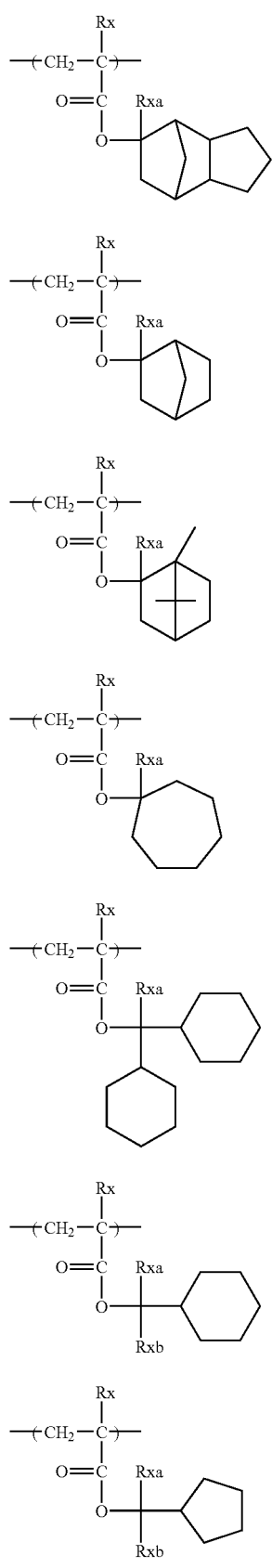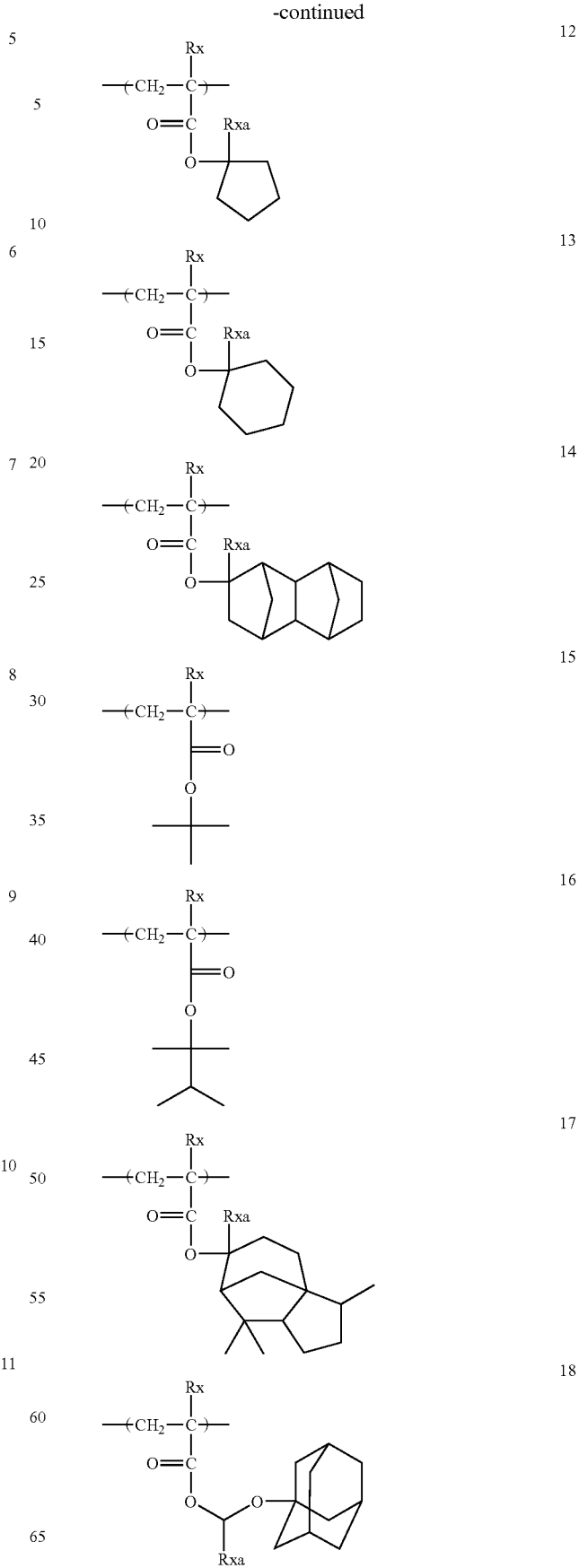

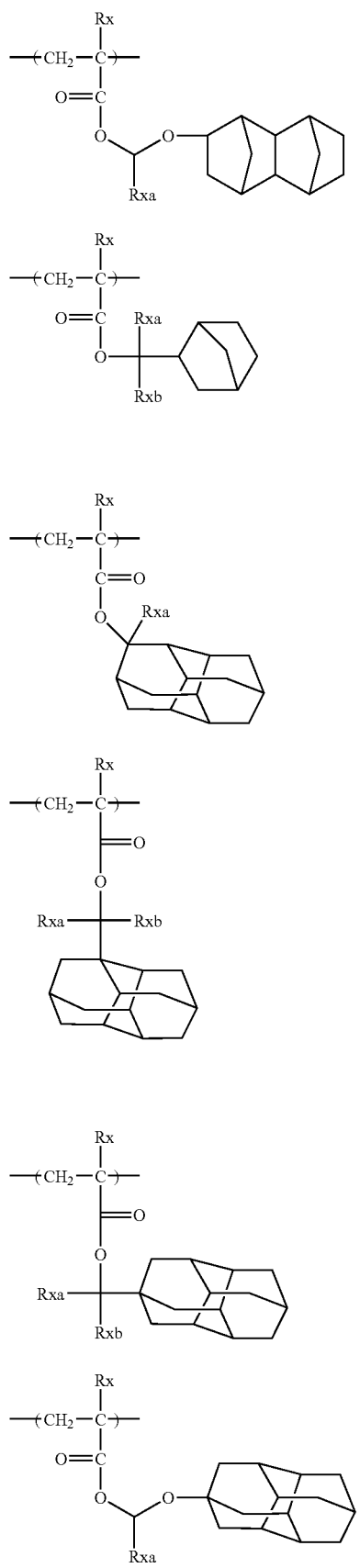
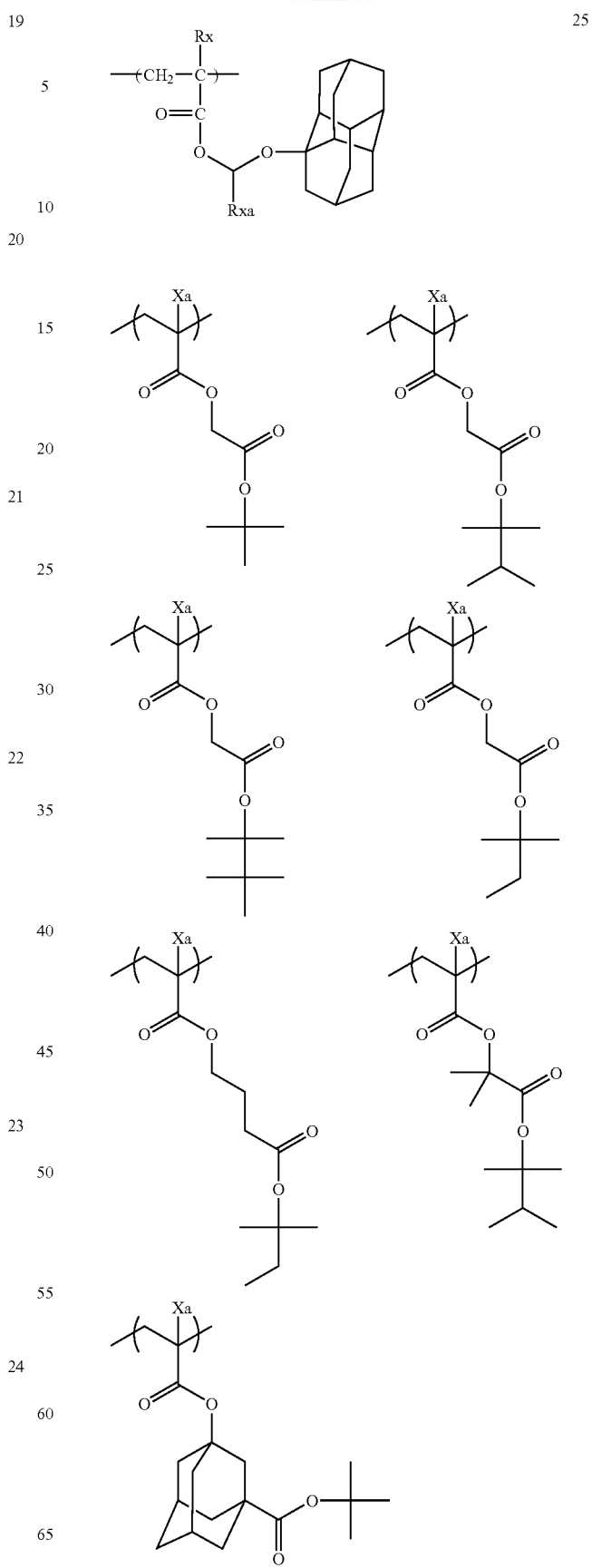

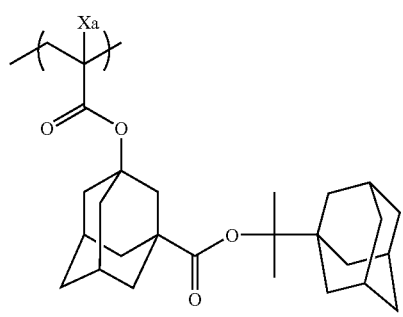
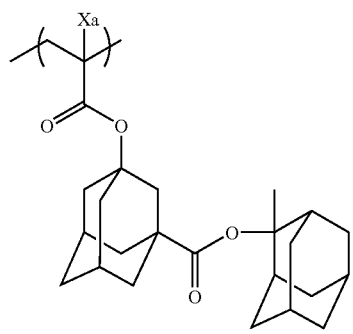
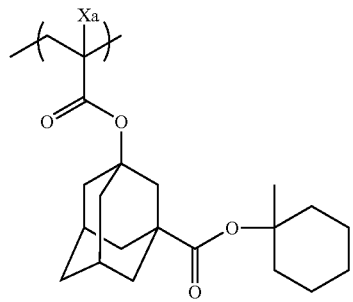
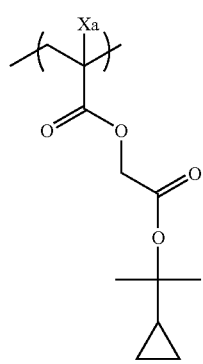
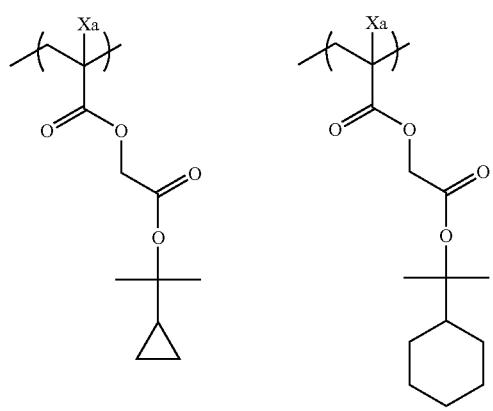
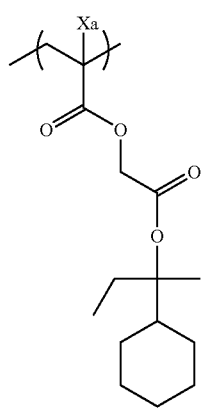
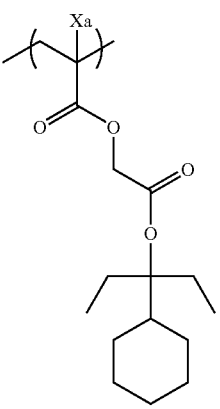
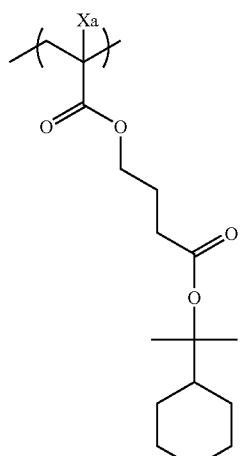
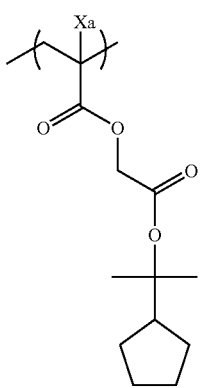
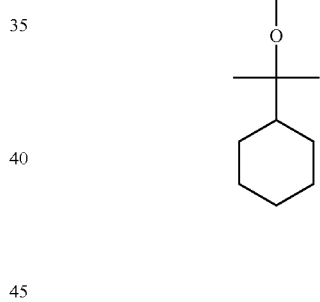
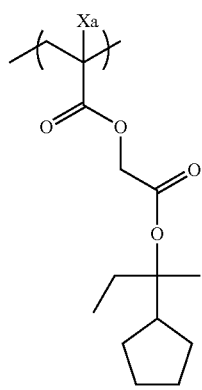
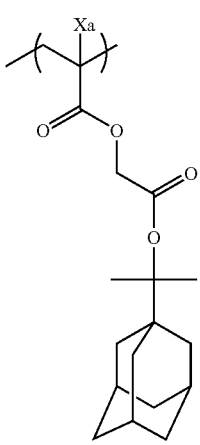

-continued
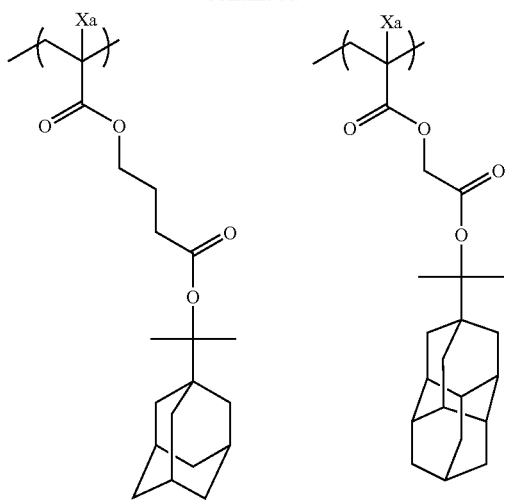 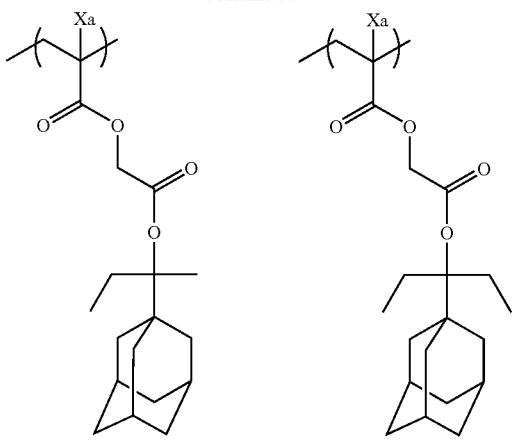
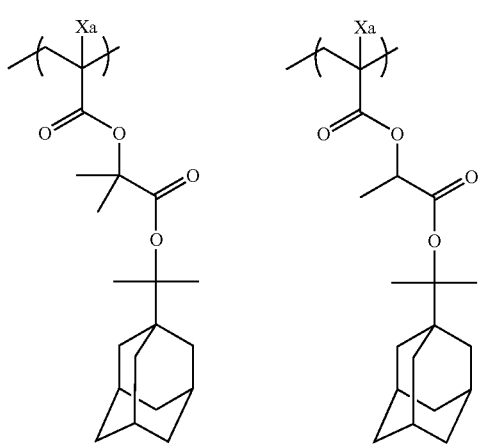 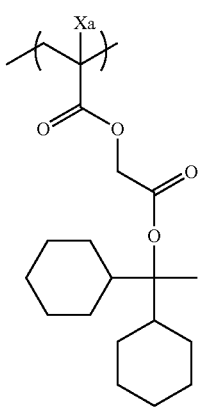 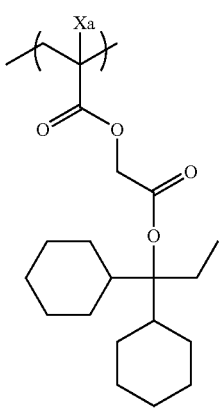
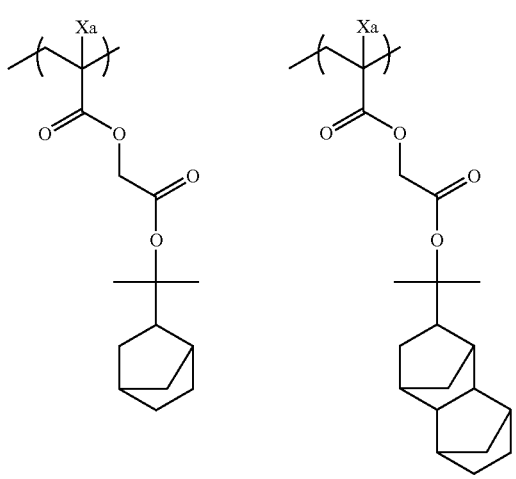 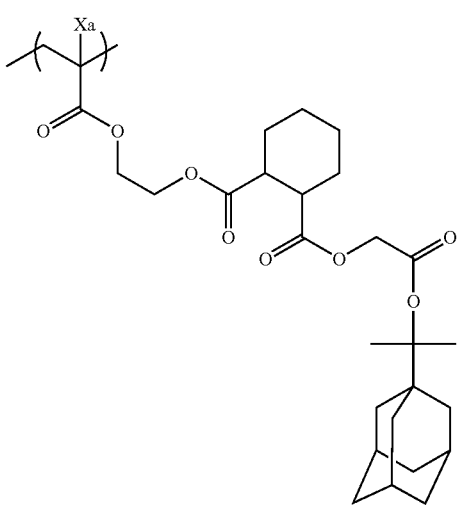

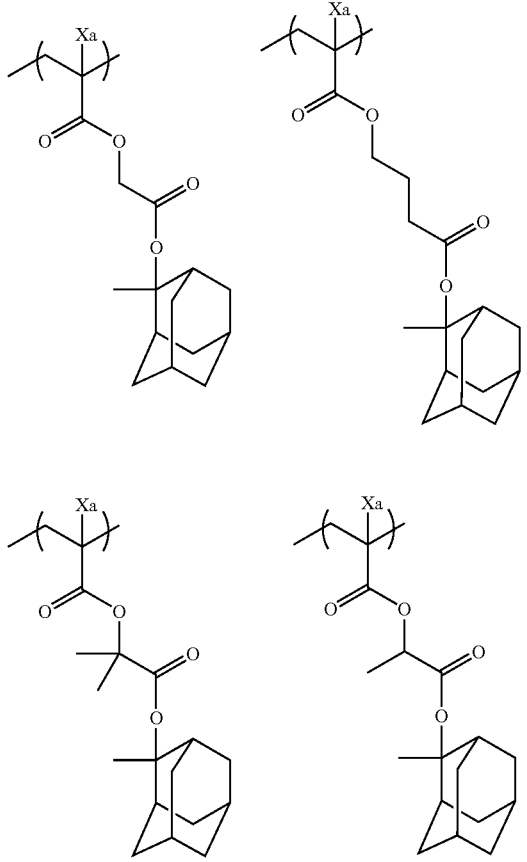
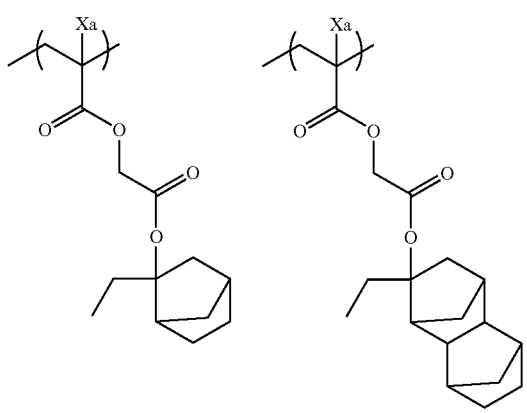
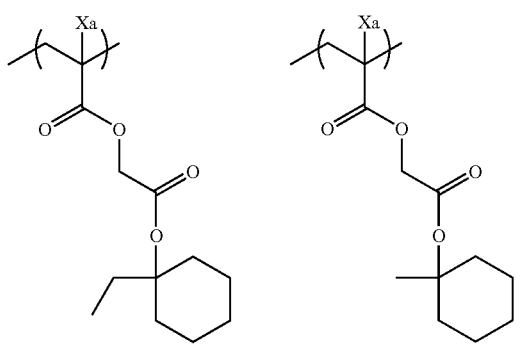
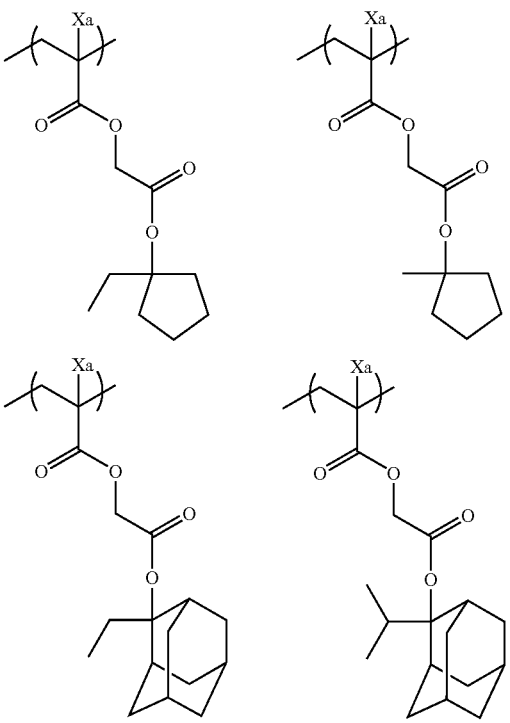

The resin of the component (A) preferably contains a repeating unit having at least one kind of a group selected from a lactone group, a hydroxyl group, a cyano group and an alkali-soluble group.

The resin of the component (A) preferably contains a repeating unit having a lactone group.

As for the lactone group, any group may be used as long as it has a lactone structure, but the lactone structure is preferably a 5- to 7-membered ring lactone structure, and a structure where another ring structure is condensed with a 5- to 7-membered ring lactone structure in the form of forming a bicyclo or spiro structure is preferred. The resin more preferably contains a repeating unit having a lactone structure represented by any one of the following formulae (LC1-1) to (LC1-16). The lactone structure may be bonded directly to the main chain. Among these lactone structures, preferred are (LC1-1), (LC1-4), (LC1-5), (LC1-6), (LC1-13) and (LC1-14). By using a specific lactone structure, the line edge roughness and development defect are improved.

LC1-1
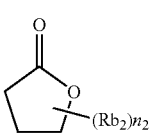

LC1-2
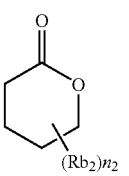

LC1-3 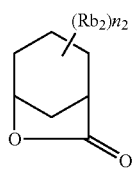

LC1-4 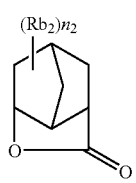

LC1-5 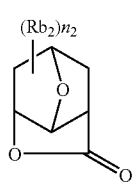

LC1-6 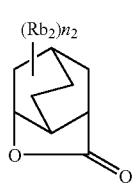

LC1-7 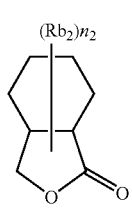

LC1-8 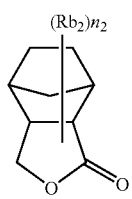

LC1-9 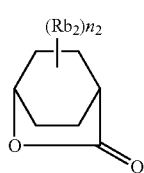

LC1-10 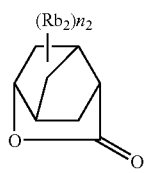

LC1-11 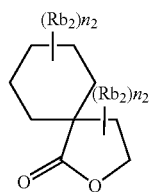

LC1-12 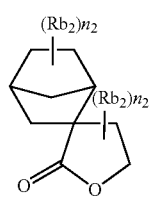

LC1-13 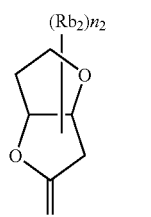

LC1-14 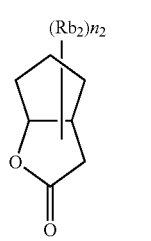

LC1-15 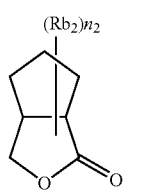

LC1-16 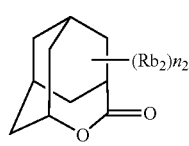

The lactone structure moiety may or may not have a substituent ($Rb_2$). Preferred examples of the substituent ($Rb_2$) include an alkyl group having a carbon number of 1 to 8, a cycloalkyl group having a carbon number of 4 to 7, an alkoxy group having a carbon number of 1 to 8, an alkoxycarbonyl group having a carbon number of 1 to 8, a carboxyl group, a halogen atom, a hydroxyl group, a cyano group and an acid-decomposable group. Among these, an alkyl group having a carbon number of 1 to 4, a cyano group and an acid-decomposable group are more preferred. $n_2$ represents an integer of 0 to 4. When $n_2$ is an integer of 2 or more, each substituent ($Rb_2$) may be the same as or different from every other substituent ($Rb_2$) and also, the plurality of substituents ($Rb_2$) may combine with each other to form a ring.

The repeating unit having a lactone structure represented by any one of formulae (LC1-1) to (LC1-16) includes a repeating unit represented by the following formula (AII):

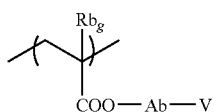
(AII)

In formula (AII), $Rb_0$ represents a hydrogen atom, a halogen atom or an alkyl group having a carbon number of 1 to 4. Preferred examples of the substituent which the alkyl group of $Rb_0$ may have include a hydroxyl group and a halogen atom. The halogen atom of $Rb_0$ includes a fluorine atom, a chlorine atom, a bromine atom and an iodine atom. $Rb_0$ is preferably a hydrogen atom or a methyl group.

Ab represents a single bond, an alkylene group, a divalent linking group having a monocyclic or polycyclic alicyclic hydrocarbon structure, an ether group, an ester group, a carbonyl group, or a divalent group comprising a combination thereof, and is preferably a single bond or a divalent linking group represented by -$Ab_1$-$CO_2$—. $Ab_1$ represents a linear or branched alkylene group or a monocyclic or polycyclic cycloalkylene group and is preferably a methylene group, an ethylene group, a cyclohexylene group, an adamantylene group or a norbornylene group.

V represents a group having a structure represented by any one of formulae (LC1-1) to (LC1-16).

The repeating unit having a lactone group usually has an optical isomer, but any optical isomer may be used. One optical isomer may be used alone, or a plurality of optical isomers may be mixed and used. In the case of mainly using one optical isomer, the optical purity (ee) thereof is preferably 90 or more, more preferably 95 or more.

The content of the repeating unit having a lactone group is preferably from 15 to 60 mol %, more preferably from 20 to 50 mol %, still more preferably from 30 to 50 mol %, based on all repeating units in the polymer.

Specific examples of the repeating unit containing a lactone group are set forth below, but the present invention is not limited thereto.

(In the formulae, Rx represents H, $CH_3$, $CH_2OH$ or $CF_3$.)

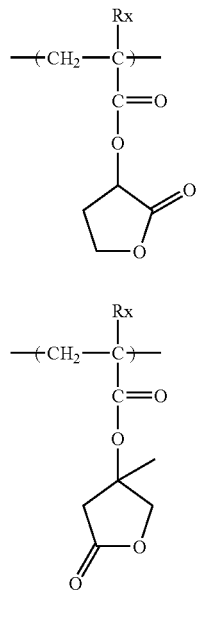

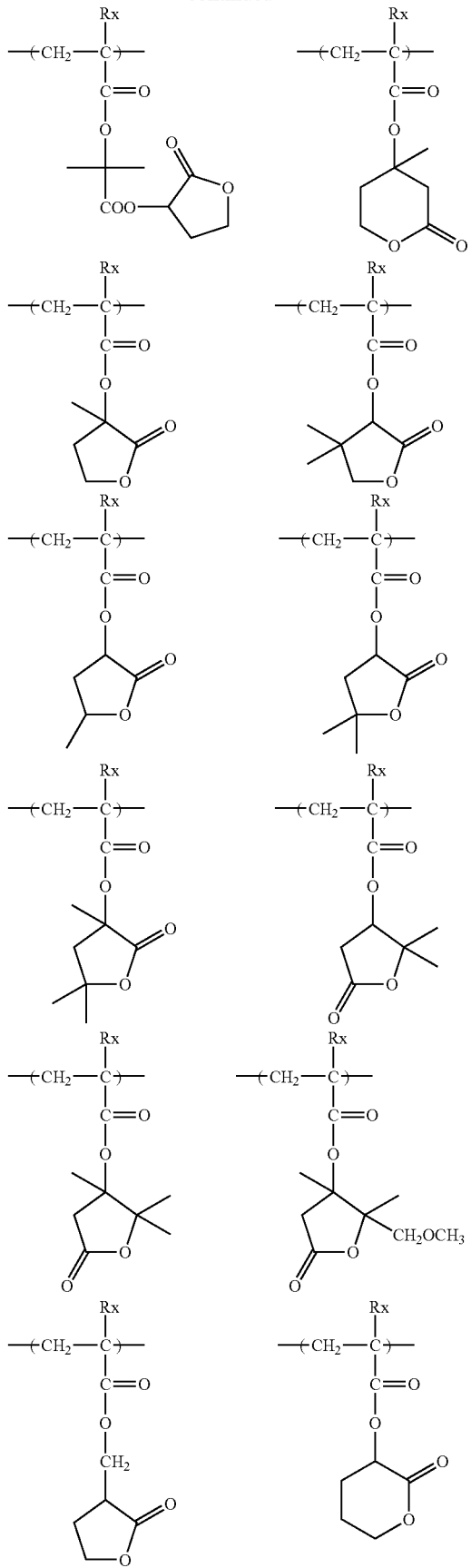

-continued
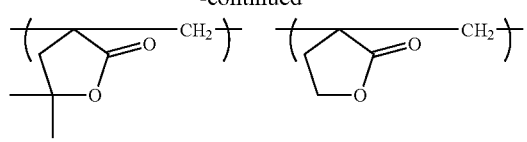
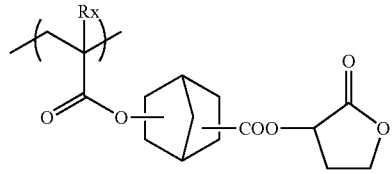
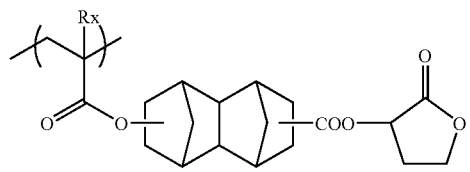
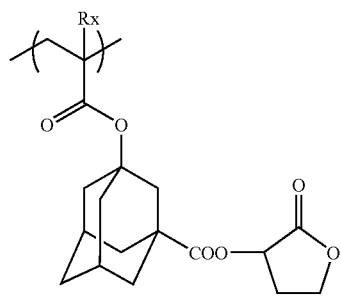
(In the formulae, Rx represents H, CH₃, CH₂OH or CF₃.)
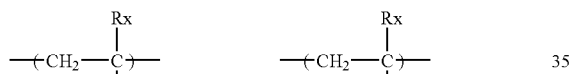
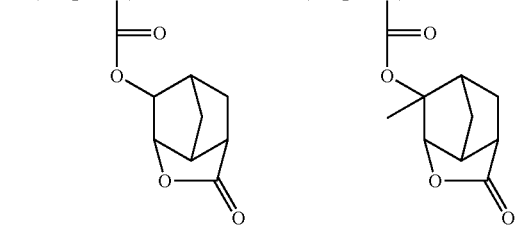
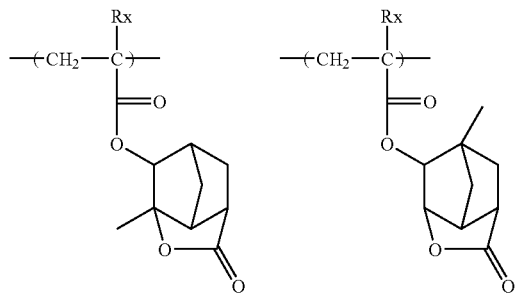
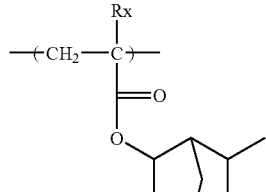
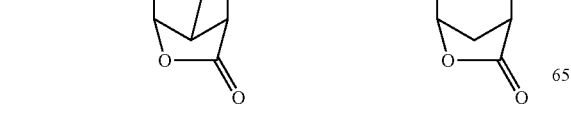
-continued
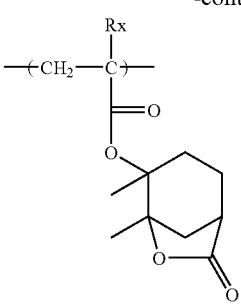 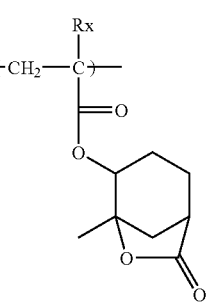
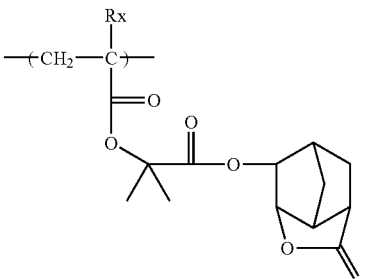
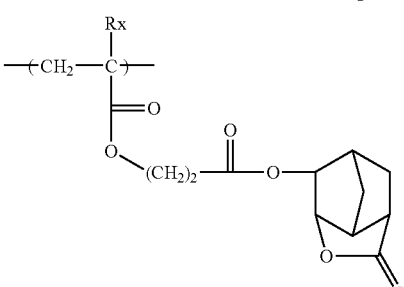
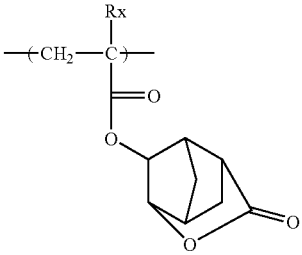
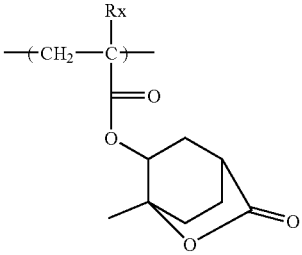
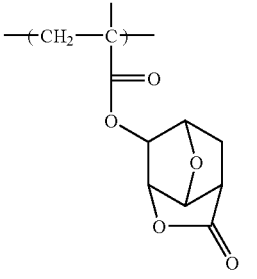

-continued
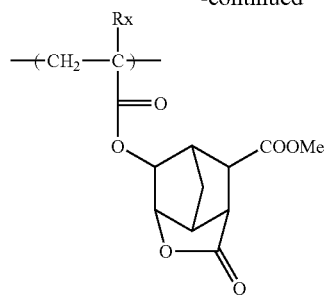
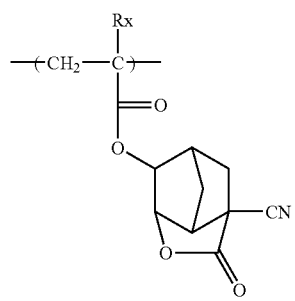
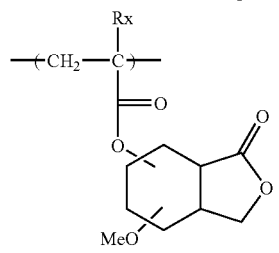
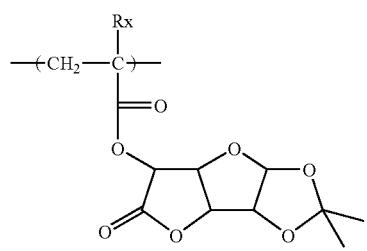
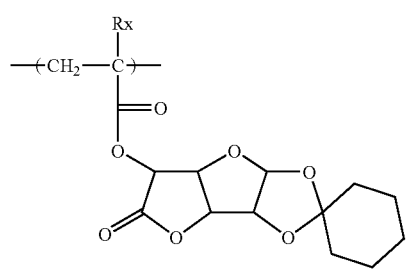
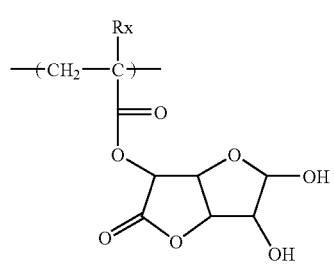
-continued
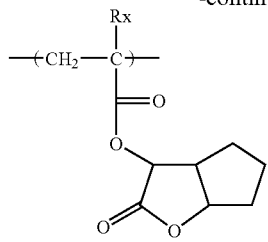
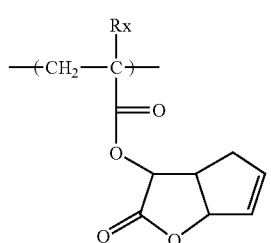
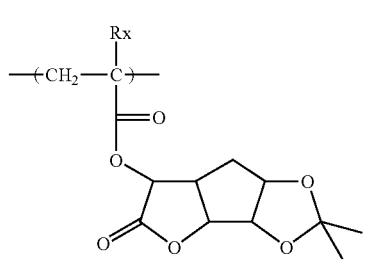
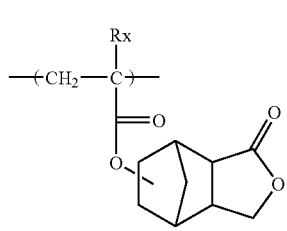
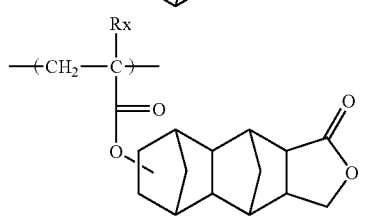
(In the formulae, Rx represent H, $CH_3$, $CH_2OH$ or $CF_3$.)
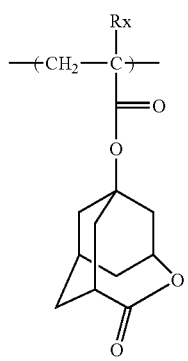 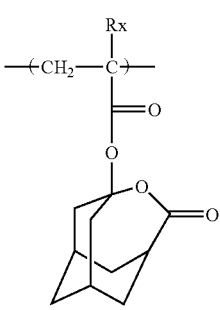

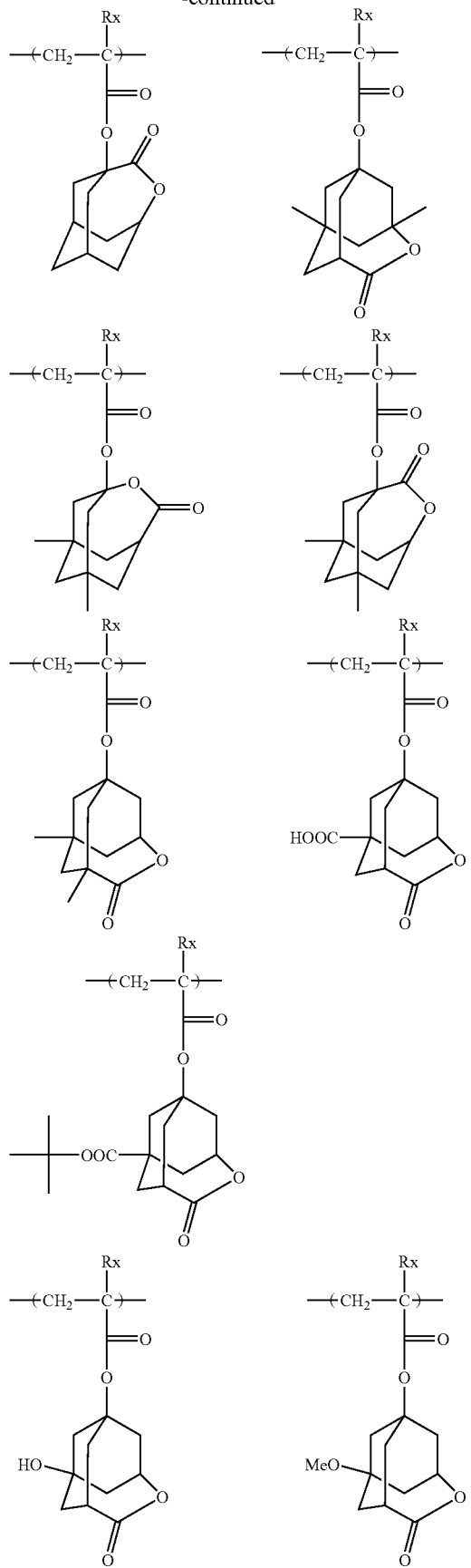
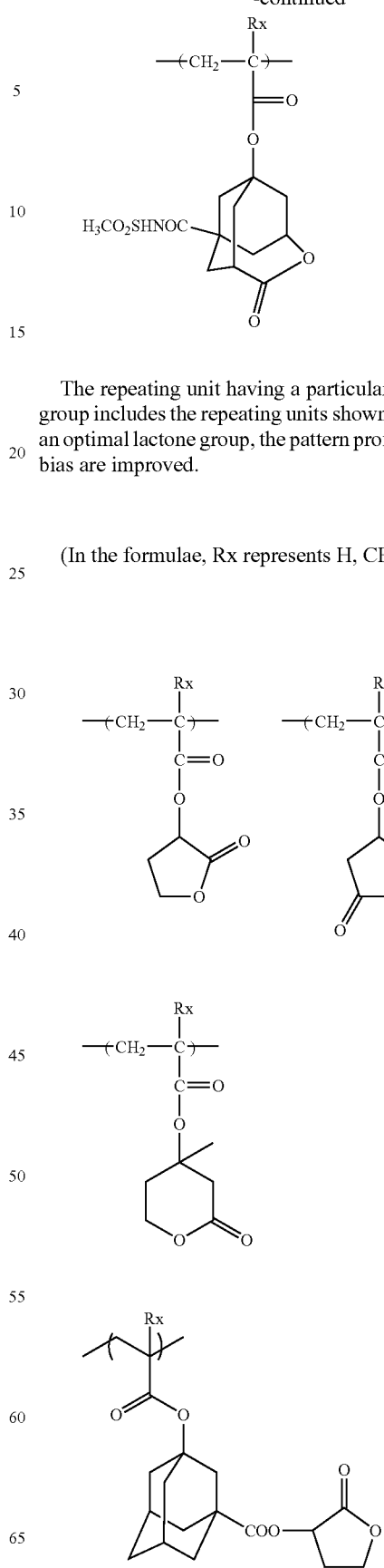
The repeating unit having a particularly preferred lactone group includes the repeating units shown below. By selecting an optimal lactone group, the pattern profile and the iso/dense bias are improved.
(In the formulae, Rx represents H, CH$_3$, CH$_2$OH or CF$_3$.)

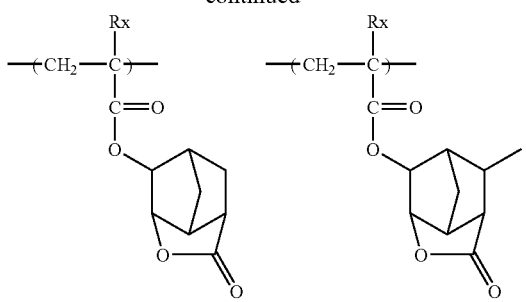
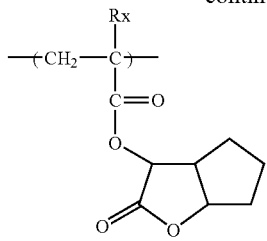
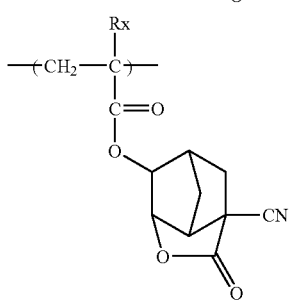
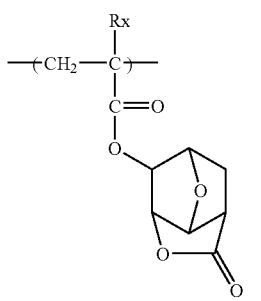
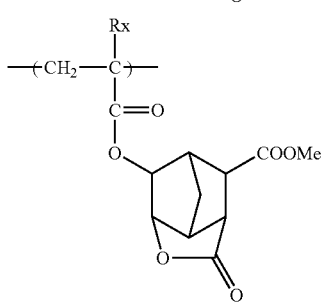
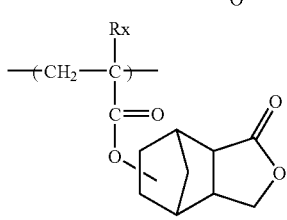
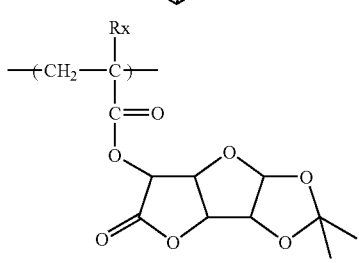

The resin of the component (A) preferably contains a repeating unit having a hydroxyl group or a cyano group. Thanks to this repeating unit, the adherence to substrate and the affinity for developer are enhanced. The repeating unit having a hydroxyl group or a cyano group is preferably a repeating unit having an alicyclic hydrocarbon structure substituted by a hydroxyl group or a cyano group. The alicyclic hydrocarbon structure in the alicyclic hydrocarbon structure substituted by a hydroxyl group or a cyano group is preferably an adamantyl group, a diamantyl group or a norbornene group. The alicyclic hydrocarbon structure substituted by a hydroxyl group or a cyano group is preferably a partial structure represented by the following formulae (VIIa) to (VIId):

(VIIa)

(VIIb)

(VIIc)

(VIId)

In formulae (VIIa) to (VIIc), each of $R_2c$ to $R_4c$ independently represents a hydrogen atom, a hydroxyl group or a cyano group, provided that at least one of $R_2c$ to $R_4c$ represents a hydroxyl group or a cyano group. A structure where one or two members out of $R_2c$ to $R_4c$ are a hydroxyl group with the remaining being a hydrogen atom is preferred. In formula (VIIa), it is more preferred that two members out of R₂c to R₄c are a hydroxyl group and the remaining is a hydrogen atom.

The repeating unit having a partial structure represented by formulae (VIIa) to (VIId) includes repeating units represented by the following formulae (AIIa) to (AIId):

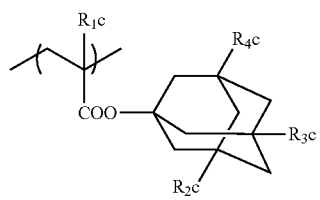
(AIIa)

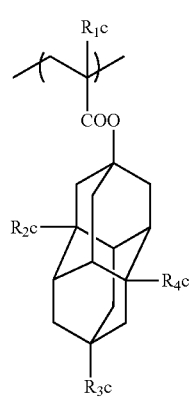
(AIIb)

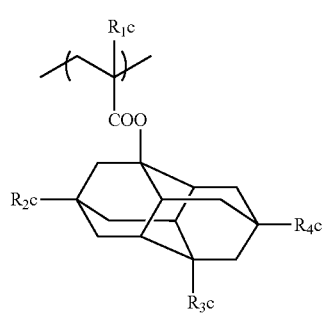
(AIIc)

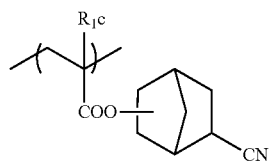
(AIId)

In formulae (AIIa) to (AIId), R₁c represents a hydrogen atom, a methyl group, a trifluoromethyl group or a hydroxymethyl group.

R₂c to R₄c have the same meanings as R₂c to R₄c in formulae (VIIa) to (VIIc).

The content of the repeating unit having an alicyclic hydrocarbon structure substituted by a hydroxyl group or a cyano group is preferably from 5 to 40 mol %, more preferably from 5 to 30 mol %, still more preferably from 10 to 25 mol %, based on all repeating units in the polymer.

Specific examples of the repeating unit having a hydroxyl group or a cyano group are set forth below, but the present invention is not limited thereto.

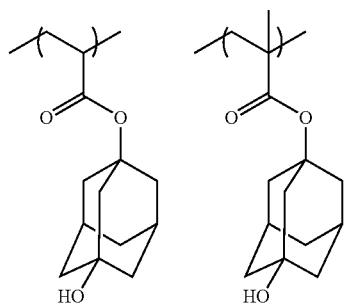

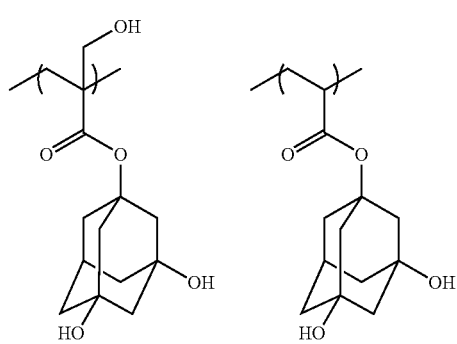

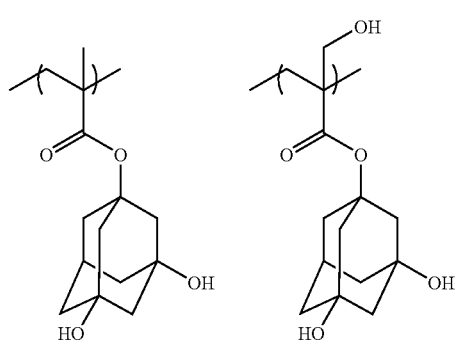

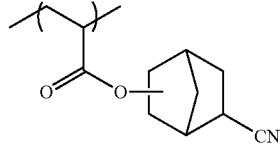

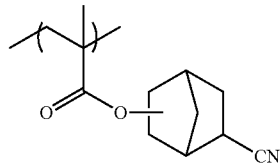

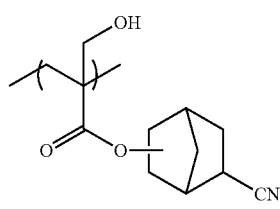

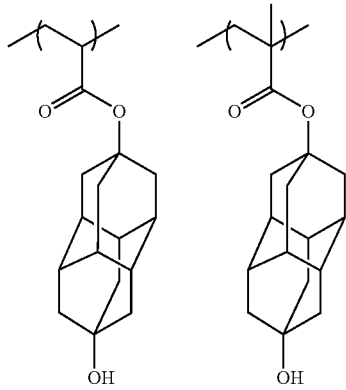

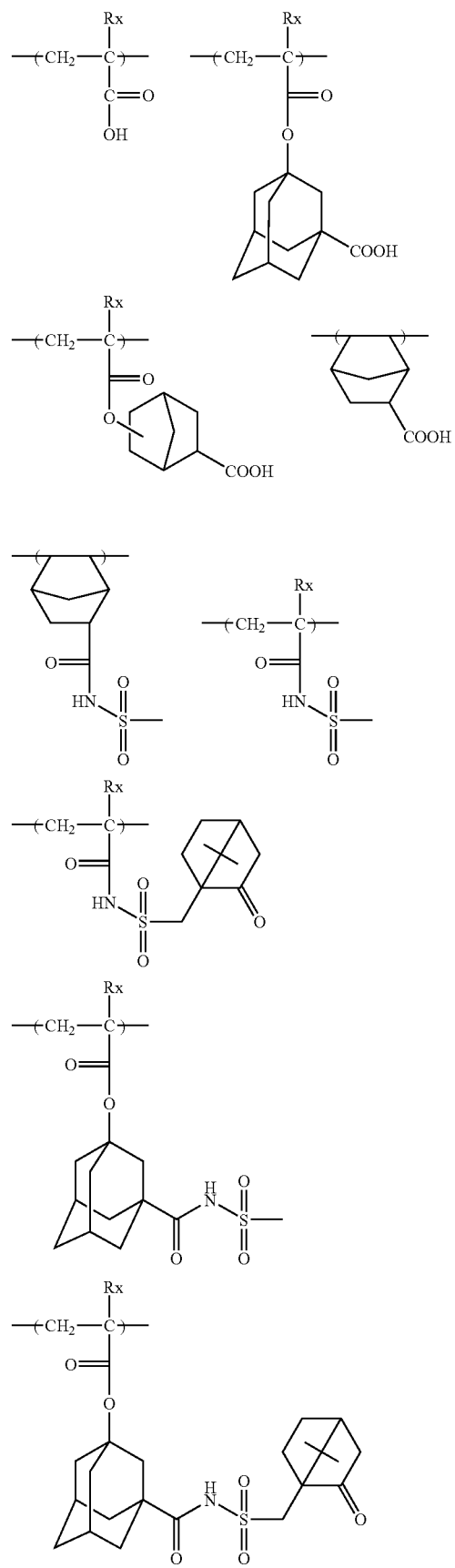

The resin of the component (A) preferably contains a repeating unit having an alkali-soluble group. The alkali-soluble group includes a carboxyl group, a sulfonamide group, a sulfonylimide group, a bisulfonylimide group, and an aliphatic alcohol with the α-position being substituted, by an electron-withdrawing group, such as hexafluoroisopropanol group. It is more preferred to contain a repeating unit having a carboxyl group. By virtue of containing a repeating unit having an alkali-soluble group, the resolution increases in the usage of forming contact holes. As for the repeating unit having an alkali-soluble group, all of a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the polymer chain terminal by using an alkali-soluble group-containing polymerization initiator or chain transfer agent at the polymerization, are preferred. The linking group may have a monocyclic or polycyclic hydrocarbon structure. Above all, a repeating unit by an acrylic acid or a methacrylic acid is preferred.

The content of the repeating unit having an alkali-soluble group is preferably from 0 to 20 mol %, more preferably from 3 to 15 mol %, still more preferably from 5 to 10 mol %, based on all repeating units in the polymer.

Specific examples of the repeating unit having an alkali-soluble group are set forth below, but the present invention is not limited thereto.

(In the formulae, Rx is H, $CH_3$, $CF_3$ or $CH_2OH$.)

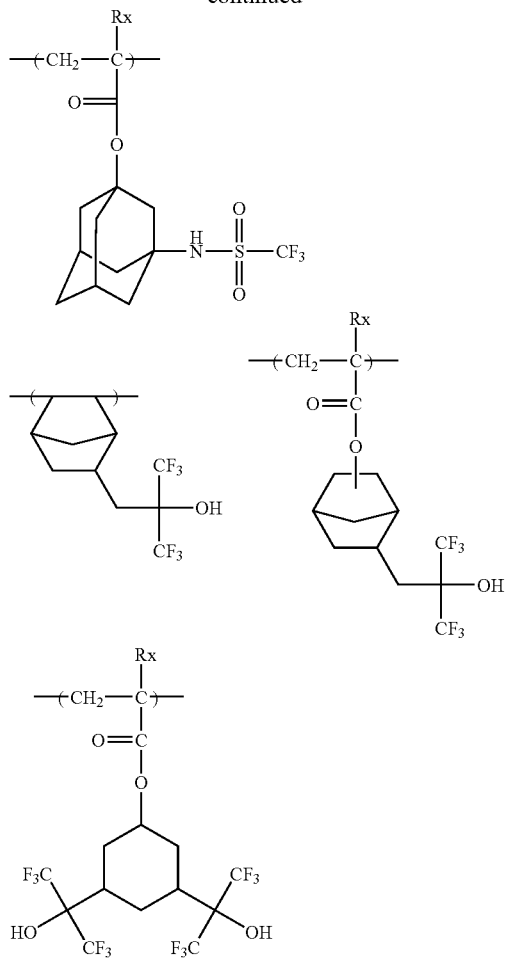

The repeating unit having at least one kind of a group selected from a lactone group, a hydroxyl group, a cyano group and an alkali-soluble group is preferably a repeating unit having at least two members selected from a lactone group, a hydroxyl group, a cyano group and an alkali-soluble group, more preferably a repeating unit having a cyano group and a lactone group. Above all, a repeating unit having a structure where a cyano group is substituted on the lactone structure of (LCI-4) is preferred.

The resin of the component (A) may further contain a repeating unit having an alicyclic hydrocarbon structure and not exhibiting acid decomposability. Thanks to such a repeating unit, the dissolving out of low molecular components from the resist film to the immersion liquid at the immersion exposure can be reduced. Examples of this repeating unit include a repeating unit composed of 1-adamantyl(meth) acrylate, diamantyl(meth)acrylate, tricyclodecanyl(meth) acrylate or cyclohexyl(meth)acrylate.

The resin of the component (A) may contain, in addition to the above-described repeating structural units, various repeating structural units for the purpose of controlling dry etching resistance, suitability for standard developer, adherence to substrate, resist profile and properties generally required of the resist, such as resolution, heat resistance and sensitivity.

Examples of such a repeating structural unit include, but are not limited to, repeating structural units corresponding to the monomers described below.

Thanks to such a repeating structural unit, the performance required of the resin of the component (A), particularly, (1) solubility in coating solvent, (2) film-forming property (glass transition point), (3) alkali developability, (4) film loss (selection of hydrophilic, hydrophobic or alkali-soluble group), (5) adherence of unexposed area to substrate, (6) dry etching resistance and the like, can be subtly controlled.

Examples of the monomer include a compound having one addition-polymerizable unsaturated bond selected from acrylic acid esters, methacrylic acid esters, acrylamides, methacrylamides, allyl compounds, vinyl ethers and vinyl esters.

Other than these, an addition-polymerizable unsaturated compound copolymerizable with the monomers corresponding to the above-described various repeating structural units may be copolymerized.

In the resin of the component (A), the molar ratio of respective repeating structural units contained is appropriately determined to control dry etching resistance of resist, suitability for standard developer, adherence to substrate, resist profile and performances generally required of the resist, such as resolution, heat resistance and sensitivity.

In the case where the photosensitive composition of the present invention is used for ArF exposure, the resin of the component (A) preferably has no aromatic group in view of transparency to ArF light.

The resin of the component (A) is preferably a resin where all repeating units are composed of a (meth)acrylate-based repeating unit. In this case, all repeating units may be a methacrylate-based repeating unit, all repeating units may be an acrylate-based repeating unit, or all repeating unit may be composed of a methacrylate-based repeating unit and an acrylate-based repeating unit, but the content of the acrylate-based repeating unit is preferably 50 mol % or less based on all repeating units. The resin is more preferably a copolymerized polymer containing from 20 to 50 mol % of an acid decomposable group-containing (meth)acrylate-based repeating unit represented by formula (AI), from 20 to 50 mol % of a lactone group-containing (meth)acrylate-based repeating unit, from 0 to 30 mol % of a (meth)acrylate-based repeating unit having an alicyclic hydrocarbon structure substituted by a hydroxyl group or a cyano group, and from 0 to 20 mol % of other (meth)acrylate-based repeating units.

In the case where the photosensitive composition of the present invention is irradiated with KrF excimer laser light, electron beam, X-ray or high-energy beam at a wavelength of 50 nm or less (e.g., EUV), the resin of the component (A) preferably further contains a hydroxystyrene-based repeating unit in addition to the repeating unit represented by formula (AI). The resin of the component (A) more preferably contains a hydroxystyrene-based repeating unit, a hydroxystyrene-based repeating unit protected by an acid-decomposable group, and an acid-decomposable repeating unit such as tertiary alkyl(meth)acrylate, Preferred examples of the repeating unit having an acid-decomposable group include a repeating unit composed of a tert-butoxycarbonyloxystyrene, a 1-alkoxyethoxystyrene and a tertiary alkyl(meth)acrylate. A repeating unit composed of a 2-alkyl-2-adamantyl(meth)acrylate or a dialkyl(1-adamantyl)methyl(meth)acrylate is more preferred.

The resin of the component (A) can be synthesized by an ordinary method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as tetrahydrofuran, 1,4-dioxane and diisopropyl ether, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate, propylene glycol monomethyl ether and cyclohexanone. The polymerization is more preferably performed using the same solvent as the solvent used in the photosensitive composition of the present invention. By the use of this solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The initiator is added additionally or in parts, if desired. After the completion of reaction, the reaction product is poured in a solvent, and the desired polymer is collected by a method such as powder or solid recovery. The reaction concentration is from 5 to 50 mass %, preferably from 10 to 30 mass %, and the reaction temperature is usually from 10 to 150° C., preferably from 30 to 120° C., more preferably from 60 to 100° C.

The content of the repeating unit corresponding to the compound represented by formula (I) is preferably from 1 to 60 mol %, more preferably from 1 to 50 mol %, still more preferably from 5 to 40 mol %, based on all repeating units in the polymer.

The weight average molecular weight of the resin of the component (A) is preferably from 1,000 to 200,000, more preferably from 2,000 to 20,000, still more preferably from 3,000 to 15,000, yet still more preferably from 3,000 to 10,000, in terms of polystyrene by the GPC method. When the weight average molecular weight is from 1,000 to 200,000, deterioration of heat resistance, dry etching resistance and developability can be avoided and the film-forming property can be prevented from deteriorating due to increase in the viscosity.

The polydispersity (molecular weight distribution) is usually from 1 to 3, preferably from 1 to 2, more preferably from 1.1 to 1.8. As the molecular weight distribution is smaller, the resolution and resist profile are more excellent, the side wall of the resist pattern is smoother, and the roughness is more improved.

In the photosensitive composition of the present invention, the amount of the resin of the component (A) blended in the entire composition is preferably from 0.1 to 99 mass %, more preferably from 0.2 to 50 mass %, based on the entire solid content of the resist composition.

The photosensitive composition of the present invention may also contain (A') a resin not containing a repeating unit corresponding to the compound represented by formula (I). By using the resin of the component (A) and the resin of the component (A') in combination, compatibility of respective components of the resin is enhanced and the number of coating defects is decreased. The resin of the component (A') which can be used in combination preferably contains various repeating structural units described above.

In the present invention, the (A') resin not containing a repeating unit corresponding to the compound represented by formula (I) is preferably a resin capable of increasing the solubility in an alkali developer by the action of an acid.

The resin of the component (A) or (A') preferably further contains an acid-decomposable repeating unit having a monocyclic or polycyclic alicyclic hydrocarbon structure.

The resin of the component (A) or (A') preferably further contains a repeating unit having a lactone structure, a repeating unit having a hydroxyl group or a cyano group, a repeating unit having a carboxyl group, a repeating unit having a hexafluoroisopropanol structure, and the like.

Furthermore, the resin preferably contains a dissolution inhibiting compound having a molecular weight of 3,000 or less and being capable of decomposing by the action of an acid to increase the solubility in an alkali developer.

In addition, the resin preferably contains a basic compound and at least one member selected from fluorine-containing and/or silicon-containing surfactants.

The basic compound is preferably a compound having a structure selected from an imidazole structure, a diazabicyclo structure, an onium hydroxide structure, an onium carboxylate structure, a trialkylamine structure, an aniline structure and a pyridine structure, an alkylamine derivative having a hydroxyl group and/or an ether bond, or an aniline derivative having a hydroxyl group and/or an ether bond.

In the case where the photosensitive composition of the present invention is used for ArF exposure, the resin of the component (A') also preferably has no aromatic group in view of transparency to ArF light.

In view of compatibility with the hydrophobic resin (HR), the resin (A) or (A') for use in the present invention preferably contains no fluorine atom and no silicon atom.

The weight average molecular weight of the resin of the component (A') is preferably from 1,000 to 200,000, more preferably from 2,000 to 20,000, still more preferably from 3,000 to 15,000, yet still more preferably from 3,000 to 10,000, in terms of polystyrene by the GPC method. When the weight average molecular weight is from 1,000 to 200,000, deterioration of heat resistance, dry etching resistance and developability can be avoided and the film-forming property can be prevented from deteriorating due to increase in the viscosity.

The polydispersity (molecular weight distribution) is usually from 1 to 3, preferably from 1 to 2, more preferably from 1.4 to 1.7. As the molecular weight distribution is smaller, the resolution and resist profile are more excellent, the side wall of the resist pattern is smoother, and the roughness is more improved.

In the photosensitive composition of the present invention, the amount of the resin of the component (A') blended in the entire composition is preferably from 50 to 99.99 mass %, more preferably from 60 to 99.0 mass %, based on the entire solid content.

In the present invention, as for the resin of the component (A'), one kind may be used or a plurality of kinds may be used in combination.

Also, in the photosensitive composition of the present invention, the ratio between the resin of the component (A) and the resin of the component (A') is, in terms of the ratio by mass, usually from 1:99 to 50:50, preferably from 5:95 to 40:60.

(B) Compound Capable of Generating an Acid Upon Irradiation with an Actinic Ray or Radiation The positive resist composition of the present invention contains a compound capable of generating an acid upon irradiation with an actinic ray or radiation (hereinafter sometimes referred to as an "acid generator").

The acid generator which can be used may be appropriately selected from a photo-initiator for cationic photopolymerization, a photo-initiator for radical photopolymerization, a photo-decoloring agent for dyes, a photo-discoloring agent, a compound known to generate an acid upon irradiation with an actinic ray or radiation and used for microresist or the like, and a mixture thereof.

Examples of such a compound include a diazonium salt, a phosphonium salt, a sulfonium salt, an iodonium salt, imidosulfonate, oxime sulfonate, diazodisulfone, disulfone and o-nitrobenzyl sulfonate.

Also, a compound where such a group or compound capable of generating an acid upon irradiation with an actinic ray or radiation is introduced into the main or side chain of the polymer, for example, compounds described in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029, may be used.

Furthermore, compounds capable of generating an acid by the effect of light described, for example, in U.S. Pat. No. 3,779,778 and European Patent 126,712 may also be used.

Out of the acid generators, preferred compounds are compounds represented by the following formulae (ZI), (ZII) and (ZIII):

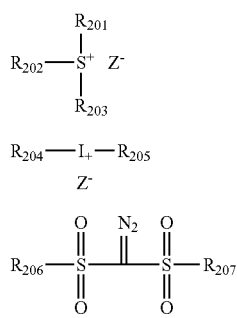

In formula (ZI), each of $R_{201}$, $R_{202}$ and $R_{203}$ independently represents an organic group.

The carbon number of the organic group as $R_{201}$, $R_{202}$ and $R_{203}$ is generally from 1 to 30, preferably from 1 to 20.

Two members out of $R_{201}$ to $R_{203}$ may combine with each other to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

$Z^-$ represents a non-nucleophilic anion.

Examples of the non-nucleophilic anion as $Z^-$ include a sulfonate anion, a carboxylate anion, a sulfonylimide anion, a bis(alkylsulfonyl)imide anion and a tris(alkylsulfonyl)methyl anion.

The non-nucleophilic anion is an anion having an extremely low ability of causing a nucleophilic reaction, and this anion can suppress the decomposition with aging due to an intramolecular nucleophilic reaction. Thanks to this anion, the aging stability of the resist is enhanced.

Examples of the sulfonate anion include an aliphatic sulfonate anion, an aromatic sulfonate anion and a camphorsulfonate anion.

Examples of the carboxylate anion include an aliphatic carboxylate anion, an aromatic carboxylate anion and an aralkylcarboxylate anion.

The aliphatic moiety in the aliphatic sulfonate anion may be an alkyl group or a cycloalkyl group but is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a bornyl group.

The aromatic group in the aromatic sulfonate anion is preferably an aryl group having a carbon number of 6 to 14, and examples thereof include a phenyl group, a tolyl group and a naphthyl group.

The alkyl group, cycloalkyl group and aryl group in the aliphatic sulfonate anion and aromatic sulfonate anion may have a substituent. Examples of the substituent of the alkyl group, cycloalkyl group and aryl group in the aliphatic sulfonate anion and aromatic sulfonate anion include a nitro group, a halogen atom (e.g., fluorine, chlorine, bromine, iodine), a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), an alkylthio group (preferably having a carbon number of 1 to 15), an alkylsulfonyl group (preferably having a carbon number of 1 to 15), an alkyliminosulfonyl group (preferably having a carbon number of 2 to 15), an aryloxysulfonyl group (preferably having a carbon number of 6 to 20), an alkylaryloxysulfonyl group (preferably having a carbon number of 7 to 20), a cycloalkylaryloxysulfonyl group (preferably having a carbon number of 10 to 20), an alkyloxyalkyloxy group (preferably having a carbon number of 5 to 20), and a cycloalkylalkyloxyalkyloxy group (preferably having a carbon number of 8 to 20). As for the aryl group or ring structure in each group, examples of the substituent further include an alkyl group (preferably having a carbon number of 1 to 15).

Examples of the aliphatic moiety in the aliphatic carboxylate anion include the same alkyl groups and cycloalkyl groups as those in the aliphatic sulfonate anion.

Examples of the aromatic group in the aromatic carboxylate anion include the same aryl groups as those in the aromatic sulfonate anion.

The aralkyl group in the aralkylcarboxylate anion is preferably an aralkyl group having a carbon number of 6 to 12, and examples thereof include a benzyl group, a phenethyl group, a naphthylmethyl group, a naphthylethyl group and a naphthylbutyl group.

The alkyl group, cycloalkyl group, aryl group and aralkyl group in the aliphatic carboxylate anion, aromatic carboxylate anion and aralkylcarboxylate anion may have a substituent. Examples of the substituent of the alkyl group, cycloalkyl group, aryl group and aralkyl group in the aliphatic carboxylate anion, aromatic carboxylate anion and aralkylcarboxylate anion include the same halogen atoms, alkyl groups, cycloalkyl groups, alkoxy groups and alkylthio groups as those in the aromatic sulfonate anion.

Examples of the sulfonylimide anion include saccharin anion.

The alkyl group in the bis(alkylsulfonyl)imide anion and tris(alkylsulfonyl)methyl anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. Examples of the substituent of such an alkyl group include a halogen atom, a halogen atom-substituted alkyl group, an alkoxy group, an alkylthio group, an alkyloxysulfonyl group, an aryloxysulfonyl group and a cycloalkylaryloxysulfonyl group, with a fluorine atom-substituted alkyl group being preferred.

Other examples of the non-nucleophilic anion include fluorinated phosphorus, fluorinated boron and fluorinated antimony.

The non-nucleophilic anion of $Z^-$ is preferably an aliphatic sulfonate anion substituted by a fluorine atom at the α-position of the sulfonic acid, an aromatic sulfonate anion substituted by a fluorine atom or a fluorine atom-containing group, a bis(alkylsulfonyl)imide anion with the alkyl group being substituted by a fluorine atom, or a tris(alkylsulfonyl)methide anion with the alkyl group being substituted by a fluorine atom. The non-nucleophilic anion is more preferably a perfluoroaliphatic sulfonate anion having a carbon number of 4 to 8 or a benzenesulfonate anion having a fluorine atom, still more preferably nonafluorobutanesulfonate anion, perfluorooctanesulfonate anion, pentafluorobenzenesulfonate anion or 3,5-bis(trifluoromethyl)benzenesulfonate anion.

Examples of the organic group as $R_{201}$, $R_{202}$ and $R_{203}$ include the corresponding groups in the compounds (ZI-1), (ZI-2) and (ZI-3) described later.

The compound may be a compound having a plurality of structures represented by formula (ZI), for example, a compound having a structure where at least one of $R_{201}$ to $R_{203}$ in the compound represented by formula (ZI) is bonded to at least one of $R_{201}$ to $R_{203}$ in another compound represented by formula (ZI).

The component (ZI) is more preferably a compound (ZI-1), (ZI-2) or (ZI-3) described below.

The compound (ZI-1) is an arylsulfonium compound where at least one of $R_{201}$ to $R_{203}$ in formula (ZI) is an aryl group, that is, a compound having arylsulfonium as the cation.

In the arylsulfonium compound, all of $R_{201}$ to $R_{203}$ may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound and an aryldicycloalkylsulfonium compound.

The aryl group in the arylsulfonium compound is preferably a phenyl group or a naphthyl group, more preferably a phenyl group. The aryl group may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene). In the case where the arylsulfonium compound has two or more aryl groups, these two or more aryl groups may be the same or different.

The alkyl or cycloalkyl group which is present, if desired, in the arylsulfonium, compound is preferably a linear or branched alkyl group having a carbon number of 1 to 15 or a cycloalkyl group having a carbon number of 3 to 15, and examples thereof include a methyl group, an ethyl group, a propyl group, an n-butyl group, a sec-butyl group, a tert-butyl group, a cyclopropyl group, a cyclobutyl group and a cyclohexyl group.

The aryl group, alkyl group and cycloalkyl group of $R_{201}$ to $R_{203}$ may have, as the substituent, an alkyl group (for example, having a carbon number of 1 to 15), a cycloalkyl group (for example, having a carbon number of 3 to 15), an aryl group (for example, having a carbon number of 6 to 14), an alkoxy group (for example, having a carbon number of 1 to 15), a halogen atom, a hydroxyl group or a phenylthio group. The substituent is preferably a linear or branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4, or an alkoxy group having a carbon number of 1 to 4. The substituent may be substituted on any one of three members $R_{201}$ to $R_{203}$ or may be substituted on all of these three members. In the case where $R_{201}$ to $R_{203}$ are an aryl group, the substituent is preferably substituted at the p-position of the aryl group.

The compound (ZI-2) is described below.

The compound (ZI-2) is a compound where each of $R_{201}$ to $R_{203}$ in formula (ZI) independently represents an aromatic ring-free organic group. The aromatic ring as used herein includes an aromatic ring containing a heteroatom.

The aromatic ring-free organic group as $R_{201}$ to $R_{203}$ has a carbon number of generally from 1 to 30, preferably from 1 to 20.

Each of $R_{201}$ to $R_{203}$ independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, still more preferably a linear or branched 2-oxoalkyl group.

The alkyl group and cycloalkyl group of $R_{201}$ to $R_{203}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl). The alkyl group is more preferably a 2-oxoalkyl group or an alkoxycarbonylmethyl group. The cycloalkyl group is more preferably a 2-oxocycloalkyl group.

The 2-oxoalkyl group may be either linear or branched and is preferably a group having >C=O at the 2-position of the above-described alkyl group.

The 2-oxocycloalkyl group is preferably a group having >C=O at the 2-position of the above-described cycloalkyl group.

The alkoxy group in the alkoxycarbonylmethyl group is preferably an alkoxy group having a carbon number of 1 to 5 (e.g., methoxy, ethoxy, propoxy, butoxy, pentoxy).

$R_{201}$ to $R_{203}$ may be further substituted by a halogen atom, an alkoxy group (for example, having a carbon number of 1 to 5), a hydroxyl group, a cyano group or a nitro group.

The compound (ZI-3) is a compound represented by the following formula (ZI-3), and this is a compound having a phenacylsulfonium salt structure.

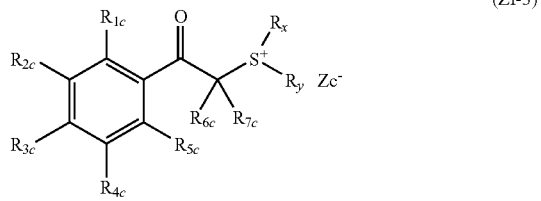

(ZI-3)

In formula (ZI-3), each of $R_{1c}$ to $R_{5c}$ independently represents a hydrogen atom, an alkyl group, a cycloalkyl group, an alkoxy group or a halogen atom.

Each of $R_{6c}$ and $R_{7c}$ independently represents a hydrogen atom, an alkyl group or a cycloalkyl group.

Each of $R_x$ and $R_y$ independently represents an alkyl group, a cycloalkyl group, an allyl group or a vinyl group.

Any two or more members out of $R_{1c}$ to $R_{5c}$, a pair of $R_{6c}$ and $R_{7c}$, or a pair of $R_x$ and $R_y$ may combine together to form a ring structure. This ring structure may contain an oxygen atom, a sulfur atom, an ester bond or an amide bond. Examples of the group formed by combining any two or more members out of $R_{1c}$ to $R_{5c}$, a pair of $R_{6c}$ and $R_{7c}$, or a pair of $R_x$ and $R_y$ include a butylene group and a pentylene group.

$Zc^-$ represents a non-nucleophilic anion, and examples thereof are the same as those of the non-nucleophilic anion of $Z^-$ in formula (ZI).

The alkyl group as $R_{1c}$ to $R_{7c}$ may be either linear or branched and is, for example, an alkyl group having a carbon number of 1 to 20, preferably a linear or branched alkyl group having a carbon number of 1 to 12 (e.g., methyl, ethyl, linear or branched propyl, linear or branched butyl, linear or branched pentyl). The cycloalkyl group is, for example, a cycloalkyl group having a carbon number of 3 to 8 (e.g., cyclopentyl, cyclohexyl).

The alkoxy group as $R_{1c}$ to $R_{5c}$ may be linear, branched or cyclic and is, for example, an alkoxy group having a carbon number of 1 to 10, preferably a linear or branched alkoxy group having a carbon number of 1 to 5 methoxy, ethoxy, linear or branched propoxy, linear or branched butoxy, linear or branched pentoxy) or a cyclic alkoxy group having a carbon number of 3 to 8 (e.g., cyclopentyloxy, cyclohexyloxy).

A compound where any one of $R_{1c}$ to $R_{5c}$ is a linear or branched alkyl group, a cycloalkyl group or a linear, branched or cyclic alkoxy group is preferred, and a compound where the sum of carbon numbers of $R_{1c}$ to $R_{5c}$ is from 2 to 15 is more preferred. Thanks to such a compound, the solvent solubility is more enhanced and production of particles during storage can be suppressed.

Examples of the alkyl group and cycloalkyl group as $R_x$ and $R_y$ are the same as those of the alkyl group and cycloalkyl group in $R_{1c}$ to $R_{7c}$. Among these, a 2-oxoalkyl group, a 2-oxocycloalkyl group and an alkoxycarbonylmethyl group are preferred.

Examples of the 2-oxoalkyl group and 2-oxocycloalkyl group include a group having >C=O at the 2-position of the alkyl group or cycloalkyl group as $R_{1c}$ to $R_{7c}$.

Examples of the alkoxy group in the alkoxycarbonylmethyl group are the same as those of the alkoxy group in $R_{1c}$ to $R_{5c}$.

Each of $R_x$ and $R_y$ is preferably an alkyl or cycloalkyl group having a carbon number of 4 or more, more preferably 6 or more, still more preferably 8 or more.

In formulae (ZII) and (ZIII), each of $R_{204}$ to $R_{207}$ independently represents an aryl group, an alkyl group or a cycloalkyl group.

The aryl group of $R_{204}$ to $R_{207}$ is preferably a phenyl group or a naphthyl group, more preferably a phenyl group. The aryl group of $R_{204}$ to $R_{207}$ may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene).

The alkyl group and cycloalkyl group in $R_{204}$ to $R_{207}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl).

The aryl group, alkyl group and cycloalkyl group of $R_{204}$ to $R_{207}$ may have a substituent. Examples of the substituent which the aryl group, alkyl group and cycloalkyl group of $R_{204}$ to $R_{207}$ may have include an alkyl group (for example, having a carbon number of 1 to 15), a cycloalkyl group (for example, having a carbon number of 3 to 15), an aryl group (for example, having a carbon number of 6 to 15), an alkoxy group (for example, having a carbon number of 1 to 15), a halogen atom, a hydroxyl group and a phenylthio group.

$Z^-$ represents a non-nucleophilic anion, and examples thereof are the same as those of the non-nucleophilic anion of $Z^-$ in formula (ZI).

Other examples of the acid generator include compounds represented by the following formulae (ZIV), (ZV) and (ZVI):

ZIV

ZV

ZVI

In formulae (ZIV) to (ZVI), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Among the acid generators, more preferred are the compounds represented by formulae (ZI) to (ZIII).

The acid generator is preferably a compound that generates an acid having one sulfonic acid group or imide group, more preferably a compound that generates a monovalent perfluoroalkanesulfonic acid, a compound that generates an aromatic sulfonic acid substituted by a monovalent fluorine atom or a fluorine atom-containing group, or a compound that generates an imide acid substituted by a monovalent fluorine atom or a fluorine atom-containing group, still more preferably a sulfonium salt of fluoro-substituted alkanesulfonic acid, fluorine-substituted benzenesulfonic acid, fluorine-substituted imide acid or fluorine-substituted methide acid. In particular, the acid generator which can be used is preferably a compound that generates a fluoro-substituted alkanesulfonic acid, a fluoro-substituted benzenesulfonic acid or a fluoro-substituted imide acid, where pKa of the acid generated is pKa=−1 or less, and in this case, the sensitivity can be enhanced.

Out of the acid generators, particularly preferred examples are set forth below.

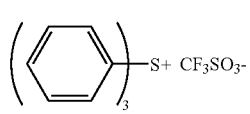
(z1)

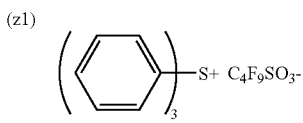
(z2)

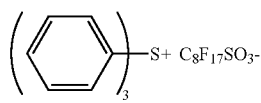
(z3)

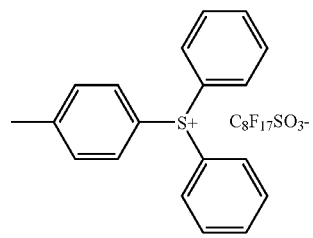
(z4)

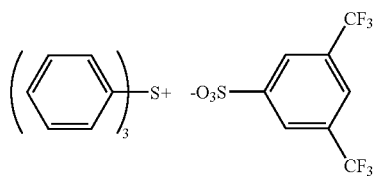
(z5)

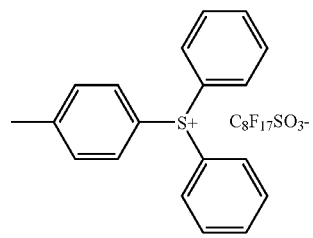
(z6)

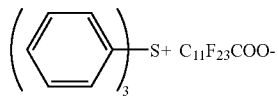
(z7)

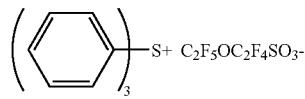
(z8)

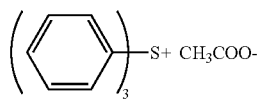
(z9)

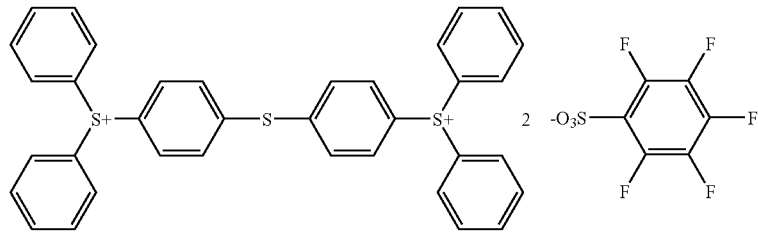
(z10)

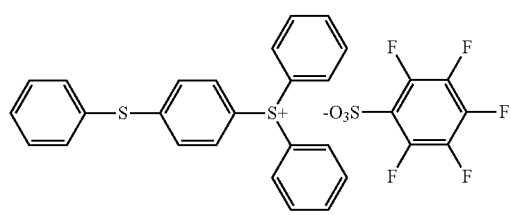
(z11)

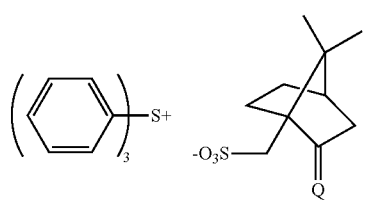
(z12)

-continued

-continued
(z29) 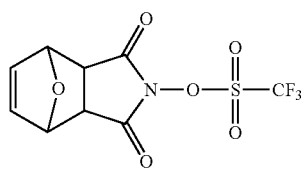
(z30) 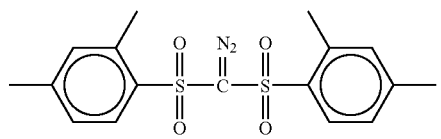
(z31) 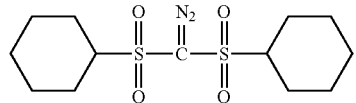
(z32) 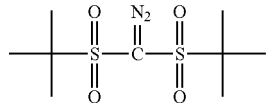
(z33) 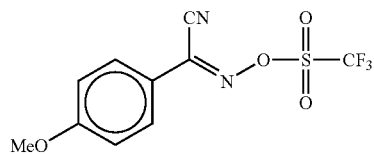
(z34) 
(z35) 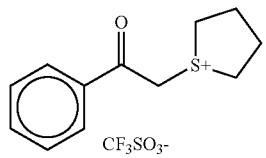
(z36) 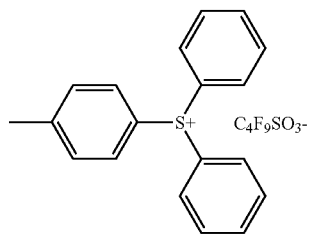
(z37) 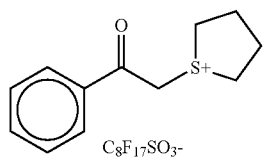
(z38) 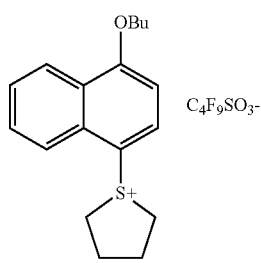
(z39) 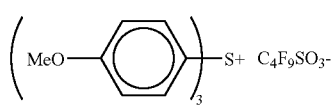
(z40) 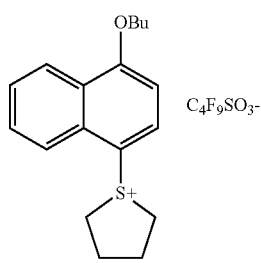
(z41) 
(z42) 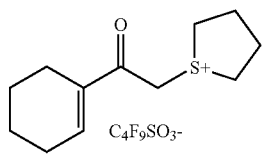

-continued
(z43) 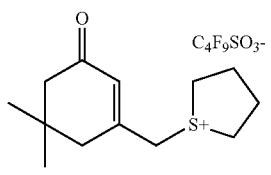
(z44) 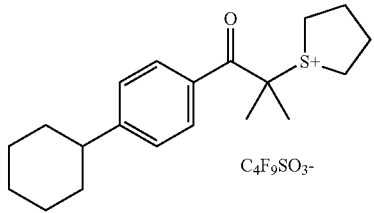
(z45) 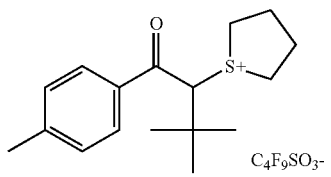
(z46) 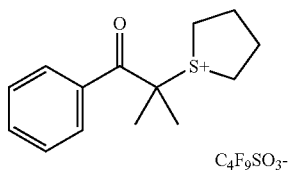
(z47) 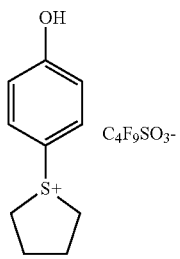
(z48) 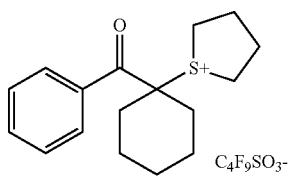
(z49) 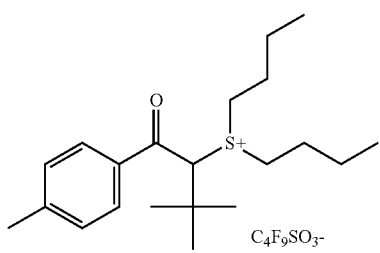
(z50) 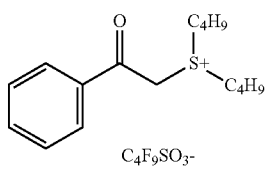
(z51) 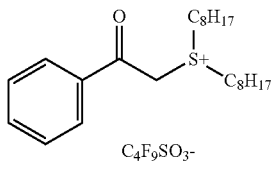
(z52) 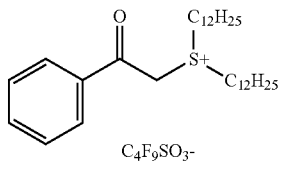
(z53) 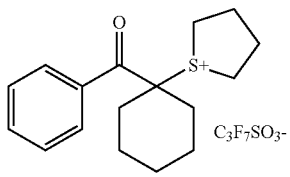
(z54) 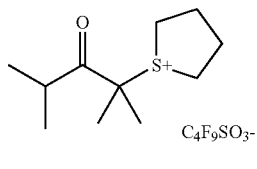
(z55) 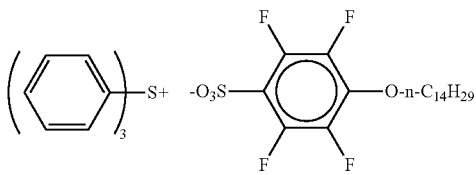
(z56) 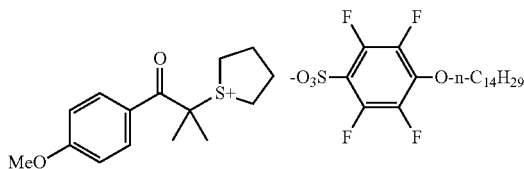

-continued
(z57) 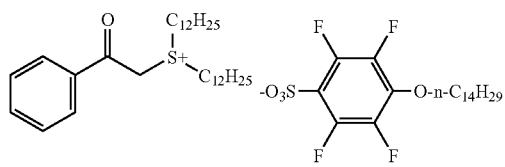
(z58) 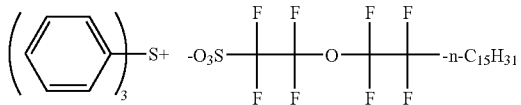
(z59) 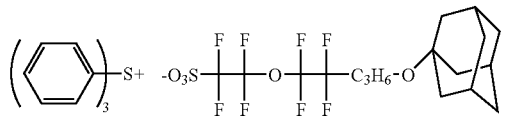
(z60) 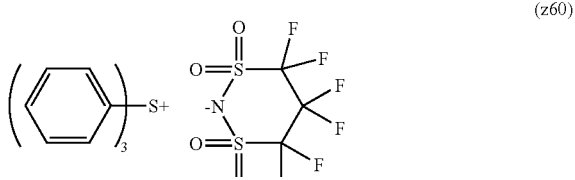
(z61) 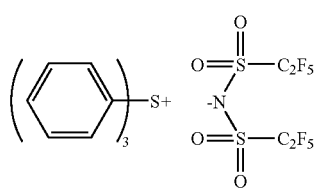
(z62) 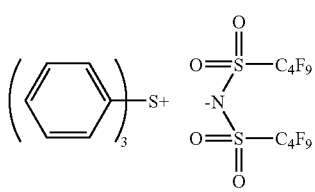
(z63) 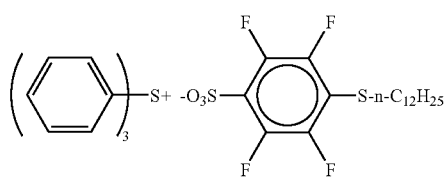
(z64) 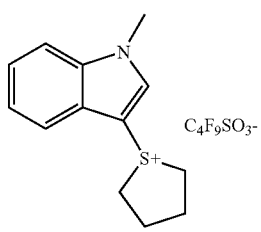
(x65) 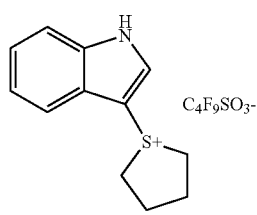
(z66) 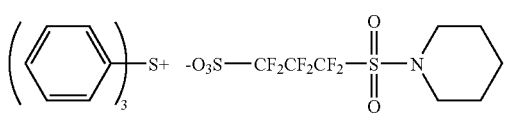
(z67) 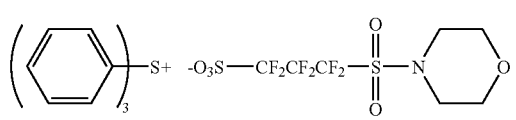
(z68) 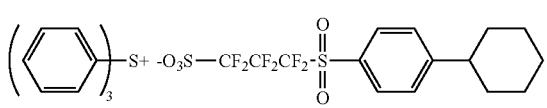
(z69) 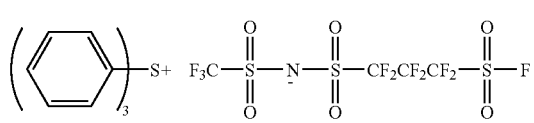
(z70) 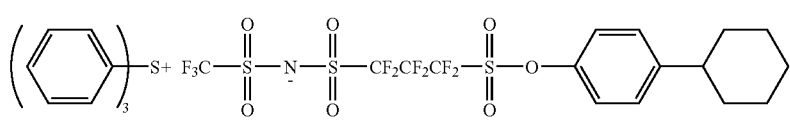
(z71) 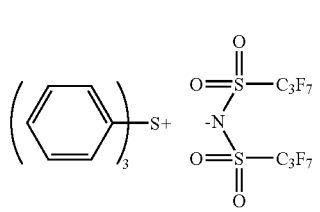
(z72) 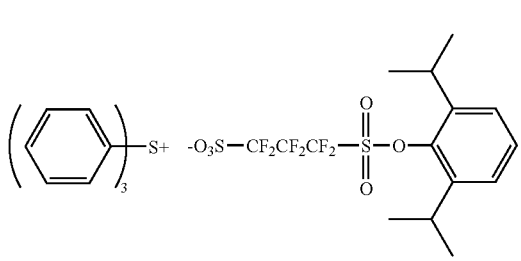

-continued

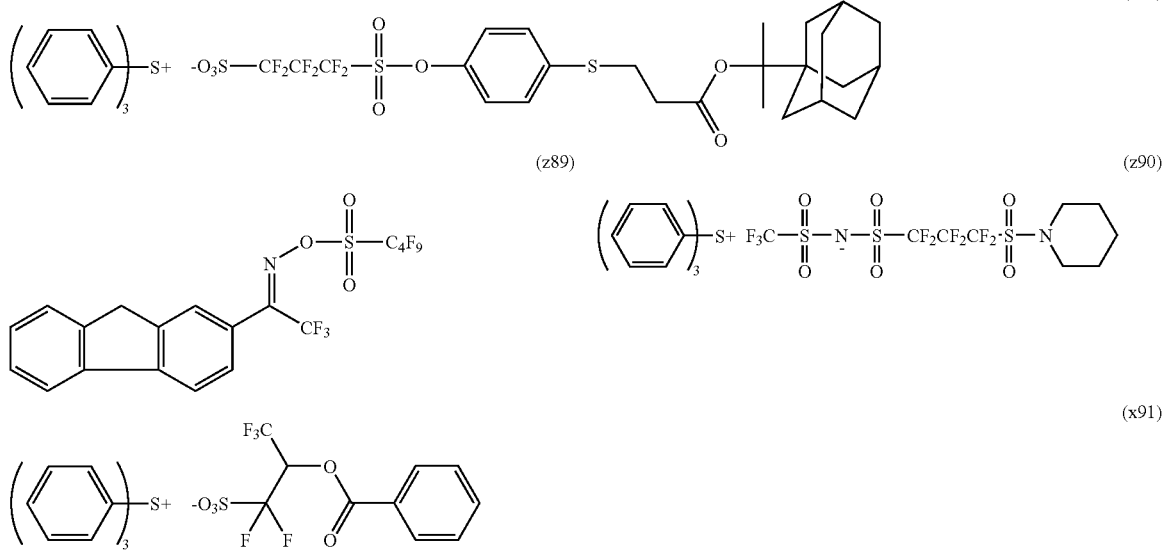

As for the acid generator, one kind may be used alone, or two or more kinds may be used in combination.

The content of the acid generator in the positive resist composition is preferably from 0.1 to 20 mass %, more preferably from 0.5 to 10 mass %, still more preferably from 1 to 7 mass %, based on the entire solid content of the positive resist composition.

(C) Compound Represented by Formula (II), Which Decomposes by the Action of an Acid to Generate an Acid The photosensitive composition of the present invention preferably contains a compound represented by the following formula (II), which decomposes by the action of an acid to generate an acid (hereinafter sometimes referred to as an "acid-increasing agent" or a "compound (C)").

Formula (II):

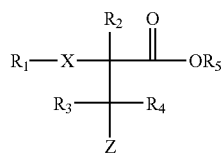

In formula (II), $R_1$ represents an alkyl group, a cycloalkyl group, an alkoxy group, an aryl group or an aryloxy group.

$R_2$ represents an alkyl group or a cycloalkyl group.

$R_1$ and $R_2$ may combine with each other to form a monocyclic or polycyclic hydrocarbon structure.

Each of $R_3$ and $R_4$ independently represents a hydrogen atom or an alkyl group.

$R_5$ represents a group capable of leaving by the action of an acid.

X represents —$SO_2$—, —SO— or —CO—.

Z represents a residue of an organic acid represented by ZH.

In formula (II), the alkyl group of $R_1$, $R_2$, $R_3$ and $R_4$ is preferably an alkyl group having a carbon number of 1 to 8, and examples thereof include a methyl group, an ethyl group, a propyl group, an isopropyl group, a butyl group and an octyl group.

The cycloalkyl group of $R_1$ and $R_2$ is preferably a cycloalkyl group having a carbon number of 4 to 10, and specific examples thereof include a cyclopropyl group, a cyclopentyl group, a cyclohexyl group, a cycloheptyl group, an adamantyl group, a boronyl group, an isoboronyl group, a tricyclodecanyl group, a dicyclopentenyl group, a norbornene epoxy group, a menthyl group, an isomenthyl group, a neomenthyl group and a tetracyclododecanyl group.

The alkoxy group of $R_1$ is preferably a linear or branched alkoxy group having a carbon number of 1 to 30, and examples thereof include a methoxy group, an ethoxy group, a propoxy group, an isopropoxy group, an n-butoxy group, an isobutoxy group, a sec-butoxy group, a tert-butoxy group, a hexyloxy group, a heptyloxy group, an octyloxy group, a nonyloxy group, a decyloxy group, an undecyloxy group and a dodecyloxy group.

The aryl group $R_1$ is preferably an aryl group having a carbon number of 6 to 14, and specific examples thereof include a phenyl group and a naphthyl group.

The aryloxy group of $R_1$ is preferably an aryloxy group having a carbon number of 6 to 20, and examples thereof include a phenoxy group.

The monocyclic or polycyclic hydrocarbon structure formed by combining $R_1$ and $R_2$ is preferably a cyclic hydrocarbon structure having a carbon number of 3 to 15, and examples thereof include a cyclic hydrocarbon structure having an oxo group, such as cyclopentanone structure, cyclohexanone structure, norbornanone structure and adamantanone structure, Each of these groups may further have a substituent. Examples of the substituent which each of these groups may have include a halogen atom, a hydroxyl group, a nitro group, a cyano group, a carboxyl group, a cycloalkyl group (preferably having a carbon number of 3 to 20), an aryl group (preferably having a carbon number of 6 to 14), an alkoxy group (preferably having a carbon number of 1 to 20), an acyl group (preferably having a carbon number of 2 to 20) and an acyloxy group (preferably having a carbon number of 2 to 20). As for the group having a cyclic structure, such as cycloalkyl group and aryl group, examples of the substituent further include an alkyl group (preferably having a carbon number of 1 to 20).

Examples of the group capable of leaving by the action of an acid of $R_5$ include groups represented by the following formulae (pI) to (pV), and a group having a monocyclic or polycyclic alicyclic hydrocarbon structure is preferred.

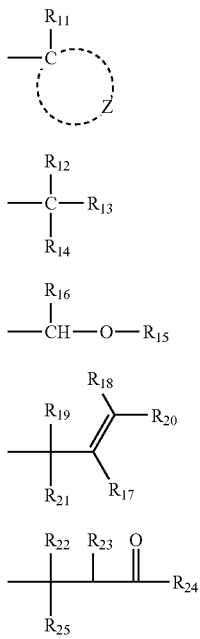

In formulae (pI) to (pV), $R_{11}$ represents an alkyl group.

Z represents an atomic group necessary for forming a cycloalkyl group together with the carbon atom.

Each of $R_{12}$ to $R_{14}$ independently represents an alkyl group or a cycloalkyl group. At least one of $R_{12}$ to $R_{14}$ is preferably a cycloalkyl group.

Each of $R_{15}$ and $R_{16}$ independently represents an alkyl group or a cycloalkyl group. At least one of $R_{15}$ and $R_{16}$ is preferably a cycloalkyl group.

Each of $R_{17}$ to $R_{21}$ independently represents a hydrogen atom, an alkyl group or a cycloalkyl group, provided that any one of $R_{19}$ and $R_{21}$ represents an alkyl group or a cycloalkyl group. At least one of $R_{17}$ to $R_{21}$ is preferably a cycloalkyl group.

Each of $R_{22}$ to $R_{25}$ independently represents a hydrogen atom, an alkyl group or a cycloalkyl group. $R_{23}$ and $R_{24}$ may combine with each other to form a ring. At least one of $R_{22}$ to $R_{25}$ is preferably a cycloalkyl group.

In formulae (pI) to (pV), the alkyl group of $R_{11}$ to $R_{25}$ is preferably a linear or branched alkyl group having a carbon number of 1 to 4, and examples thereof include a methyl group, an ethyl group, an n-propyl group, an isopropyl group, an n-butyl group, an isobutyl group and a sec-butyl group.

The cycloalkyl group of $R_{12}$ to $R_{25}$ and the cycloalkyl group formed by Z together with the carbon atom may be monocyclic or polycyclic. Specific examples thereof include a group having a carbon number of 5 or more and having a monocyclo, bicyclo, tricyclo or tetracyclo structure or the like. The carbon number thereof is preferably from 6 to 30, more preferably from 7 to 25.

Preferred examples of the cycloalkyl group include an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. Among these, more preferred are an adamantyl group, a norbornyl group, a cyclohexyl group, a cyclopentyl group, a tetracyclododecanyl group and a tricyclodecanyl group.

The alkyl group and the cycloalkyl group may further have a substituent. Examples of the substituent which the alkyl group and the cycloalkyl group may further have include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). Examples of the substituent which these alkyl group, alkoxy group, alkoxycarbonyl group and the like may further have include a hydroxyl group, a halogen atom and an alkoxy group.

The organic acid of ZH is preferably a sulfonic acid, a carboxylic acid, an imide acid or a methide acid.

Z is preferably a group represented by the following structural formulae:

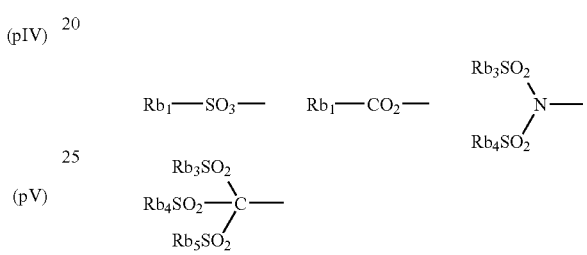

In the structural formulae above, $Rb_1$ represents an organic group. The organic group of $Rb_1$ is preferably an organic group having a carbon number of 1 to 30, and examples thereof include an alkyl group, a cycloalkyl group, an aryl group, and a group formed by connecting a plurality of these groups through a single bond or a linking group such as $-O-$, $-CO_2-$, $-S-$, $-SO_3-$ and $-SO_2N(Rc_1)-$. In the formula, $Rc_1$ represents a hydrogen atom or an alkyl group.

Each of $Rb_3$, $Rb_4$ and $Rb_5$ independently represents an organic group. Examples of the organic group of $Rb_3$, $Rb_4$ and $Rb_5$ are the same as those of the organic group of $Rb_1$. Above all, a perfluoroalkyl group having a carbon number of 1 to 4 is preferred.

$Rb_3$ and $Rb_4$ may combine with each other to form a ring. The group formed by combining $Rb_3$ and $Rb_4$ includes an alkylene group and an arylene group and is preferably a perfluoroalkylene group having a carbon number of 2 to 4.

The organic group of $Rb_1$ and $Rb_3$ to $Rb_5$ is preferably an alkyl group with the 1-position being substituted by a fluorine atom or a fluoroalkyl group, or a phenyl group substituted by a fluorine atom or a fluoroalkyl group. By virtue of having a fluorine atom or a fluoroalkyl group, the acidity of the acid generated upon irradiation with light rises and the sensitivity is enhanced.

Formula (II) is preferably the following formula (Ia) or (Ib):

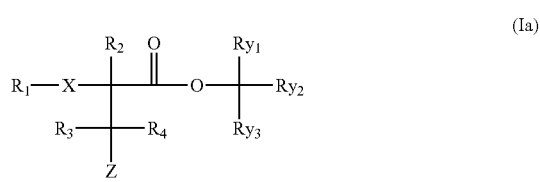

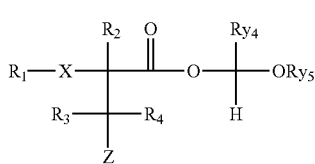

(Ib)

In formulae (Ia) and (Ib), $R_1$ represents an alkyl group, a cycloalkyl group, an alkoxy group, an aryl group or an aryloxy group.

$R_2$ represents an alkyl group or a cycloalkyl group.

$R_1$ and $R_2$ may combine with each other to form a monocyclic or polycyclic hydrocarbon structure.

Each of $R_3$ and $R_4$ independently represents a hydrogen atom or an alkyl group.

X represents —$SO_2$—, —SO— or —CO—.

Z represents a residue of an organic acid represented by ZH.

Each of $Ry_1$ to $Ry_3$ independently represents an alkyl group or a cycloalkyl group, and at least two members out of $Ry_1$ to $Ry_3$ may combine with each other to form a monocyclic or polycyclic hydrocarbon structure, provided that at least one of $Ry_1$ to $Ry_3$ represents a cycloalkyl group or at least two members out of $Ry_1$ to $Ry_3$ are combined to form a monocyclic or polycyclic hydrocarbon structure.

$Ry_4$ represents a hydrogen atom, an alkyl group or a cycloalkyl group.

$Ry_5$ represents a cycloalkyl group.

$Ry_4$ and $Ry_5$ may combine with each other to form a monocyclic or polycyclic hydrocarbon structure.

In formulae (Ia) and (Ib), $R_1$ to $R_4$, X and Z have the same meanings as $R_1$ to $R_4$, X and Z in formula (I).

The alkyl group of $Ry_1$ to $Ry_4$ may be either a linear alkyl group or a branched alkyl group and may have a substituent. The linear or branched alkyl group is preferably a linear or branched alkyl group having a carbon number of 1 to 8, more preferably from 1 to 4, and examples thereof include a methyl group, an ethyl group, a propyl group, an isopropyl group, a butyl group, an isobutyl group and a tert-butyl group, with a methyl group and an ethyl group being preferred.

The cycloalkyl group of $Ry_1$ to $Ry_5$ includes, for example, a monocyclic cycloalkyl group having a carbon number of 3 to 8 and a polycyclic cycloalkyl group having a carbon number of 7 to 14 and may have a substituent. Preferred examples of the monocyclic cycloalkyl group include a cyclopentyl group, a cyclohexyl group and a cyclopropyl group, and preferred examples of the polycyclic cycloalkyl group include an adamantyl group, a norbornane group, a tetracyclododecanyl group, a tricyclodecanyl group and a diamantyl group.

The monocyclic hydrocarbon structure formed by combining at least two members out of $Ry_1$ to $Ry_3$ is preferably a cyclopentane structure or a cyclohexane structure. The polycyclic hydrocarbon structure formed by combining at least two members out of $Ry_1$ to $Ry_3$ is preferably an adamantane structure, a norbornane structure or a tetracyclododecane structure.

Examples of the monocyclic or polycyclic hydrocarbon structure formed by combining $Ry_4$ and $Ry_5$ include a tetramethylene oxide ring structure, a pentamethylene oxide ring structure and a hexamethylene oxide ring structure.

Each of these groups may have a substituent. Examples of the substituent which each of these groups may have include a halogen atom, a hydroxyl group, a nitro group, a cyano group, a carboxyl group, a cycloalkyl group (preferably having a carbon number of 3 to 20), an aryl group (preferably having a carbon number of 6 to 14), an alkoxy group (preferably having a carbon number of 1 to 20), an acyl group (preferably having a carbon number of 2 to 20) and an acyloxy group (preferably having a carbon number of 2 to 20). As for the group having a cyclic structure, such as cycloalkyl group and aryl group, examples of the substituent further include an alkyl group (preferably having a carbon number of 1 to 20).

The compound represented by formula (II), which decomposes by the action of an acid to generate an acid, is a novel compound.

The compound represented by formula (II), which decomposes by the action of an acid to generate an acid, can be synthesized as follows. An α-substituted acetic acid ester that is an active methylene compound is first synthesized by a method of condensing an ester compound under base conditions, a method of reacting alcohol and diketene (described in Synthesis, 387-388 (1989)), or a method of reacting acetoacetate and chloromethyl ether and after sequentially performing monoalkylation of the active methylene and hydroxymethylation of the active methylene by the method described in J. Am. Chem. Soc., 120, 37-45 (1998), the reaction product is finally reacted with sulfonic acid chloride in the presence of a base.

Specific examples of the acid-increasing agent are set forth below, but the present invention is not limited thereto.

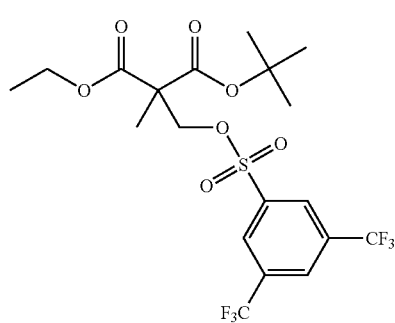

(II-1)

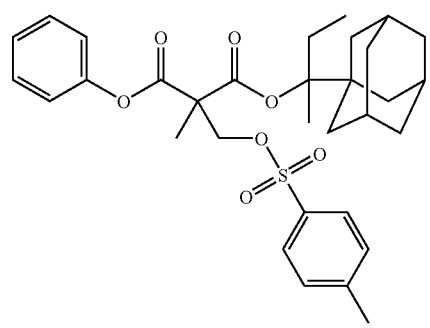

(II-2)

-continued
(II-3)
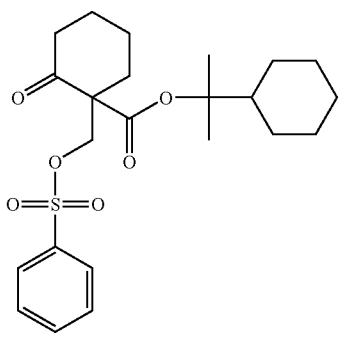
(II-4)
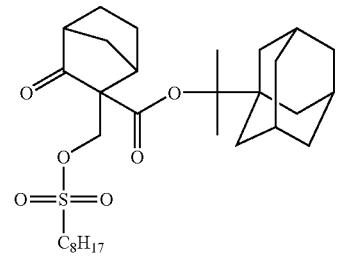
(II-5)
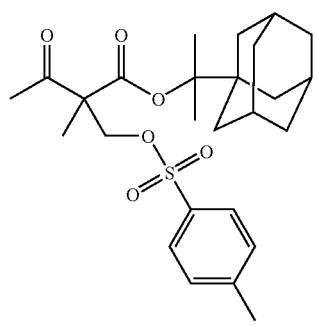
(II-6)
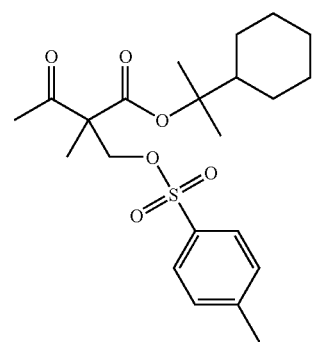
(II-7)
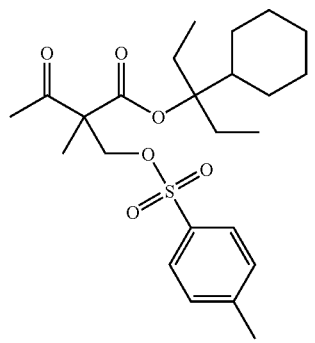
(II-8)
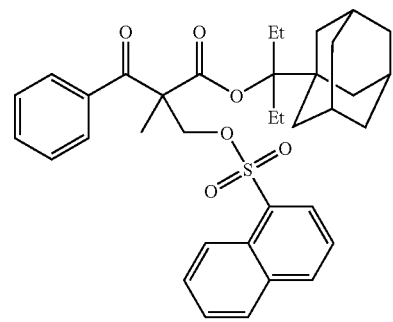
(II-9)
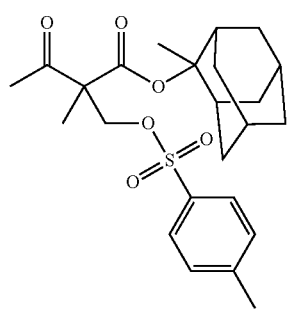
(II-10)
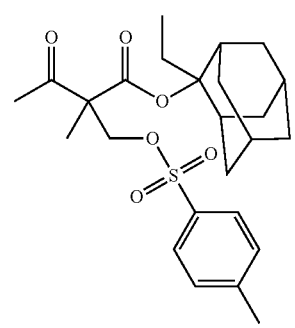

-continued
(II-11)
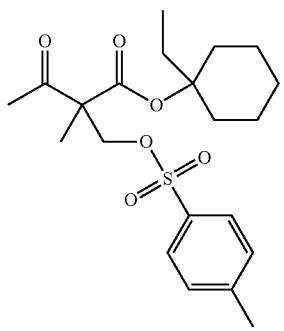
(II-12)
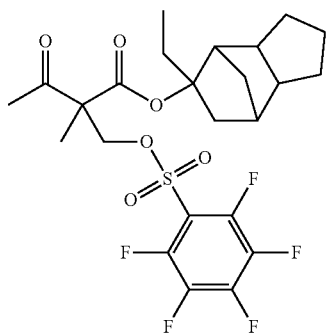
(II-13)
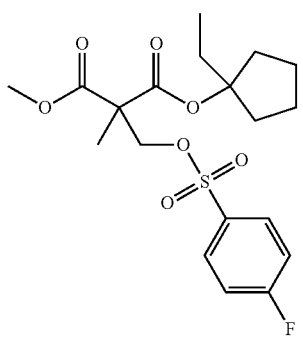
(II-14)
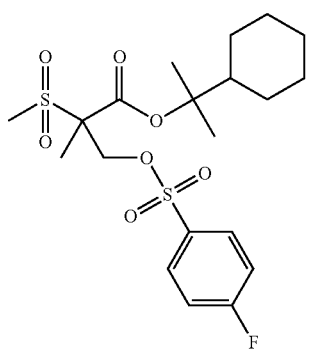
(II-15)
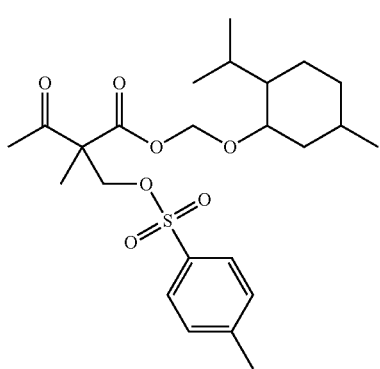
(II-16)
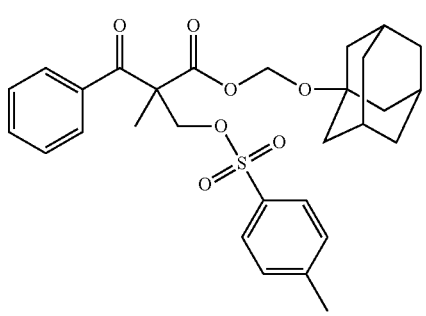
(II-17)
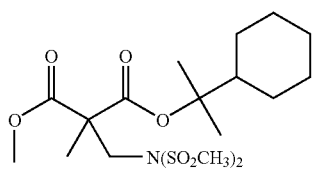
(II-18)
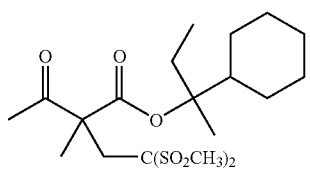
(II-19)
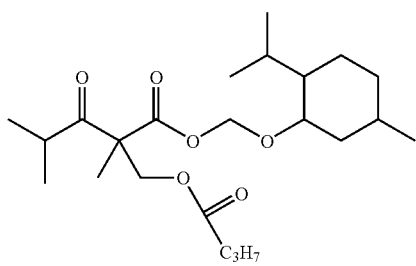
(II-20)
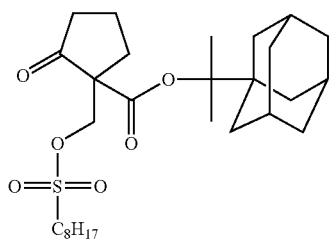

-continued
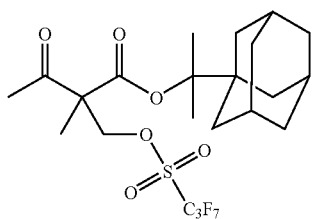
(II-21)
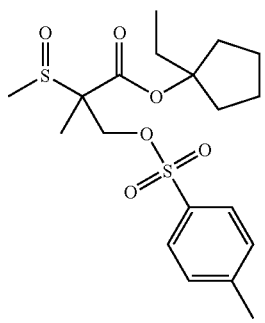
(II-22)
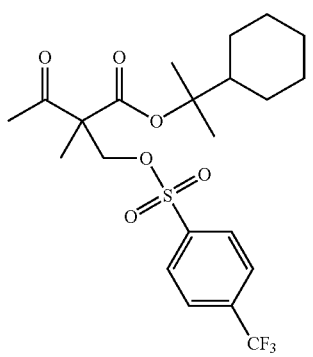
(II-23)
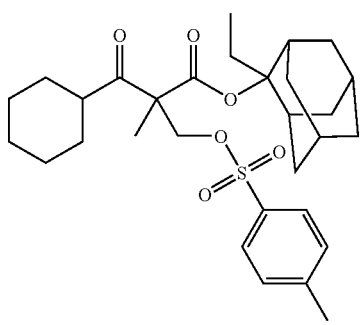
(II-24)
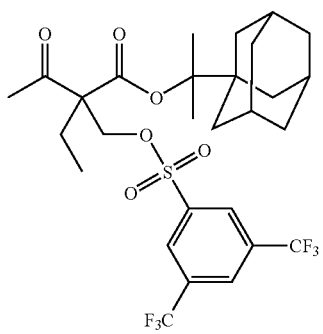
(II-25)
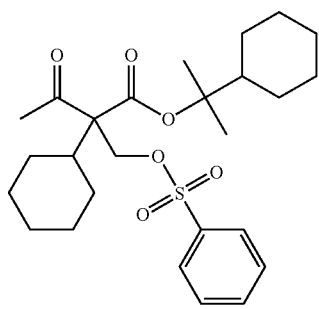
(II-26)
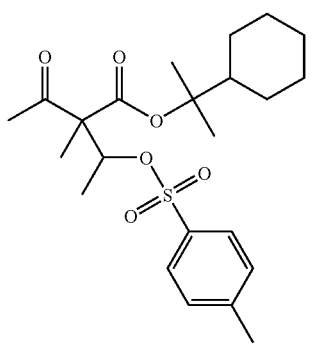
(II-27)
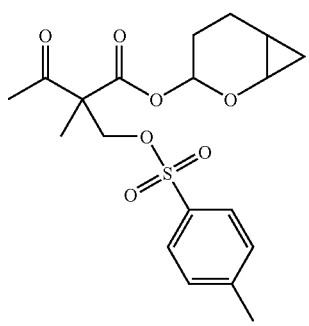
(II-28)

-continued
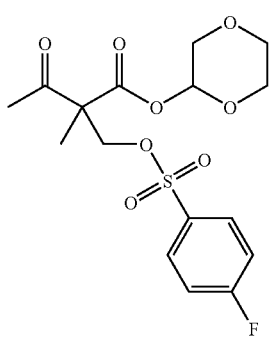
(II-29)
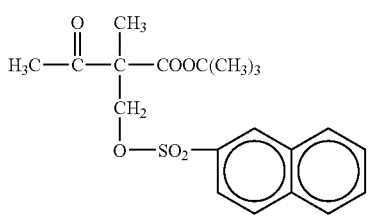
(1-1)
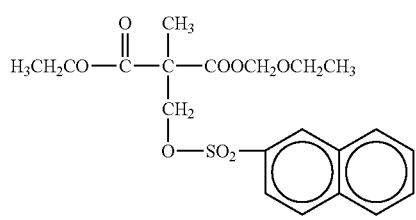
(1-2)
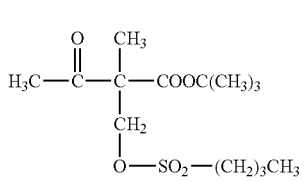
(1-3)
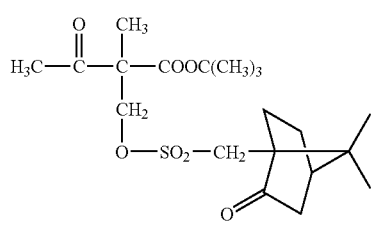
(1-4)
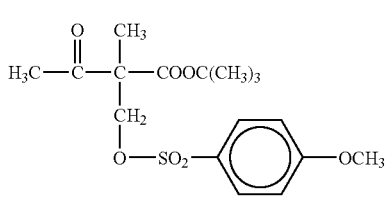
(1-5)
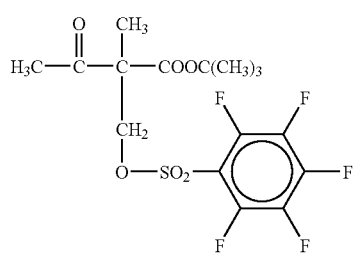
(1-6)
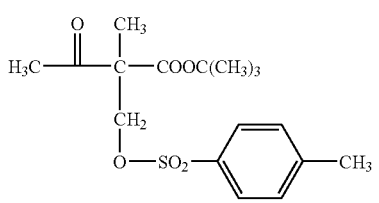
(1-7)
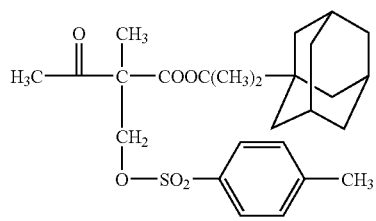
(1-8)
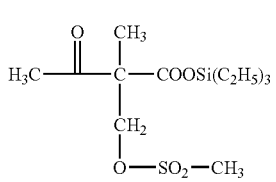
(1-9)
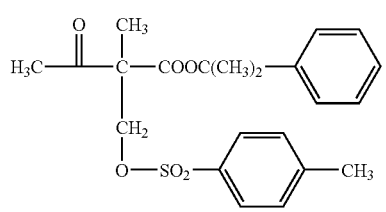
(1-10)
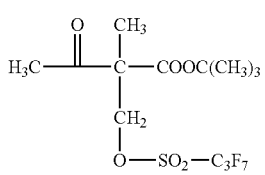
(1-11)
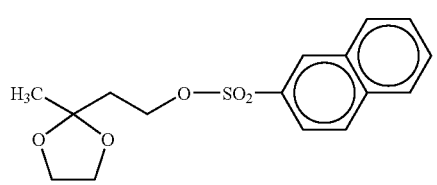
(2-1)
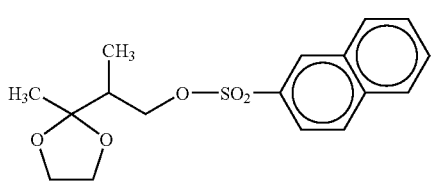
(2-2)

-continued
(2-3)
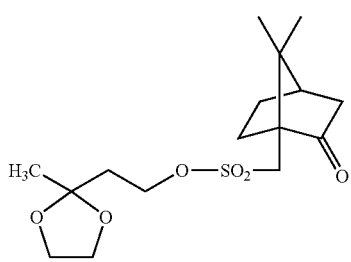
(2-4)
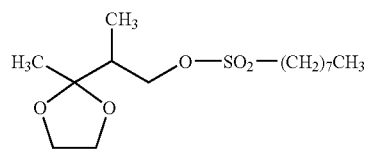
(2-5)
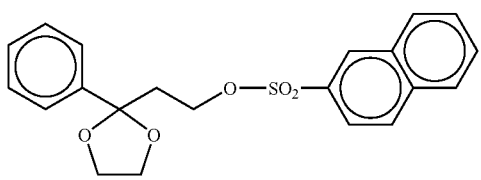
(2-6)
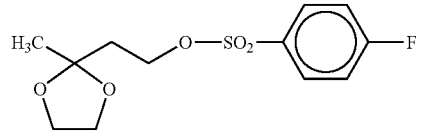
(3-1)
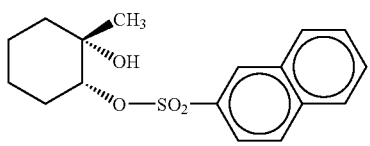
(3-2)
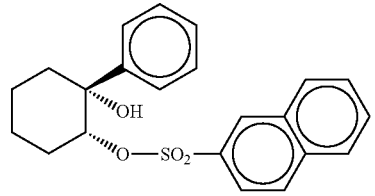
(3-3)
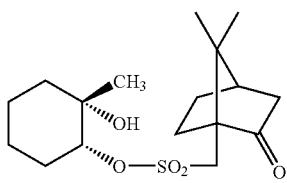
(3-4)
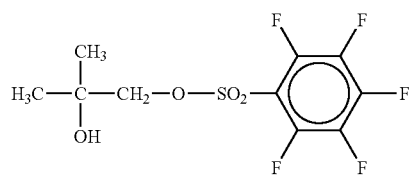
(3-5)
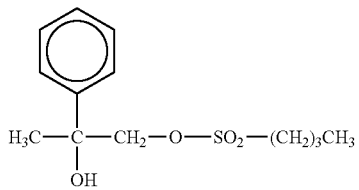
(3-6)
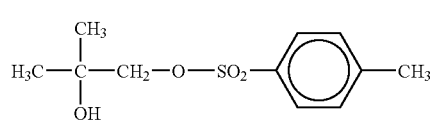
(4-1)
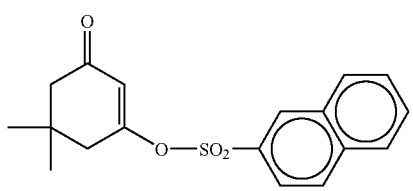
(4-2)
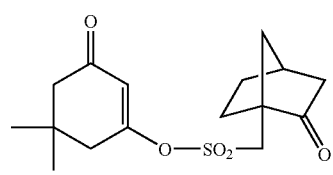
(4-3)
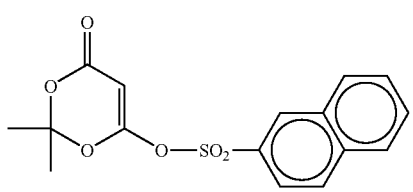
(4-4)
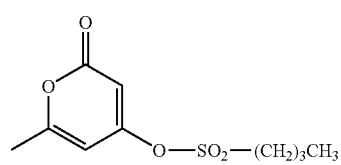
(4-5)
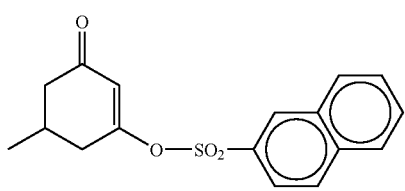
(4-6)
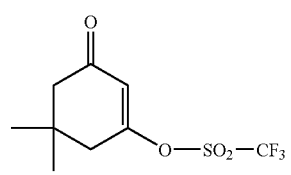

-continued
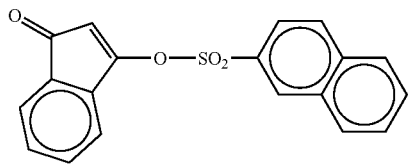
(4-7)
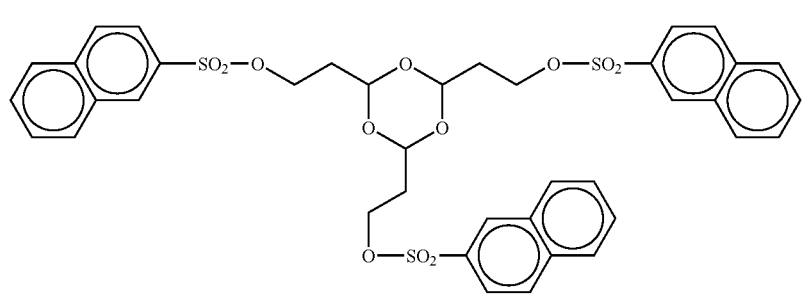
(5-1)
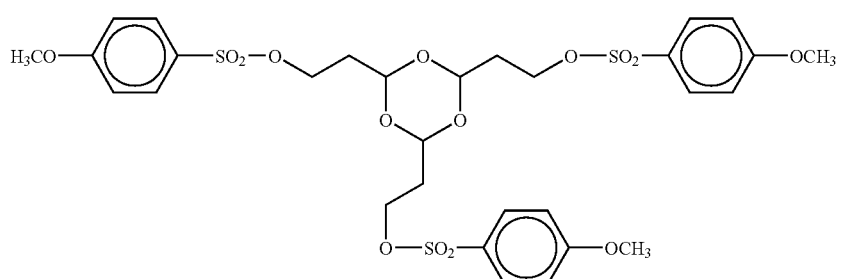
(5-2)
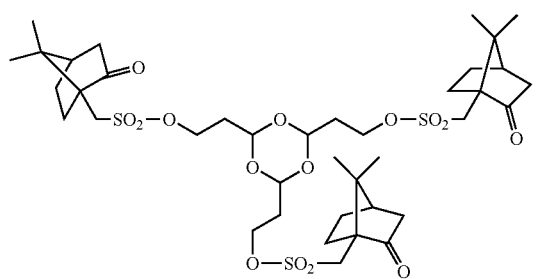
(5-3)
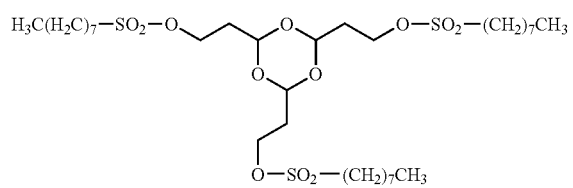
(5-4)
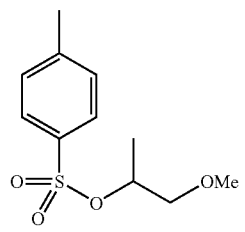
(6-1)
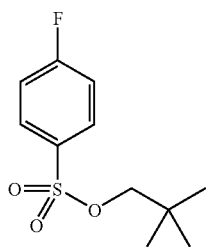
(6-2)
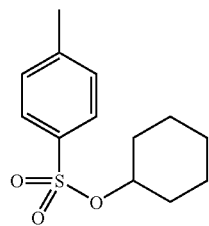
(6-3)
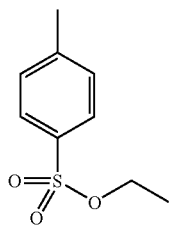
(6-4)

-continued
(6-5)
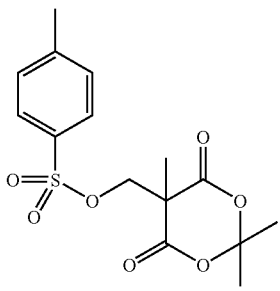
(6-6)
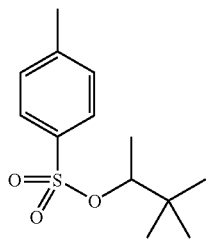
(6-7)
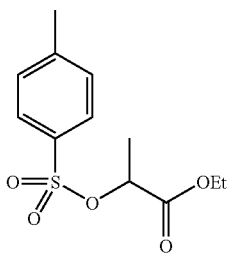
(6-8)
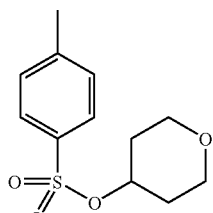
(6-9)
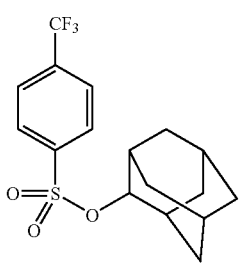
(6-10)
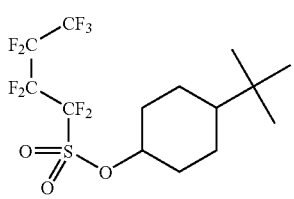
(6-11)
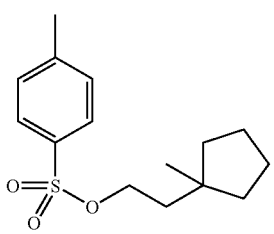
(6-12)
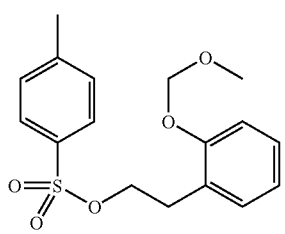
(6-13)
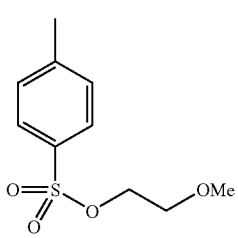
(6-14)
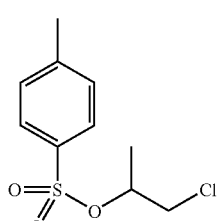
(6-15)
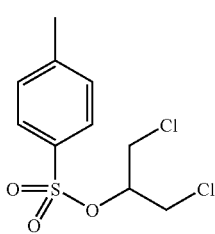
(6-16)
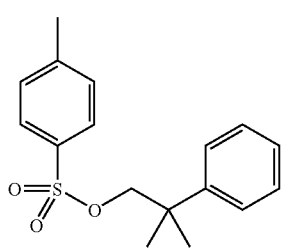

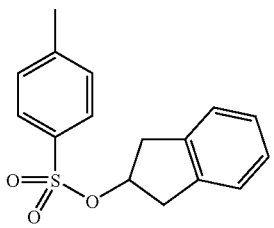 (6-17)

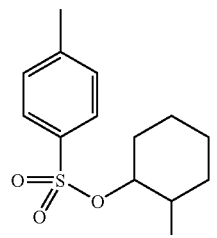 (6-18)

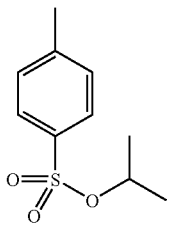 (6-19)

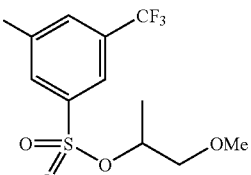 (6-20)

The content of the acid-increasing agent in the photosensitive composition of the present invention is preferably from 0.1 to 20.0 mass %, more preferably from 0.1 to 10.0 mass %, based on the solid content of the composition.

Solvent:

Examples of the solvent which can be used at the time of preparing the photosensitive composition by dissolving the above-described components include an organic solvent such as alkylene glycol monoalkyl ether carboxylate, alkylene glycol monoalkyl ether, alkyl lactate, alkyl alkoxypropionate, cyclic lactone (preferably having a carbon number of 4 to 10), monoketone compound (preferably having a carbon number of 4 to 10) which may contain a ring, alkylene carbonate, alkyl alkoxyacetate and alkyl pyruvate.

Preferred examples of the alkylene glycol monoalkyl ether carboxylate include propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

Preferred examples of the alkylene glycol monoalkyl ether include propylene glycol monomethyl ether, propylene glycol monoethyl ether, propylene glycol monopropyl ether, propylene glycol monobutyl ether, ethylene glycol monomethyl ether and ethylene glycol monoethyl ether.

Preferred examples of the alkyl lactate include methyl lactate, ethyl lactate, propyl lactate and butyl lactate.

Preferred examples of the alkyl alkoxypropionate include ethyl 3-ethoxypropionate, methyl 3-methoxypropionate, methyl 3-ethoxypropionate and ethyl 3-methoxypropionate.

Preferred examples of the cyclic lactone include β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

Preferred examples of the monoketone compound that may contain a ring include 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

Preferred examples of the alkylene carbonate include propylene carbonate, vinylene carbonate, ethylene carbonate and butylene carbonate.

Preferred examples of the alkyl alkoxyacetate include 2-methoxyethyl acetate, 2-ethoxyethyl acetate, 2-(2-ethoxyethoxy)ethyl acetate, 3-methoxy-3-methylbutyl acetate and 1-methoxy-2-propyl acetate.

Preferred examples of the alkyl pyruvate include methyl pyruvate, ethyl pyruvate and propyl pyruvate.

The solvent which can be preferably used includes a solvent having a boiling point of 130° C. or more at ordinary temperature under atmospheric pressure, and specific examples thereof include cyclopentanone, γ-butyrolactone, cyclohexanone, ethyl lactate, ethylene glycol monomethyl ether, acetate, propylene glycol monomethyl ether acetate, ethyl 3-ethoxypropionate, ethyl pyruvate, 2-ethoxyethyl acetate, 2-(2-ethoxyethoxy)ethyl acetate and propylene carbonate.

In the present invention, one of these solvents may be used alone, or two or more kinds thereof may be used in combination.

In the present invention, a mixed solvent prepared by mixing a solvent containing a hydroxyl group in the structure and a solvent containing no hydroxyl group may be used as the organic solvent.

Examples of the solvent containing a hydroxyl group include ethylene glycol, ethylene glycol monomethyl ether, ethylene glycol monoethyl ether, propylene glycol, propylene glycol monomethyl ether, propylene glycol monoethyl ether and ethyl lactate. Among these, propylene glycol monomethyl ether and ethyl lactate are preferred.

Examples of the solvent containing no hydroxyl group include propylene glycol monomethyl ether acetate, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone and butyl acetate are preferred, and propylene glycol monomethyl ether acetate, ethyl ethoxypropionate and 2-heptanone are most preferred.

The mixing ratio (by mass) of the solvent containing a hydroxyl group and the solvent containing no hydroxyl group is usually from 1/99 to 99/1, preferably from 10/90 to 90/10, more preferably from 20/80 to 60/40. A mixed solvent in which the solvent containing no hydroxyl group is contained in an amount of 50 mass % or more is preferred in view of coating uniformity.

The solvent is preferably a mixed solvent of two or more kinds of solvents including propylene glycol monomethyl ether acetate.

Basic Compound:

The positive photosensitive composition of the present invention preferably contains (E) a basic compound so as to reduce the change of performance with aging from exposure to heating.

Preferred basic compounds include a compound having a structure represented by the following formulae (A) to (E):

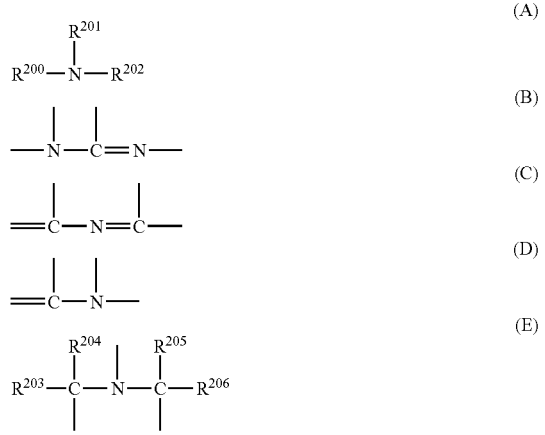

In formulae (A) to (E), each of $R^{200}$, $R^{201}$ and $R^{202}$, which may be the same or different, represents a hydrogen atom, an alkyl group (preferably having a carbon number of 1 to 20), a cycloalkyl group (preferably having a carbon number of 3 to 20) or an aryl group (having a carbon number of 6 to 20), and $R^{201}$ and $R^{202}$ may combine together to form a ring.

As for the alkyl group, the alkyl group having a substituent is preferably an aminoalkyl group having a carbon number of 1 to 20, a hydroxyalkyl group having a carbon number of 1 to 20, or a cyanoalkyl group having a carbon number of 1 to 20.

Each of $R^{203}$, $R^{204}$, $R^{205}$ and $R^{206}$, which may be the same or different, represents an alkyl group having a carbon number of 1 to 20.

The alkyl group in these formulae (A) to (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include triarylsulfonium hydroxide, phenacylsulfonium hydroxide, and sulfonium hydroxide having a 2-oxoalkyl group, specifically, triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. The compound having an onium carboxylate structure is a compound where the anion moiety of the compound having an onium hydroxide structure becomes a carboxylate, and examples thereof include acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline, N,N-dimethylaniline, N,N-dibutylaniline and N,N-dihexylaniline. Examples of the alkylamine derivative having a hydroxyl group and/or an ether bond include ethanolamine, diethanolamine, triethanolamine and tris(methoxyethoxyethyl)amine. Examples of the aniline derivative having a hydroxyl group and/or an ether bond include N,N-bis(hydroxyethyl)aniline.

Other examples include at least one kind of a nitrogen-containing compound selected from a phenoxy group-containing amine compound, a phenoxy group-containing ammonium salt compound, a sulfonic acid ester group-containing amine compound and a sulfonic acid ester group-containing ammonium salt compound.

As for the amine compound, a primary, secondary or tertiary amine compound can be used, and an amine compound where at least one alkyl group is bonded to the nitrogen atom is preferred. The amine compound is more preferably a tertiary amine compound. In the amine compound, as long as at least one alkyl group (preferably having a carbon number of 1 to 20) is bonded to the nitrogen atom, a cycloalkyl group (preferably having a carbon number of 3 to 20) or an aryl group (preferably having a carbon number of 6 to 12) may be bonded to the nitrogen atom, in addition to the alkyl group. The amine compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, an oxyethylene group (—$CH_2CH_2O$—) and an oxypropylene group (—$CH(CH_3)CH_2O$— or —$CH_2CH_2CH_2O$—) are preferred, and an oxyethylene group is more preferred.

As for the ammonium salt compound, a primary, secondary, tertiary or quaternary ammonium salt compound can be used, and an ammonium salt compound where at least one alkyl group is bonded to the nitrogen atom is preferred. In the ammonium salt compound, as long as at least one alkyl group (preferably having a carbon number of 1 to 20) is bonded to the nitrogen atom, a cycloalkyl group (preferably having a carbon number of 3 to 20) or an aryl group (preferably having a carbon number of 6 to 12) may be bonded to the nitrogen atom, in addition to the alkyl group. The ammonium salt compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred. Examples of the anion of the ammonium salt compound include a halogen atom, a sulfonate, a borate and a phosphate, with a halogen atom and a sulfonate being preferred. The halogen atom is preferably chloride, bromide or iodide, and the sulfonate is preferably an organic sulfonate having a carbon number of 1 to 20. The organic sulfonate includes an alkylsulfonate having a carbon number of 1 to 20 and an arylsulfonate. The alkyl group of the alkylsulfonate may have a substituent, and examples of the substituent include fluorine, chlorine, bromine, an alkoxy group, an acyl group and an aryl group. Specific examples of the alkylsulfonate include methanesulfonate, ethanesulfonate, butanesulfonate, hexanesulfonate, octanesulfonate, benzylsulfonate, trifluoromethanesulfonate, pentafluoroethanesulfonate and nonafluorobutanesulfonate. The aryl group of the arylsulfonate includes a benzene ring, a naphthalene ring and an anthracene ring. The benzene ring, naphthalene ring and anthracene ring may have a substituent, and the substituent is preferably a linear or branched alkyl group having a carbon number of 1 to 6, or a cycloalkyl group having a carbon number of 3 to 6. Specific examples of the linear or branched alkyl group and cycloalkyl group include methyl, ethyl, n-propyl, isopropyl, n-butyl, i-butyl, tert-butyl, n-hexyl and cyclohexyl. Other examples of the substituent include an alkoxy group having a carbon number of 1 to 6, a halogen atom, cyano, nitro, an acyl group and an acyloxy group.

The phenoxy group-containing amine compound and the phenoxy group-containing ammonium salt compound are a compound where the alkyl group of an amine compound or ammonium salt compound has a phenoxy group at the terminal opposite the nitrogen atom. The phenoxy group may have a substituent. Examples of the substituent of the phenoxy group include an alkyl group, an alkoxy group, a halogen atom, a cyano group, a nitro group, a carboxyl group, a carboxylic acid ester group, a sulfonic acid ester group, an aryl group, an aralkyl group, an acyloxy group and an aryloxy group. The substitution site of the substituent may be any of 2- to 6-positions, and the number of substituents may be any in the range from 1 to 5.

The compound preferably has at least one oxyalkylene group between the phenoxy group and the nitrogen atom. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

The sulfonic acid ester group in the sulfonic acid ester group-containing amine compound and sulfonic acid ester group-containing ammonium salt compound may be any of an alkylsulfonic acid ester, a cycloalkylsulfonic acid ester and an arylsulfonic acid ester. In the case of an alkylsulfonic acid ester, the alkyl group preferably has a carbon number of 1 to 20; in the case of a cycloalkylsulfonic acid ester, the cycloalkyl group preferably has a carbon number of 3 to 20; and in the case of an arylsulfonic acid ester, the aryl group preferably has a carbon number of 6 to 12. The alkylsulfonic acid ester, cycloalkylsulfonic acid ester and arylsulfonic acid ester may have a substituent, and the substituent is preferably a halogen atom, a cyano group, a nitro group, a carboxyl group, a carboxylic acid ester group or a sulfonic acid ester group.

The compound preferably has at least one oxyalkylene group between the sulfonic acid ester group and the nitrogen atom. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

One of these basic compounds may be used alone, or two or more kinds thereof may be used in combination.

The amount of the basic compound used is usually from 0.001 to 10 mass %, preferably from 0.01 to 5 mass %, based on the solid content of the positive resist composition.

The ratio of acid generator and basic compound used in the composition is preferably acid generator/basic compound (by mol)=from 2.5 to 300. That is, the molar ratio is preferably 2.5 or more in view of sensitivity and resolution and preferably 300 or less from the standpoint of suppressing the reduction in resolution due to thickening of the resist pattern with aging after exposure until heat treatment. The acid generator/basic compound (by mol) is more preferably from 5.0 to 200, still more preferably from 7.0 to 150.

Surfactant:

The photosensitive composition of the present invention preferably further contains a surfactant, more preferably any one of fluorine-containing and/or silicon-containing surfactants (a fluorine-containing surfactant, a silicon-containing surfactant and a surfactant containing both a fluorine atom and a silicon atom), or two or more kinds thereof.

By incorporating the above-described surfactant into the photosensitive composition of the present invention, a resist pattern with good performance in terms of sensitivity, resolution and adherence as well as less development defect can be provided when an exposure light source of 250 nm or less, particularly 220 nm or less, is used.

Examples of the fluorine-containing and/or silicon-containing surfactants include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include a fluorine-containing surfactant and a silicon-containing surfactant, such as EFtop EF301 and EF303 (produced by Shin-Akita Kasei K.K.); Florad FC430, 431 and 4430 (produced by Sumitomo 3M Inc.); Megaface F171, F173, F176, F189, F113, F110, F177, F120 and R08 (produced by Dainippon Ink & Chemicals, Inc.); Surflon S-382, SC101, 102, 103, 104, 105 and 106 (produced by Asahi Glass Co., Ltd.); Troysol S-366 (produced by Troy Chemical); GF-300 and GF-150 (produced by Toagosei Chemical Industry Co., Ltd.); Surflon S-393 (produced by Seimi Chemical Co., Ltd.); EFtop EF121, EF122A, EF122B, RF122C, EF125M, EF135M, EF351, 352, EF801, EF802 and EF601 (produced by JEMCO Inc.); PF636, PF656, PF6320 and PF6520 (produced by OMNOVA); and FTX-204G, 208G, 218G, 230G, 204D, 208D, 212D, 218D and 222D (produced by NEOS Co., Ltd.). In addition, polysiloxane polymer KP-341 (produced by Shin-Etsu Chemical Co., Ltd.) may also be used as a silicon-containing surfactant.

Other than these known surfactants, a surfactant using a polymer having a fluoro-aliphatic group derived from a fluoro-aliphatic compound that is produced by a telomerization process (also called a telomer process) or an oligomerization process (also called an oligomer process), may be used. The fluoro-aliphatic compound can be synthesized by the method described in JP-A-2002-90991.

The polymer having a fluoro-aliphatic group is preferably a copolymer of a fluoro-aliphatic group-containing monomer with a (poly(oxyalkylene))acrylate and/or a (poly(oxyalkylene))methacrylate, and the polymer may have an irregular distribution or may be a block copolymer. Examples of the poly(oxyalkylene) group include a poly(oxyethylene) group, a poly(oxypropylene) group and a poly(oxybutylene) group. This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer and a (poly(oxyalkylene))acrylate (or methacrylate) is not limited only to a binary copolymer but may also be a ternary or greater copolymer obtained by simultaneously copolymerizing two or more different fluoro-aliphatic group-containing monomers or two or more different (poly(oxyalkylene))acrylates (or methacrylates).

Examples thereof include, as the commercially available surfactant, Megaface F178, F-470, F-473, F-475, F-476 and F-472 (produced by Dainippon Ink & Chemicals, Inc.) and further include a copolymer of a $C_6F_{13}$ group-containing acrylate (or methacrylate) with a (poly(oxyalkylene))acrylate (or methacrylate), and a copolymer of a $C_3F_7$ group-containing acrylate (or methacrylate) with a (poly(oxyethylene)) acrylate (or methacrylate) and a (poly(oxypropylene))acrylate (or methacrylate).

In the present invention, a surfactant other than the fluorine-containing and/or silicon-containing surfactants may also be used. Specific examples thereof include a nonionic surfactant such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkylallyl ethers (e.g., polyoxyethylene octylphenol ether, polyoxyethylene nonylphenol ether), polyoxyethylene•polyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate), and polyoxyethylene sorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate).

One of such surfactants may be used alone, or some of them may be used in combination.

The amount of the surfactant used is preferably from 0.01 to 10 mass %, more preferably from 0.1 to 5 mass %, based on the entire amount of the photosensitive composition (excluding the solvent).

Onium Carboxylate:

The photosensitive composition of the present invention may contain an onium carboxylate. Examples of the onium carboxylate include sulfonium carboxylate, iodonium carboxylate and ammonium carboxylate. In particular, the onium carboxylate is preferably an iodonium salt or a sulfonium salt. Furthermore, the carboxylate residue of the onium carboxylate for use in the present invention preferably contains no aromatic group and no carbon-carbon double bond. The anion moiety is preferably a linear or branched, monocyclic or polycyclic alkylcarboxylate anion having a carbon number of 1 to 30, more preferably the carboxylate anion above with the alkyl group being partially or entirely fluorine-substituted. The alkyl chain may contain an oxygen atom. By virtue of such a construction, transparency to light at 220 nm or less is ensured, the sensitivity and resolution are enhanced, and the iso/dense bias and exposure margin are improved.

Examples of the fluorine-substituted carboxylate anion include fluoroacetate, difluoroacetate, trifluoroacetate, pentafluoropropionate, heptafluorobutyrate, nonafluoropentanoate, perfluorododecanoate, perfluorotridecanoate, perfluorocyclohexanecarboxylate and 2,2-bistrifluoromethylpropionate anions.

These onium carboxylates can be synthesized by reacting a sulfonium, iodonium or ammonium hydroxide and a carboxylic acid with silver oxide in an appropriate solvent.

The content of the onium carboxylate in the composition is generally from 0.1 to 20 mass %, preferably from 0.5 to 10 mass %, more preferably from 1 to 7 mass %, based on the entire solid content of the composition.

Dissolution inhibiting compound having a molecular weight of 3,000 or less and being capable of decomposing by the action of an acid to increase the solubility in an alkali developer:

The dissolution inhibiting compound having a molecular weight of 3,000 or less and being capable of decomposing by the action of an acid to increase the solubility in an alkali developer (hereinafter, sometimes referred to as a "dissolution inhibiting compound") is preferably an alicyclic or aliphatic compound containing an acid-decomposable group, such as acid-decomposable group-containing cholic acid derivative described in Proceeding of SPIE, 2724, 355 (1996), so as not to reduce the transparency to light at 220 nm or less. Examples of the acid-decomposable group and alicyclic structure are the same as those described above with respect to the resin as the component (A).

In the case where the photosensitive composition of the present invention is exposed to KrF excimer laser or irradiated with electron beam, the composition preferably contains a structure where the phenolic hydroxyl group of a phenol compound is substituted by an acid-decomposable group. The phenol compound is preferably a compound containing from 1 to 9 phenol skeletons, more preferably from 2 to 6 phenol skeletons.

The molecular weight of the dissolution inhibiting compound for use in the present invention is 3,000 or less, preferably from 300 to 3,000, more preferably from 500 to 2,500.

The amount of the dissolution inhibiting compound added is preferably from 3 to 50 mass %, more preferably from 5 to 40 mass %, based on the solid content of the photosensitive composition.

Specific examples of the dissolution inhibiting compound are set forth below, but the present invention is not limited thereto.

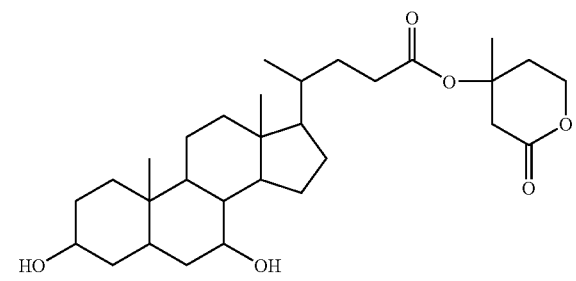

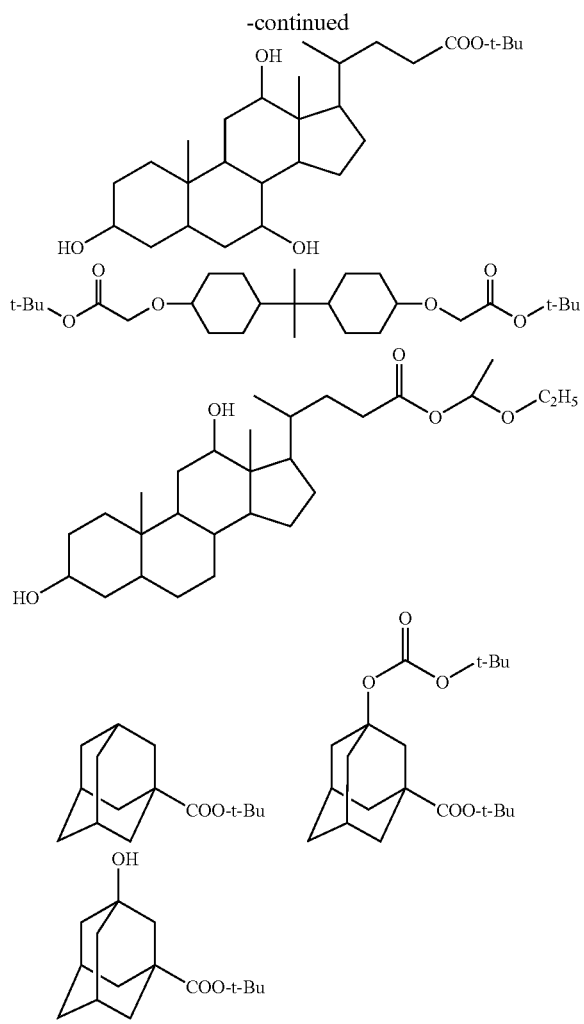

Other Additives:

The photosensitive composition of the present invention may further contain, for example, a dye, a plasticizer, a photosensitizer, a light absorber and a compound for accelerating dissolution in a developer (for example, a phenol compound having a molecular weight of 1,000 or less, or a carboxyl group-containing alicyclic or aliphatic compound), if desired.

The phenol compound having a molecular weight of 1,000 or less can be easily synthesized by one skilled in the art by referring to the methods described, for example, in JP-A-4-122938, JP-A-2-28531, U.S. Pat. No. 4,916,210 and European Patent 219294.

Specific examples of the carboxyl group-containing alicyclic or aliphatic compound include, but are not limited to, a carboxylic acid derivative having a steroid structure, such as cholic acid, deoxycholic acid and lithocholic acid, an adamantanecarboxylic acid derivative, an adamantanedicarboxylic acid, a cyclohexanecarboxylic acid and a cyclohexanedicarboxylic acid.

Pattern Forming Method:

The pattern forming method according to an embodiment of the present invention comprises steps of forming a photosensitive film from the photosensitive composition of the present invention, and exposing and developing the photosensitive film. The photosensitive composition of the present invention is preferably used in a film thickness of 30 to 250 nm, more preferably from 30 to 200 nm, from the standpoint of enhancing the resolution. Such a film thickness can be obtained by setting the solid content concentration in the photosensitive composition to an appropriate range, thereby imparting an appropriate viscosity and enhancing the coatability and film-forming property.

The entire solid content concentration in the photosensitive composition is generally from 1 to 10 mass %, preferably from 1 to 8.0 mass %, more preferably from 1.0 to 6.0 mass %.

The photosensitive composition of the present invention is used by dissolving the components above in a predetermined organic solvent, preferably in the above-described mixed solvent, filtering the solution, and applying it on a predetermined support as follows. The filter used for filtering is preferably a polytetrafluoroethylene-, polyethylene- or nylon-made filter having a pore size of 0.1 μm or less, more preferably 0.05 μm or less, still more preferably 0.03 μm or less.

For example, the photosensitive composition is applied on such a substrate (e.g., silicon/silicon dioxide-coated substrate) as used in the production of a precision integrated circuit device, by an appropriate coating method such as spinner or coater and dried to form a photosensitive film.

The photosensitive film is irradiated with an actinic ray or radiation through a predetermined mask, preferably heated (baked) and then subjected to development and rinsing, whereby a good pattern can be obtained.

Examples of the actinic ray or radiation include infrared light, visible light, ultraviolet light, far ultraviolet light, X-ray and electron beam, but the radiation is preferably far ultraviolet light at a wavelength of 250 nm or less, more preferably 220 nm or less, still more preferably from 1 to 200 nm. Specific examples thereof include KrF excimer laser (248 nm), ArF excimer laser (193 nm), $F_2$ excimer laser (157 nm), X-ray and electron beam, with ArF excimer laser, $F_2$ excimer laser, EUV (13 nm) and electron beam being preferred.

Before forming the photosensitive film, an antireflection film may be previously provided by coating on the substrate.

The antireflection film used may be either an inorganic film type such as titanium, titanium dioxide, titanium nitride, chromium oxide, carbon and amorphous silicon, or an organic film type composed of a light absorber and a polymer material. Also, a commercially available organic antireflection film such as DUV30 Series and DUV-40 Series produced by Brewer Science, Inc., and AR-2, AR-3 and AR-5 produced by Shipley Co., Ltd. can be used as the organic antireflection film.

In the development step, an alkali developer is used as follows. The alkali developer which can be used for the photosensitive composition is an alkaline aqueous solution of, for example, inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

Furthermore, this alkali developer may be used after adding thereto alcohols and a surfactant each in an appropriate amount.

The alkali concentration of the alkali developer is usually from 0.1 to 20 mass %.

The pH of the alkali developer is usually from 10.0 to 15.0.

Also, the above-described alkaline aqueous solution may be used after adding thereto alcohols and a surfactant each in an appropriate amount.

As for the rinsing solution, pure water is used, and the pure water may be used after adding thereto a surfactant in an appropriate amount.

After the development or rinsing, the developer or rinsing solution adhering on the pattern may removed by a supercritical fluid.

The exposure may also be performed by filling a liquid (immersion medium) having a refractive index higher than that of air between the photosensitive film and a lens at the irradiation with an actinic ray or radiation (immersion exposure). By this exposure, the resolution can be enhanced. The immersion medium used may be any liquid as long as it has a refractive index higher than that of air, but pure water is preferred.

The immersion liquid used in the immersion exposure is described below.

The immersion liquid is preferably a liquid being transparent to light at the exposure wavelength and having as small a temperature coefficient of refractive index as possible so as to minimize the distortion of an optical image projected on the resist film. Particularly, when the exposure light source is an ArF excimer laser (wavelength: 193 nm), water is preferably used in view of easy availability and easy handleability, in addition to the above-described aspects.

Furthermore, a medium having a refractive index of 1.5 or more can also be used from the standpoint that the refractive index can be more enhanced. This medium may be either an aqueous solution or an organic solvent.

In the case of using water as the immersion liquid, for decreasing the surface tension of water and increasing the surface activity, an additive (liquid) which does not dissolve the resist film on a wafer and at the same time, gives only a negligible effect on the optical coat at the undersurface of the lens element, may be added in a small ratio. The additive is preferably an aliphatic alcohol having a refractive index nearly equal to that of water, and specific examples thereof include methyl alcohol, ethyl alcohol and isopropyl alcohol. By virtue of adding an alcohol having a refractive index nearly equal to that of water, even when the alcohol component in water is evaporated and its content concentration is changed, the change in the refractive index of the entire liquid can be advantageously made very small. On the other hand, if a substance opaque to light at 193 nm or an impurity greatly differing in the refractive index from water is mingled, this incurs distortion of the optical image projected on the resist film. Therefore, the water used is preferably distilled water. Pure water obtained by further filtering the distilled water through an ion exchange filter or the like may also be used.

The electrical resistance of water is preferably 18.3 MΩcm or more, and TOC (total organic carbon) is preferably 20 ppb or less. The water is preferably subjected to a deaeration treatment.

Also, the lithography performance can be enhanced by increasing the refractive index of the immersion liquid. From such a standpoint, an additive for increasing the refractive index may be added to water, or deuterated water ($D_2O$) may be used in place of water.

In the case where the resist film formed of the photosensitive composition of the present invention is exposed through an immersion medium, a hydrophobic resin (HR) may be further added, if desired. The hydrophobic resin (HR) when added is unevenly distributed to the surface layer of the resist film and in the case of using water as the immersion medium, the resist film formed can be enhanced in the receding contact angle on the resist film surface for water as well as in the followability of the immersion liquid. The hydrophobic resin (HR) may be any resin as long as the receding contact angle on the surface can be enhanced by its addition, but a resin having at least either one of a fluorine atom and a silicon atom is preferred. The receding contact angle of the resist film is preferably from 60 to 90°, more preferably 70° or more. The amount of the hydrophobic resin added may be appropriately adjusted to give a resist film having a receding contact angle in the range above but is preferably from 0.1 to 10 mass %, more preferably from 0.1 to 5 mass %, based on the entire solid content of the photosensitive composition. The hydrophobic resin (HR) is, as described above, unevenly distributed to the interface but unlike a surfactant, need not have necessarily a hydrophilic group in the molecule and may not contribute to uniform mixing of polar/nonpolar substances.

The receding contact angle is a contact angle measured when a contact line recedes on the liquid droplet-substrate interface, and this contact angle is generally known to be useful in simulating the mobility of a liquid droplet in a dynamic state. In a simple manner, the receding contact angle can be defined as a contact angle at the time of the liquid droplet interface receding when a liquid droplet ejected from a needle tip is landed on a substrate and then the liquid droplet is again suctioned into the needle. In general, the receding contact angle can be measured by a contact angle measuring method called an expansion/contraction method.

In the immersion exposure step, the immersion liquid needs to move on a wafer following the movement of an exposure head that is scanning the wafer at a high speed and forming an exposure pattern. Therefore, the contact angle of the immersion liquid with the resist film in a dynamic state is important, and a performance of allowing a liquid droplet to follow the high-speed scanning of an exposure head with no remaining is required of the resist.

The fluorine atom or silicon atom in the hydrophobic resin (HR) may be present in the main chain of the resin or may be substituted on the side chain.

The hydrophobic resin (HR) is preferably a resin having a fluorine atom-containing alkyl group, a fluorine atom-containing cycloalkyl group or a fluorine atom-containing aryl group, as a fluorine atom-containing partial structure.

The fluorine atom-containing alkyl group (preferably having a carbon number of 1 to 10, more preferably from 1 to 4) is a linear or branched alkyl group with at least one hydrogen atom being replaced by a fluorine atom and may further have other substituents.

The fluorine atom-containing cycloalkyl group is a monocyclic or polycyclic cycloalkyl group with at least one hydrogen atom being replaced by a fluorine atom and may further have other substituents.

The fluorine atom-containing aryl group is an aryl group (e.g., phenyl, naphthyl) with at least one hydrogen atom being replaced by a fluorine atom and may further have other substituents.

Preferred examples of the fluorine atom-containing alkyl group, fluorine atom-containing cycloalkyl group and fluorine atom-containing aryl group include the groups represented by the following formulae (F2) to (F4), but the present invention is not limited thereto.

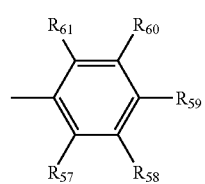

(F2)

-continued

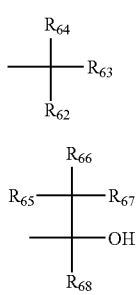

In formulae (F2) to (F4), each of $R_{57}$ to $R_{68}$ independently represents a hydrogen atom, a fluorine atom or an alkyl group, provided that at least one of $R_{57}$ to $R_{61}$, at least one of $R_{62}$ to $R_{64}$ and at least one of $R_{65}$ to $R_{68}$ are a fluorine atom or an alkyl group (preferably having a carbon number of 1 to 4) with at least one hydrogen atom being replaced by a fluorine atom. It is preferred that $R_{57}$ to $R_{61}$ and $R_{65}$ to $R_{67}$ all are a fluorine atom. Each of $R_{62}$, $R_{63}$ and $R_{68}$ is preferably an alkyl group (preferably having a carbon number of 1 to 4) with at least one hydrogen atom being replaced by a fluorine atom, more preferably a perfluoroalkyl group having a carbon number of 1 to 4. $R_{62}$ and $R_{63}$ may combine together to form a ring.

Specific examples of the group represented by formula (F2) include p-fluorophenyl group, pentafluorophenyl group and 3,5-di(trifluoromethyl)phenyl group.

Specific examples of the group represented by formula (F3) include trifluoromethyl group, pentafluoropropyl group, pentafluoroethyl group, heptafluorobutyl group, hexafluoroisopropyl group, heptafluoroisopropyl group, hexafluoro(2-methyl)isopropyl group, nonafluorobutyl group, octafluoroisobutyl group, nonafluorohexyl group, nonafluoro-tert-butyl group, perfluoroisopentyl group, perfluorooctyl group, perfluoro(trimethyl)hexyl group, 2,2,3,3-tetrafluorocyclobutyl group and perfluorocyclohexyl group. Among these, hexafluoroisopropyl group, heptafluoroisopropyl group, hexafluoro(2-methyl)isopropyl group, octafluoroisobutyl group, nonafluoro-tert-butyl group and perfluoroisopentyl group are preferred, and hexafluoroisopropyl group and heptafluoroisopropyl group are more preferred.

Specific examples of the group represented by formula (F4) include —C(CF$_3$)$_2$OH, —C(C$_2$F$_5$)$_2$OH, —C(CF$_3$)(CH$_3$)OH and —CH(CF$_3$)OH, with —C(CF$_3$)$_2$OH being preferred.

Specific examples of the repeating unit having a fluorine atom are set forth below, but the present invention is not limited thereto.

In specific examples, $X_1$ represents a hydrogen atom, —CH$_3$, —F or —CF$_3$.

$X_2$ represents —F or —CF$_3$.

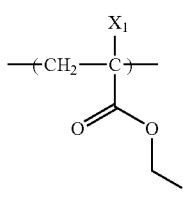 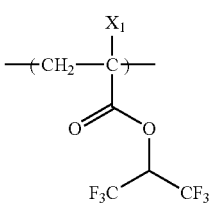

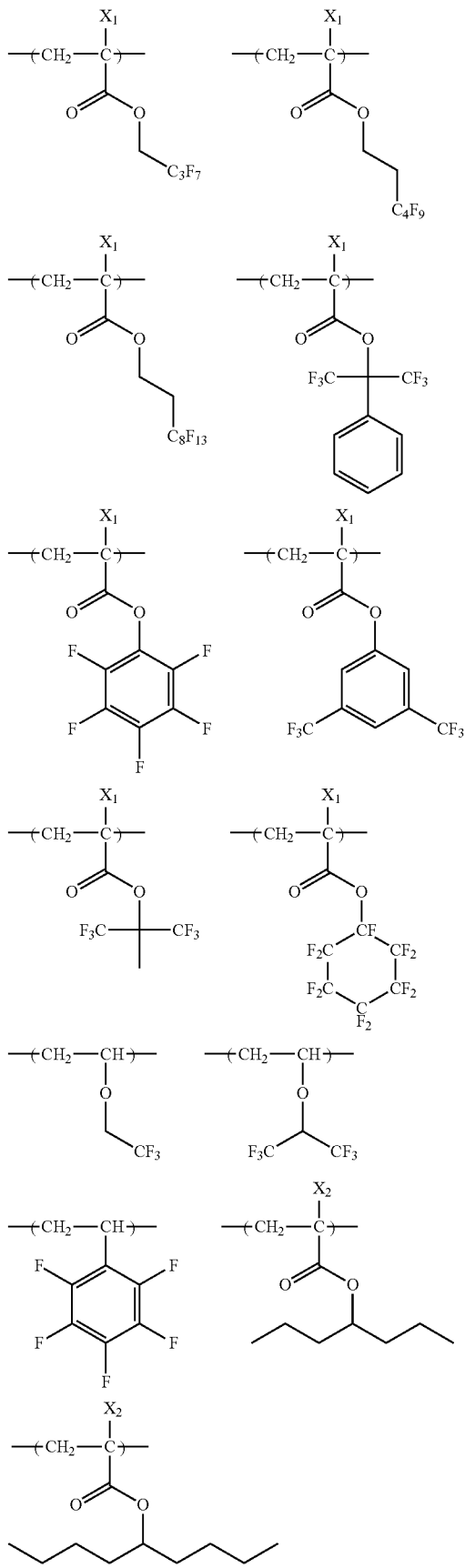

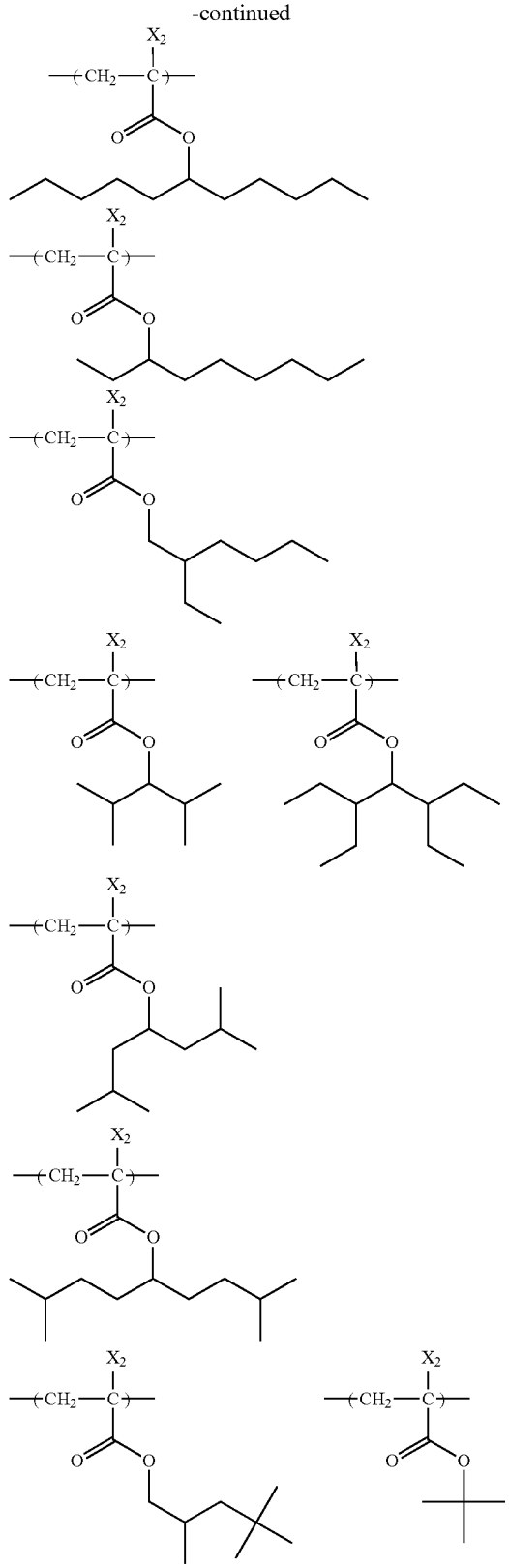

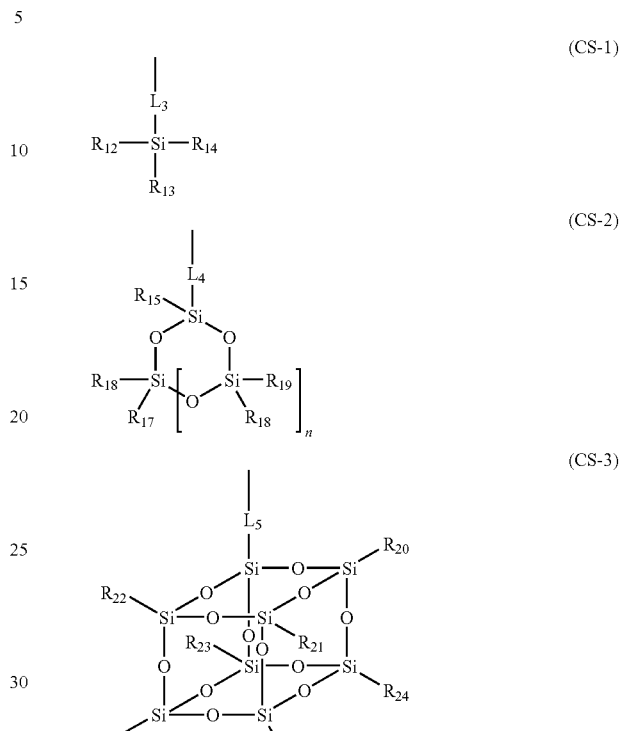

Specific examples of the alkylsilyl structure and cyclic siloxane structure include groups represented by the following formulae (CS-1) to (CS-3):

In formulae (CS-1) to (CS-3), each of $R_{12}$ to $R_{26}$ independently represents a linear or branched alkyl group (preferably having a carbon number of 1 to 20) or a cycloalkyl group (preferably having a carbon number of 3 to 20).

Each of $L_3$ to $L_5$ represents a single bond or a divalent linking group. Examples of the divalent linking group include a single group and a combination of two or more groups, selected from the group consisting of an alkylene group, a phenyl group, an ether group, a thioether group, a carbonyl group, an ester group, an amide group, a urethane group and a urea group.

n represents an integer of 1 to 5.

Specific examples of the repeating unit having a silicon atom are set forth below, but the present invention is not limited thereto.

In specific examples, $X_1$ represents a hydrogen atom, —$CH_3$, —F or —$CF_3$.

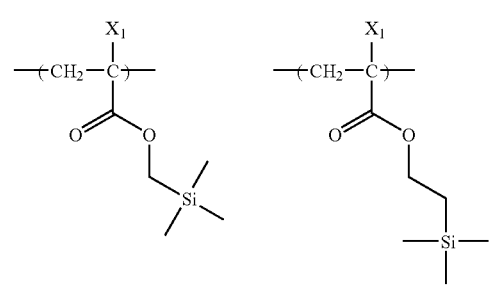

The hydrophobic resin (HR) is preferably a resin having an alkylsilyl structure (preferably a trialkylsilyl group) or a cyclic siloxane structure, as a silicon atom-containing partial structure.

111
-continued

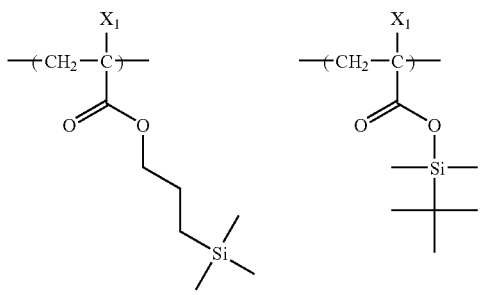
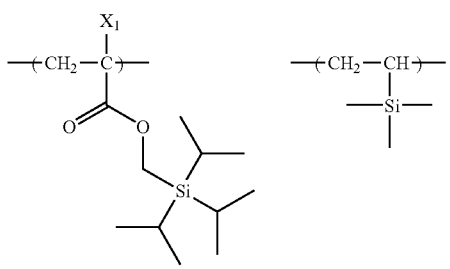
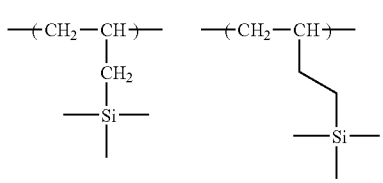
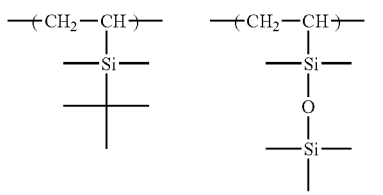
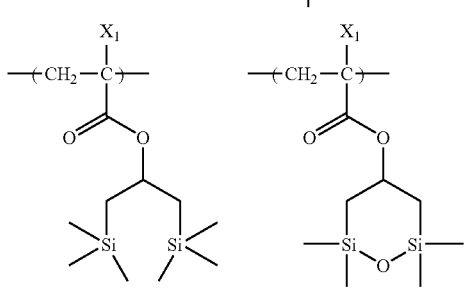
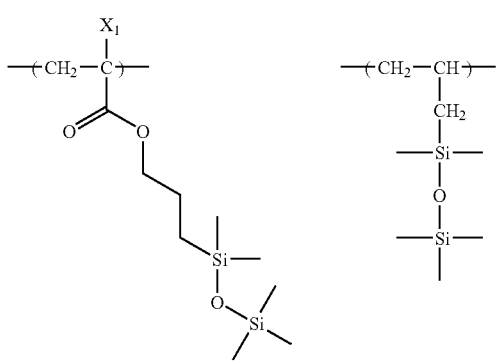

112
-continued

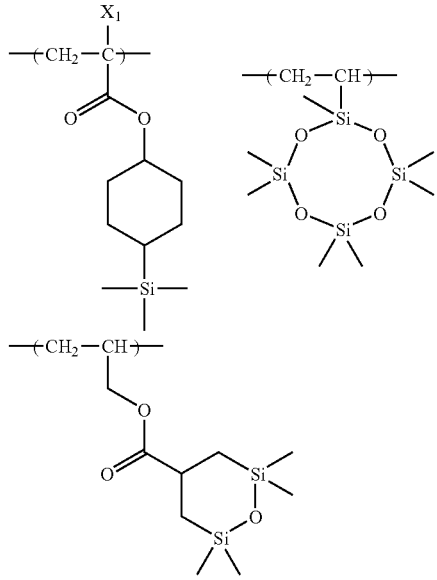
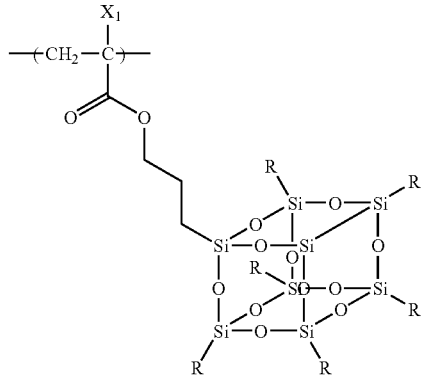

$R = CH_3, C_2H_5, C_3H_7, C_4H_9$

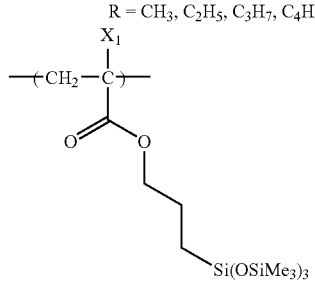

Furthermore, the hydrophobic resin (HR) may contain at least one group selected from the group consisting of the following (x) to (z):
(x) an alkali-soluble group,
(y) a group capable of decomposing by the action of an alkali developer to increase the solubility in an alkali developer, and
(z) a group capable of decomposing by the action of an acid.

Examples of the (x) alkali-soluble group include a group having a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group or a tris(alkylsulfonyl)methylene group.

Preferred alkali-soluble groups include a fluorinated alcohol group (preferably hexafluoroisopropanol), a sulfonimide group and a bis(carbonyl)methylene group.

As for the repeating unit having (x) an alkali-soluble group, all of a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the polymer chain terminal by using an alkali-soluble group-containing polymerization initiator or chain transfer agent at the polymerization, are preferred.

The content of the repeating unit having (x) an alkali-soluble group is preferably from 1 to 50 mol %, more preferably from 3 to 35 mol %, still more preferably from 5 to 20 mol %, based on all repeating units in the polymer.

Specific examples of the repeating unit having (x) an alkali-soluble group are set forth below, but the present invention is not limited thereto.

In the formulae, Rx represents H, $CH_3$, $CF_3$ or $CH_2OH$.

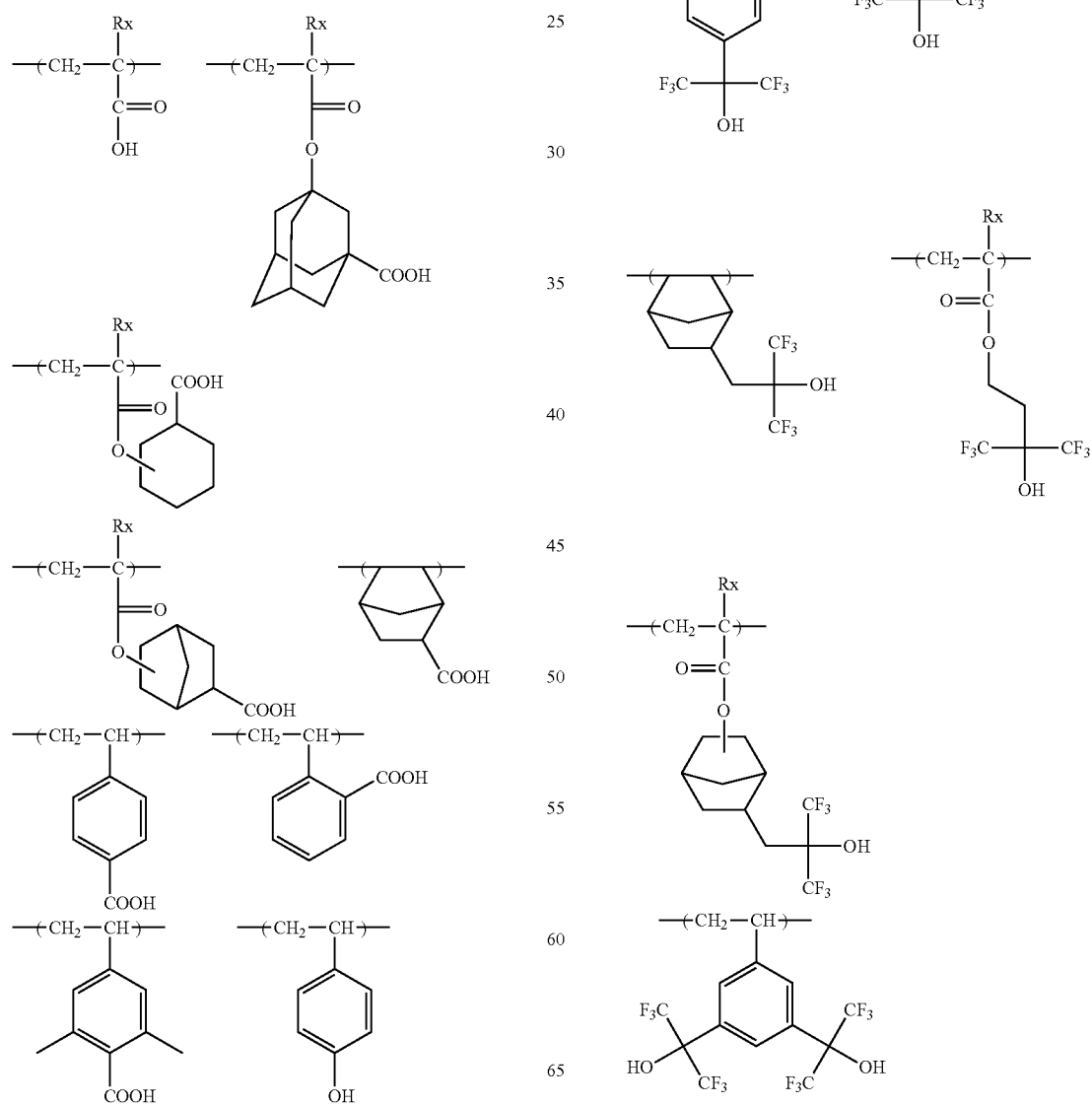

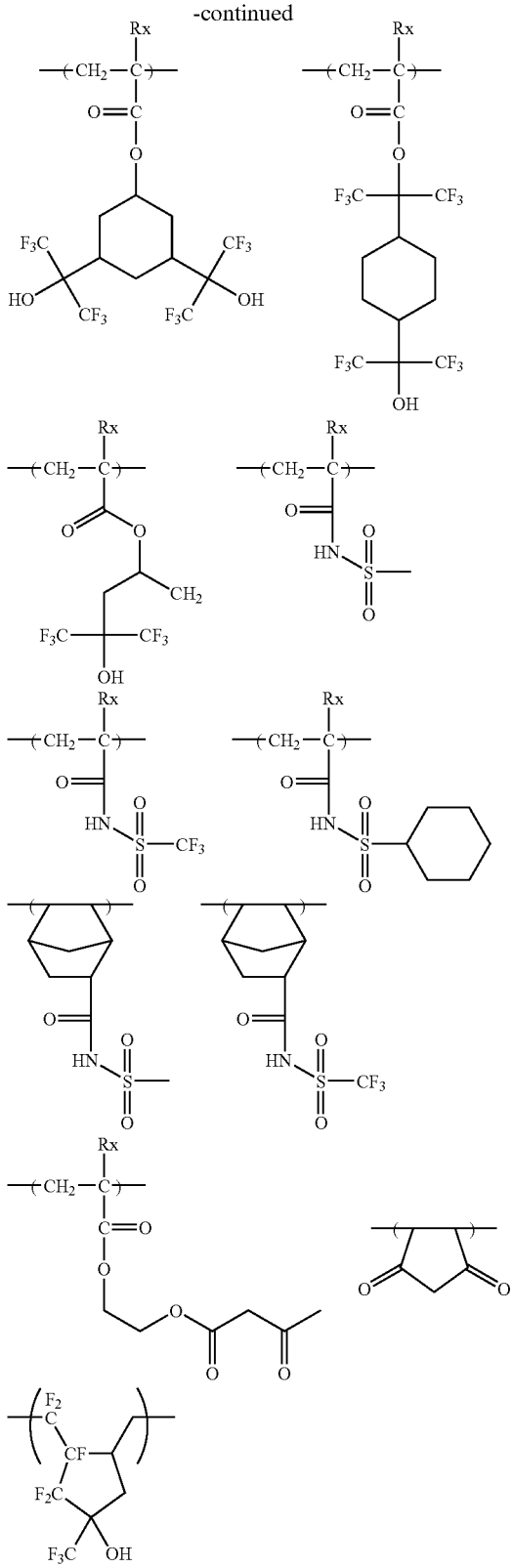

Examples of the (y) group capable of decomposing by the action of an alkali developer to increase the solubility in an alkali developer include a lactone structure-containing group, an acid anhydride group and an acid imide group, with a lactone group being preferred.

As for the repeating unit having (y) a group capable of decomposing by the action of an alkali developer to increase the solubility in an alkali developer, both a repeating unit where (y) a group capable of decomposing by the action of an alkali developer to increase the solubility in an alkali developer is bonded to the main chain of the resin, such as repeating unit by an acrylic acid ester or a methacrylic acid ester, and a repeating unit where (y) a group capable of increasing the solubility in an alkali developer is introduced into the polymer chain terminal by using a polymerization initiator or chain transfer agent containing the group (y) at the polymerization, are preferred.

The content of the repeating unit having (y) a group capable of increasing the solubility in an alkali developer is preferably from 1 to 40 mol %, more preferably from 3 to 30 mol %, still more preferably from 5 to 15 mol %, based on all repeating units in the polymer.

Specific examples of the repeating unit having (y) a group capable of increasing the solubility in an alkali developer are the same as those of the repeating unit having a lactone structure described for the resin as the component (A).

Examples of the repeating unit having (z) a group capable of decomposing by the action of an acid, contained in the hydrophobic resin (HR), are the same as those of the repeating unit having an acid-decomposable group described for the resin as the component (A). In the hydrophobic resin (HR), the content of the repeating unit having (z) a group capable of decomposing by the action of an acid is preferably from 1 to 80 mol %, more preferably from 10 to 80 mol %, still more preferably from 20 to 60 mol %, based on all repeating units in the polymer.

The hydrophobic resin (HR) may further contain a repeating unit represented by the following formula (III):

In formula (III), $R_4$ represents a group having an alkyl group, a cycloalkyl group, an alkenyl group or a cycloalkenyl group.

$L_6$ represents a single bond or a divalent linking group.

In formula (III), the alkyl group of $R_4$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The divalent linking group of $L_6$ is preferably an alkylene group (preferably having a carbon number of 1 to 5) or an oxy group.

In the case where the hydrophobic resin (HR) contains a fluorine atom, the fluorine atom content is preferably from 5 to 80 mass %, more preferably from 10 to 80 mass %, based on the molecular weight of the hydrophobic resin (HR). Also, the fluorine atom-containing repeating unit preferably occupies from 10 to 100 mass %, more preferably from 30 to 100 mass %, in the hydrophobic resin (HR).

In the case where the hydrophobic resin (HR) contains a silicon atom, the silicon atom content is preferably from 2 to 50 mass %, more preferably from 2 to 30 mass %, based on the molecular weight of the hydrophobic resin (HR). Also, the silicon atom-containing repeating unit preferably occupies from 10 to 100 mass %, more preferably from 20 to 100 mass %, in the hydrophobic resin (HR).

The standard polystyrene-equivalent weight average molecular of the hydrophobic resin (HR) is preferably from 1,000 to 100,000, more preferably from 1,000 to 50,000, still more preferably from 2,000 to 15,000.

In the hydrophobic resin (HR), similarly to the resin of the component (A), as well as little impurities such as metal, the content of the residual monomer or oligomer component is preferably from 0 to 10 mass %, more preferably from 0 to 5 mass %, still more preferably from 0 to 1 mass %. When these conditions are satisfied, a resist free of in-liquid foreign matters and sensitivity change with aging can be obtained. Also, in view of resolution, resist profile, side wall of resist pattern, roughness and the like, the molecular weight distribution (Mw/Mn, also called polydispersity) is preferably from 1 to 5, more preferably from 1 to 3, still more preferably from 1 to 2.

As for the hydrophobic resin (HR), various commercial products may be used or the resin may be synthesized by an ordinary method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as tetrahydrofuran, 1,4-dioxane and diisopropyl ether, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate, propylene glycol monomethyl ether and cyclohexanone. The polymerization is more preferably performed using the same solvent as the solvent used in the photosensitive composition of the present invention. By the use of the same solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The reaction concentration is from 5 to 50 mass %, preferably from 30 to 50 mass %, and the reaction temperature is usually from 10 to 150° C., preferably from 30 to 120° C., more preferably from 60 to 100° C.

After the completion of reaction, the reaction solution is allowed to cool to room temperature and purified. The purification may be performed by a normal method, for example, a liquid-liquid extraction method of combining water washing and an appropriate solvent to remove residual monomers or oligomer components; a purification method in a solution sate, such as ultrafiltration of removing by extraction only those having a molecular weight not more than a specific value; a reprecipitation method of adding dropwise the resin solution in a poor solvent to solidify the resin in the poor solvent and thereby remove residual monomers or the like; and a purification method in a solid state, such as washing of a resin slurry separated by filtration with a poor solvent. For example, the resin is precipitated as a solid by contacting the reaction solution with a solvent in which the resin is sparingly soluble or insoluble (poor solvent) and which is in a volumetric amount of 10 times or less, preferably from 10 to 5 times, the reaction solution.

The solvent used at the operation of precipitation or reprecipitation from the polymer solution (precipitation or reprecipitation solvent) may be sufficient if it is a poor solvent to the polymer, and the solvent may be appropriately selected, for example, from a hydrocarbon, a halogenated hydrocarbon, a nitro compound, an ether, a ketone, an ester, a carbonate, an alcohol, a carboxylic acid, water, and a mixed solvent containing such a solvent, according to the kind of the polymer. Among these solvents, a solvent containing at least an alcohol (particularly, methanol or the like) or water is preferred as the precipitation or reprecipitation solvent.

The amount of the precipitation or reprecipitation solvent used may be appropriately selected by taking into consideration the efficiency, yield and the like, but in general, the amount used is from 100 to 10,000 parts by mass, preferably from 200 to 2,000 parts by mass, more preferably from 300 to 1,000 parts by mass, per 100 parts by mass of the polymer solution.

The temperature at the precipitation or reprecipitation may be appropriately selected by taking into consideration the efficiency or operability but is usually on the order of 0 to 50° C., preferably in the vicinity of room temperature (for example, approximately from 20 to 35° C.). The precipitation or reprecipitation operation may be performed using a commonly employed mixing vessel such as stirring tank, by a known method such as batch system and continuous system.

The precipitated or reprecipitated polymer is usually subjected to commonly employed solid-liquid separation such as filtration and centrifugation, then dried and used. The filtration is performed using a solvent-resistant filter element preferably under pressure. The drying is performed under atmospheric pressure or reduced pressure (preferably under reduced pressure) at a temperature of approximately from 30 to 100° C., preferably on the order of 30 to 50° C.

Incidentally, after the resin is once precipitated and separated, the resin may be again dissolved in a solvent and then put into contact with a solvent in which the resin is sparingly soluble or insoluble. That is, there may be used a method comprising, after the completion of radical polymerization reaction, bringing the polymer into contact with a solvent in which the polymer is sparingly soluble or insoluble, to precipitate a resin (step a), separating the resin from the solution (step b), anew dissolving the resin in a solvent to prepare a resin solution A (step c), bringing the resin solution A into contact with a solvent in which the resin is sparingly soluble or insoluble and which is in a volumetric amount of less than 10 times (preferably 5 times or less) the resin solution A, to precipitate a resin solid (step d), and separating the precipitated resin (step e).

Specific examples of the hydrophobic resin (HR) are set forth below. Also, the molar ratio of repeating units (corresponding to repeating units from the left), weight average molecular weight and dispersity of each resin are shown in the table below.

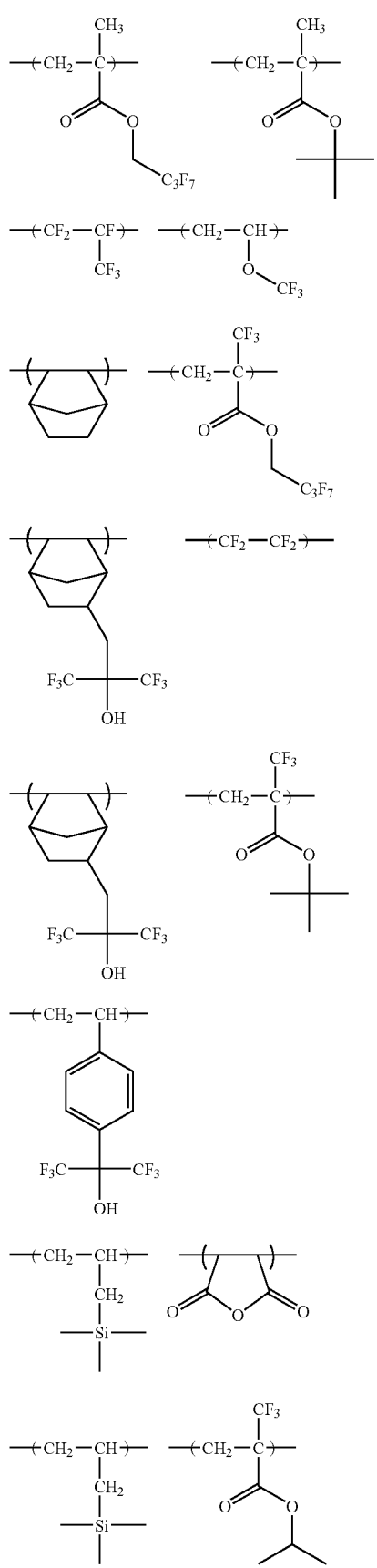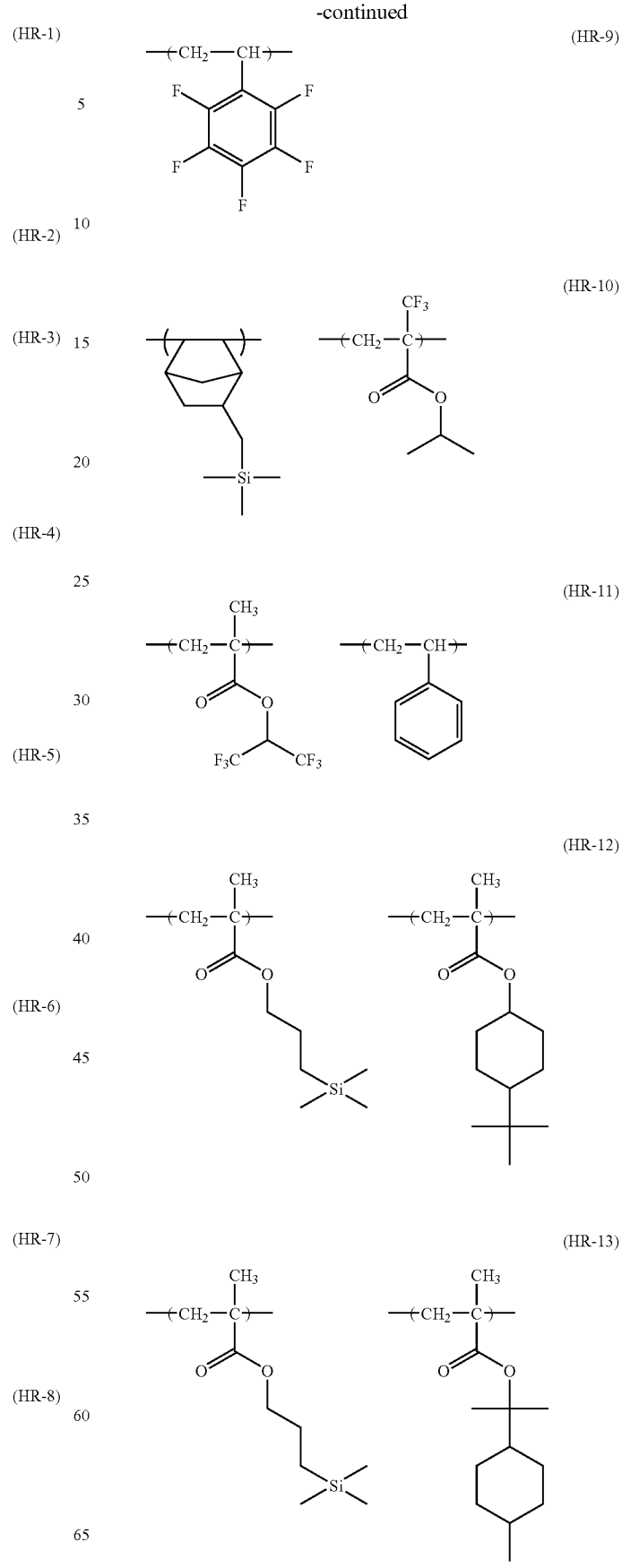

(HR-14)
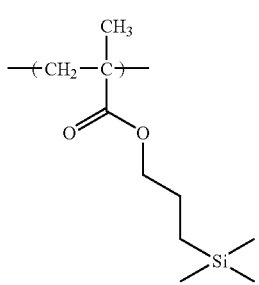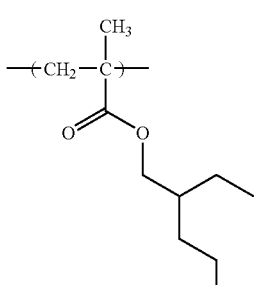
(HR-15)
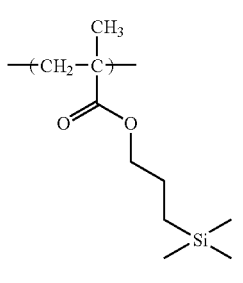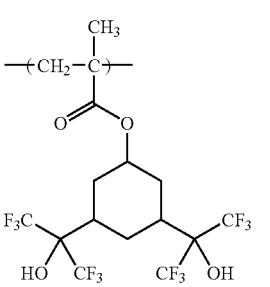
(HR-16)
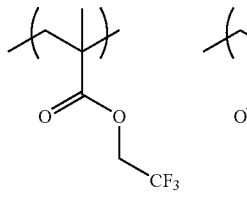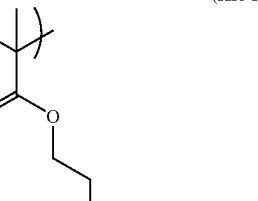
(HR-17)
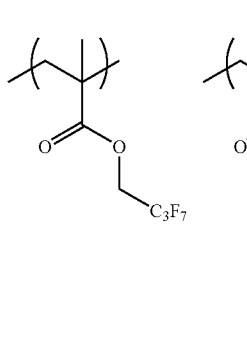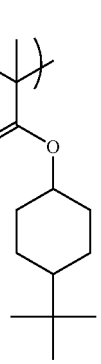
(HR-18)
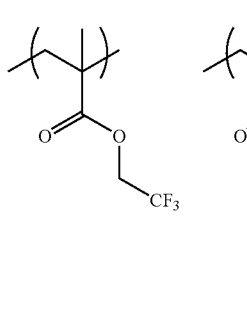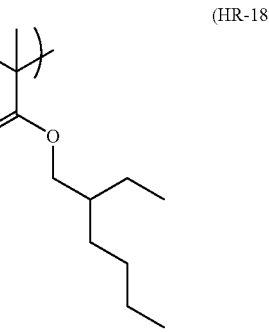
(HR-19)
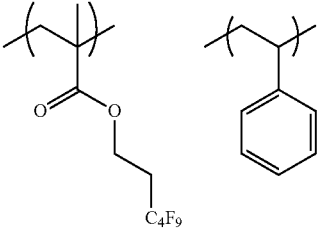
(HR-20)
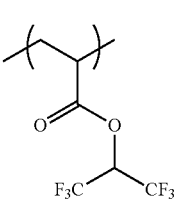
(HR-21)
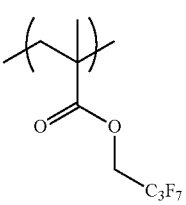
(HR-22)
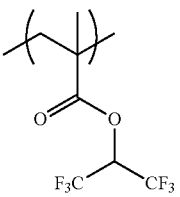
(HR-23)
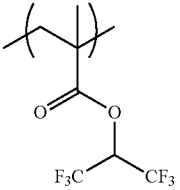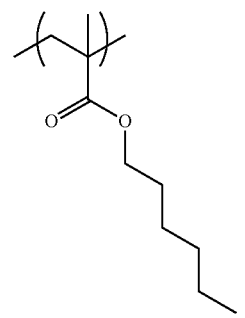
(HR-24)
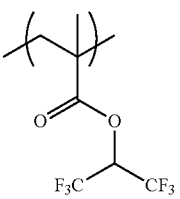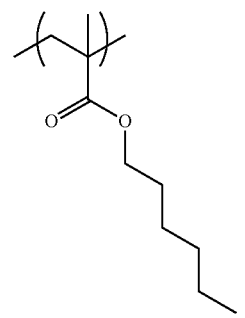

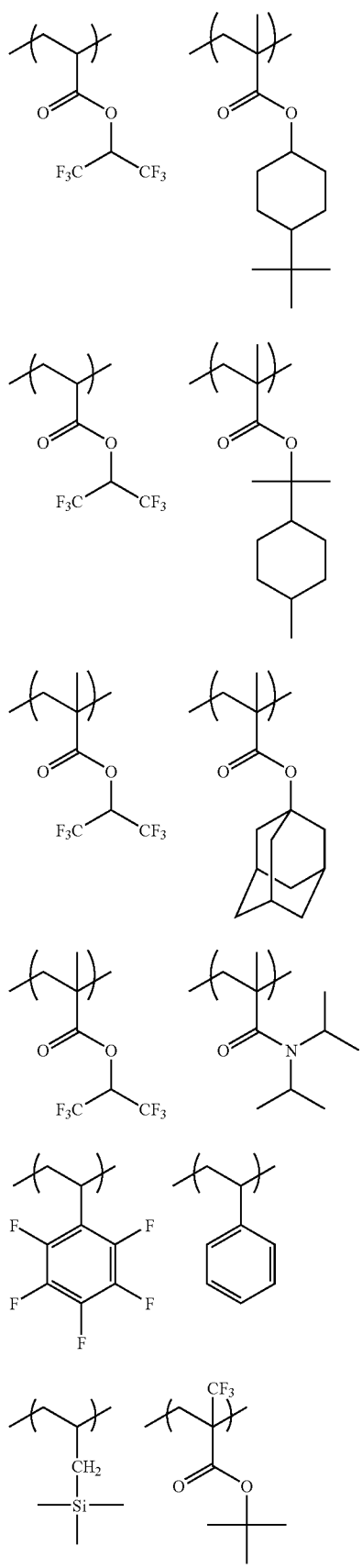
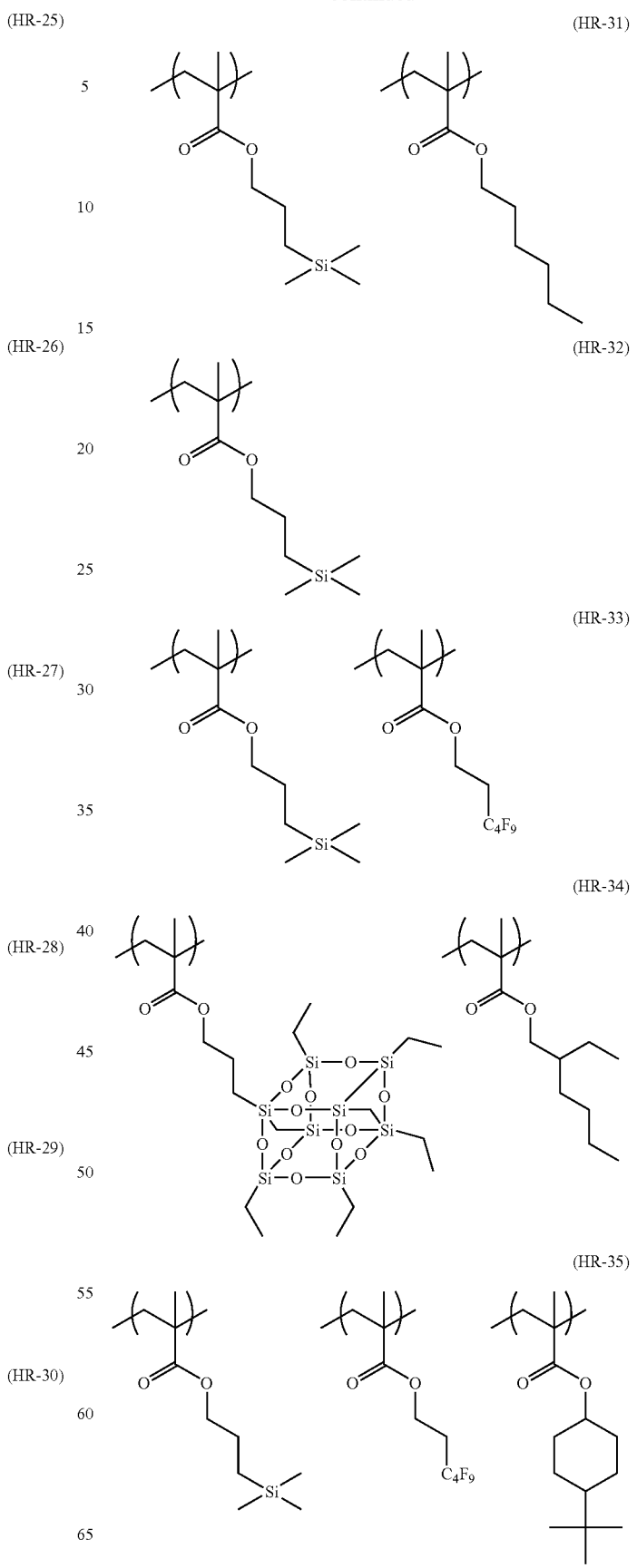

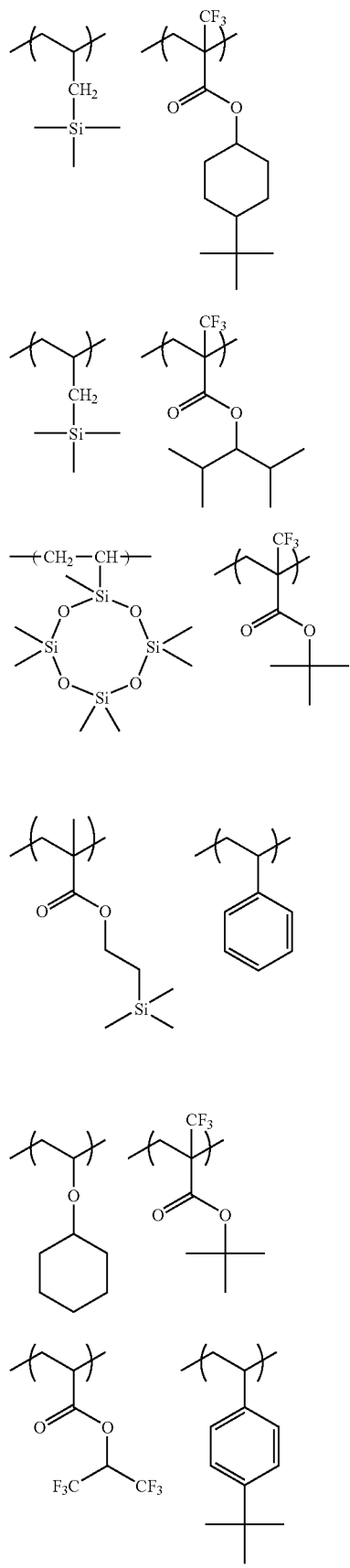
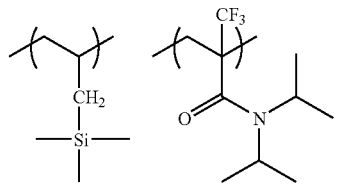
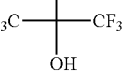

(HR-47) 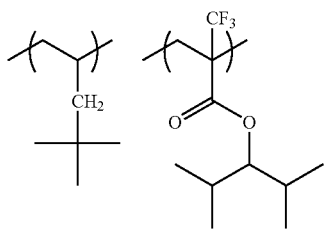
(HR-48) 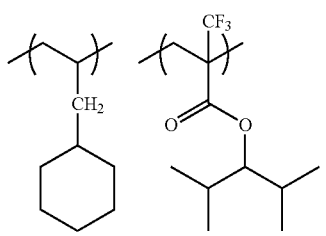
(HR-49) 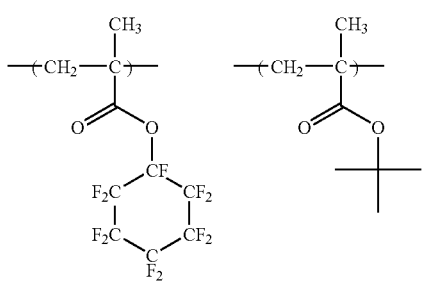
(HR-50) 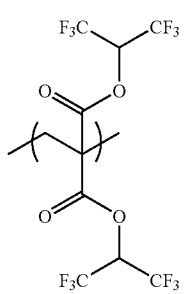
(HR-51) 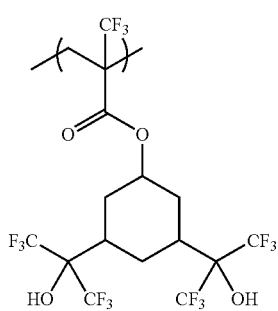
(HR-52) 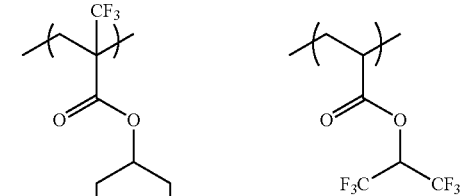
(HR-53) 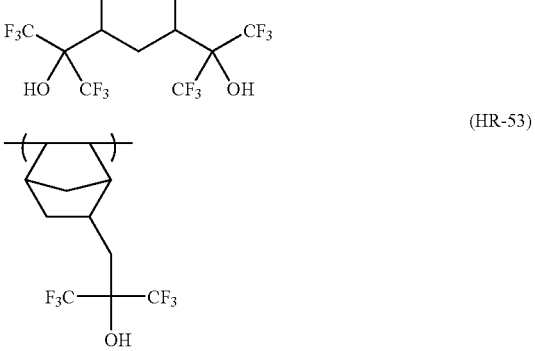
(HR-54) 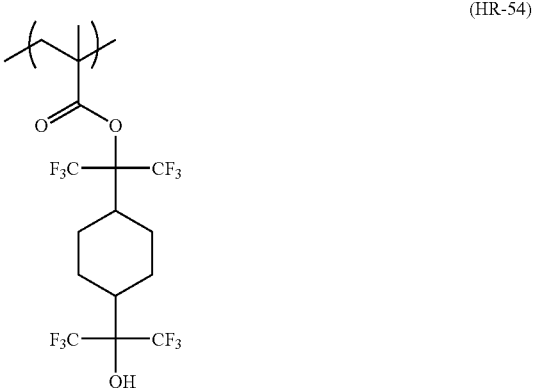
(HR-55) 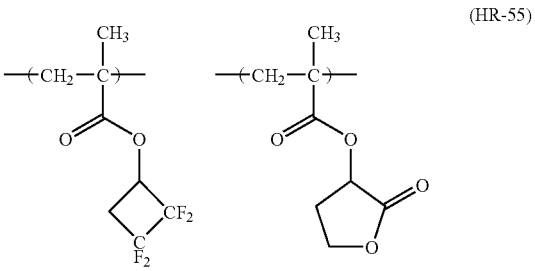
(HR-56) 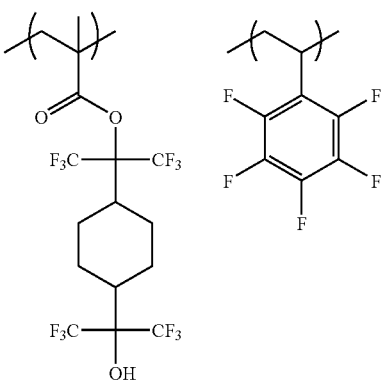

(HR-57)
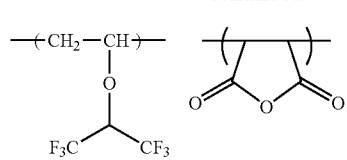
(HR-58)
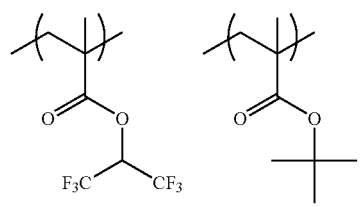
(HR-59)
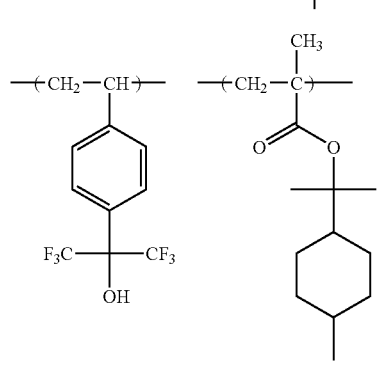
(HR-60)
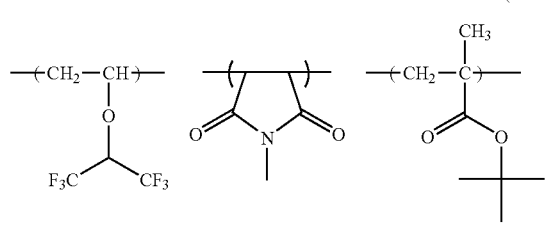
(HR-61)
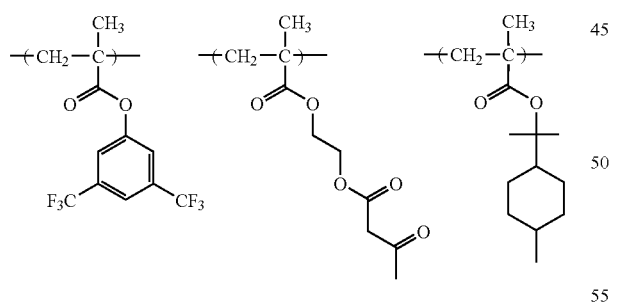
(HR-62)
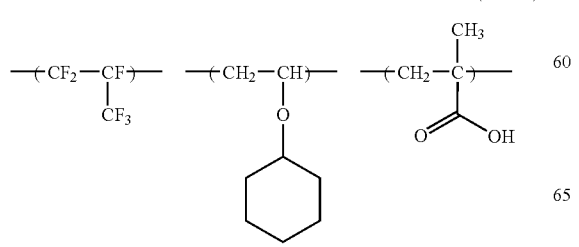
(HR-63)
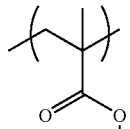
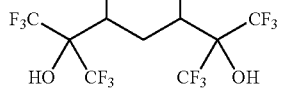
(HR-64)
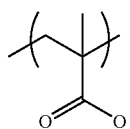 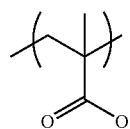
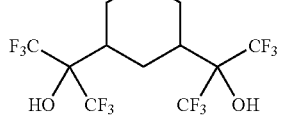
(HR-65)
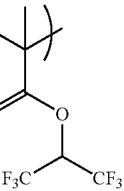 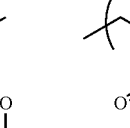
(HR-66)
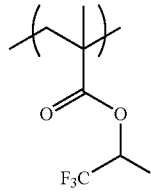 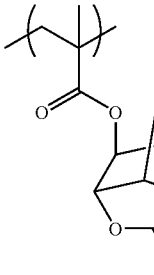
(HR-67)
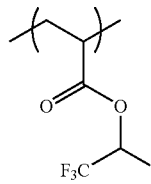 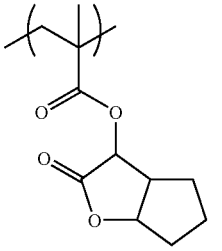

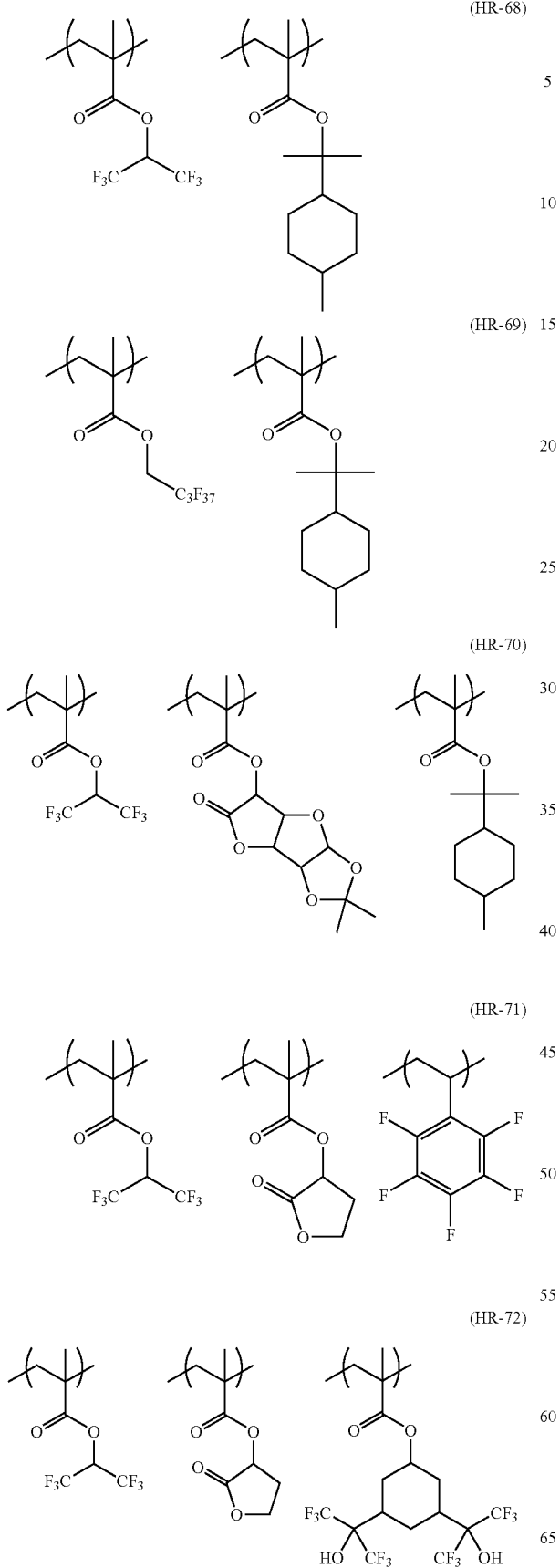
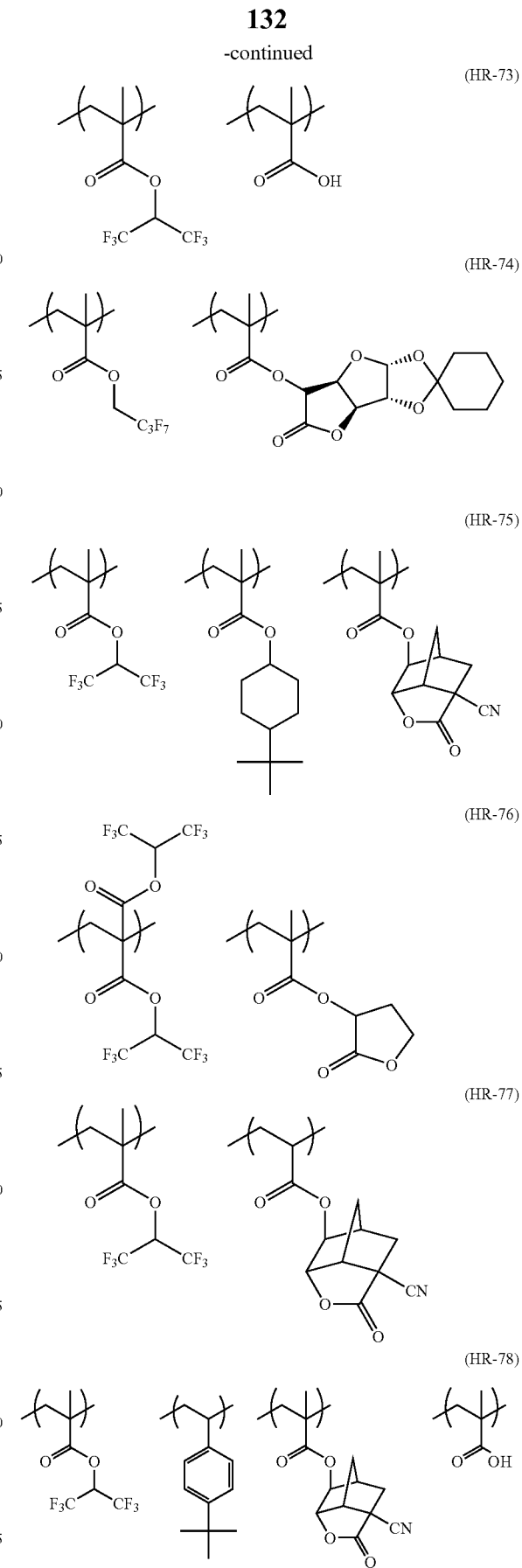

-continued
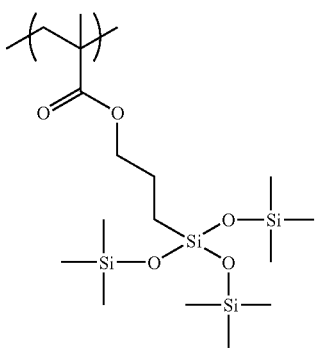
(HR-79)
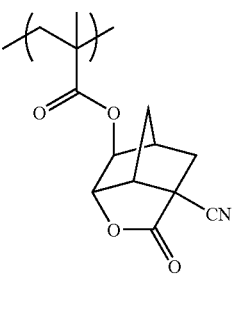
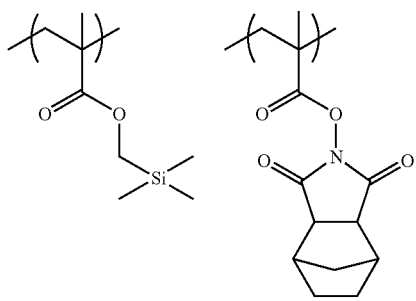
(HR-80)
(HR-81)
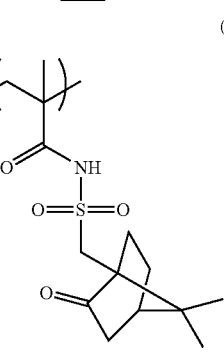
(HR-82)
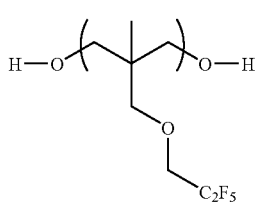
(HR-83)
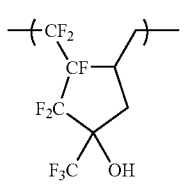
(HR-84)
| Resin | Composition | Mw | Mw/Mn |
|---|---|---|---|
| HR-1 | 50/50 | 8800 | 2.1 |
| HR-2 | 50/50 | 5200 | 1.8 |
| HR-3 | 50/50 | 4800 | 1.9 |
| HR-4 | 50/50 | 5300 | 1.9 |
| HR-5 | 50/50 | 6200 | 1.9 |
| HR-6 | 100 | 12000 | 2.0 |
| HR-7 | 50/50 | 5800 | 1.9 |
| HR-8 | 50/50 | 6300 | 1.9 |
| HR-9 | 100 | 5500 | 2.0 |
| HR-10 | 50/50 | 7500 | 1.9 |
| HR-11 | 70/30 | 10200 | 2.2 |
| HR-12 | 40/60 | 15000 | 2.2 |
| HR-13 | 40/60 | 13000 | 2.2 |
| HR-14 | 80/20 | 11000 | 2.2 |
| HR-15 | 60/40 | 9800 | 2.2 |
| HR-16 | 50/50 | 8000 | 2.2 |
| HR-17 | 50/50 | 7600 | 2.0 |
| HR-18 | 50/50 | 12000 | 2.0 |
| HR-19 | 20/80 | 6500 | 1.8 |
| HR-20 | 100 | 6500 | 1.2 |
| HR-21 | 100 | 6000 | 1.6 |
| HR-22 | 100 | 2000 | 1.6 |
| HR-23 | 50/50 | 6000 | 1.7 |
| HR-24 | 50/50 | 8800 | 1.9 |
| HR-25 | 50/50 | 7800 | 2.0 |
| HR-26 | 50/50 | 8000 | 2.0 |
| HR-27 | 80/20 | 8000 | 1.8 |
| HR-28 | 30/70 | 7000 | 1.7 |
| HR-29 | 50/50 | 6500 | 1.6 |
| HR-30 | 50/50 | 6500 | 1.6 |
| HR-31 | 50/50 | 9000 | 1.8 |
| HR-32 | 100 | 10000 | 1.6 |
| HR-33 | 70/30 | 8000 | 2.0 |
| HR-34 | 10/90 | 8000 | 1.8 |
| HR-35 | 30/30/40 | 9000 | 2.0 |
| HR-36 | 50/50 | 6000 | 1.4 |
| HR-37 | 50/50 | 5500 | 1.5 |
| HR-38 | 50/50 | 4800 | 1.8 |
| HR-39 | 60/40 | 5200 | 1.8 |
| HR-40 | 50/50 | 8000 | 1.5 |
| HR-41 | 20/80 | 7500 | 1.8 |
| HR-42 | 50/50 | 6200 | 1.6 |
| HR-43 | 60/40 | 16000 | 1.8 |
| HR-44 | 80/20 | 10200 | 1.8 |
| HR-45 | 50/50 | 12000 | 2.6 |
| HR-46 | 50/50 | 10900 | 1.9 |
| HR-47 | 50/50 | 6000 | 1.4 |
| HR-48 | 50/50 | 4500 | 1.4 |
| HR-49 | 50/50 | 6900 | 1.9 |
| HR-50 | 100 | 2300 | 2.6 |
| HR-51 | 60/40 | 8800 | 1.5 |
| HR-52 | 68/32 | 11000 | 1.7 |
| HR-53 | 100 | 8000 | 1.4 |
| HR-54 | 100 | 8500 | 1.4 |
| HR-55 | 80/20 | 13000 | 2.1 |
| HR-56 | 70/30 | 18000 | 2.3 |
| HR-57 | 50/50 | 5200 | 1.9 |
| HR-58 | 50/50 | 10200 | 2.2 |
| HR-59 | 60/40 | 7200 | 2.2 |
| HR-60 | 32/32/36 | 5600 | 2.0 |
| HR-61 | 30/30/40 | 9600 | 1.6 |
| HR-62 | 40/40/20 | 12000 | 2.0 |
| HR-63 | 100 | 6800 | 1.6 |
| HR-64 | 50/50 | 7900 | 1.9 |
| HR-65 | 40/30/30 | 5600 | 2.1 |
| HR-66 | 50/50 | 6800 | 1.7 |
| HR-67 | 50/50 | 5900 | 1.6 |
| HR-68 | 49/51 | 6200 | 1.8 |
| HR-69 | 50/50 | 8000 | 1.9 |
| HR-70 | 30/40/30 | 9600 | 2.3 |
| HR-71 | 30/40/30 | 9200 | 2.0 |
| HR-72 | 40/29/31 | 3200 | 2.1 |
| HR-73 | 90/10 | 6500 | 2.2 |
| HR-74 | 50/50 | 7900 | 1.9 |
| HR-75 | 20/30/50 | 10800 | 1.6 |
| HR-76 | 50/50 | 2200 | 1.9 |
| HR-77 | 50/50 | 5900 | 2.1 |
| HR-78 | 40/20/30/10 | 14000 | 2.2 |
| HR-79 | 50/50 | 5500 | 1.8 |

-continued

| Resin | Composition | Mw | Mw/Mn |
|---|---|---|---|
| HR-80 | 50/50 | 10600 | 1.9 |
| HR-81 | 50/50 | 8600 | 2.3 |
| HR-82 | 100 | 15000 | 2.1 |
| HR-83 | 100 | 6900 | 2.5 |
| HR-84 | 50/50 | 9900 | 2.3 |

In order to prevent the photosensitive film from directly contacting with the immersion liquid, a film (hereinafter, sometimes referred to as a "topcoat") sparingly soluble in the immersion liquid may be provided between the photosensitive film formed of the photosensitive composition of the present invention and the immersion liquid. The functions required of the topcoat are suitability for coating as an overlayer of the resist, transparency to radiation particularly at 193 nm, and scarce solubility in the immersion liquid. The topcoat is preferably unmixable with the resist and capable of being uniformly applied as an overlayer of the resist.

In view of transparency to light at 193 nm, the topcoat is preferably a polymer not abundantly containing an aromatic, and specific examples thereof include a hydrocarbon polymer, an acrylic acid ester polymer, a polymethacrylic acid, a polyacrylic acid, a polyvinyl ether, a silicon-containing polymer and a fluorine-containing polymer. The above-described hydrophobic resin (HR) is suitable also as the topcoat. If impurities are dissolved out into the immersion liquid from the topcoat, the optical lens is contaminated. In this viewpoint, the amount of residual monomer components of the polymer contained in the topcoat is preferably smaller.

On peeling off the topcoat, a developer may be used or a releasing agent may be separately used. The releasing agent is preferably a solvent less permeating into the photosensitive film. From the standpoint that the peeling step can be performed simultaneously with the development step of the photosensitive film, the topcoat is preferably peelable with an alkali developer and in terms of peeling with an alkali developer, the topcoat is preferably acidic, but in view of nonintermixing with the photosensitive film, the topcoat may be neutral or alkaline.

With no difference in the refractive index between the topcoat and the immersion liquid, the resolution is enhanced. At the exposure with ArF excimer laser (wavelength: 193 nm), when water is used as the immersion liquid, the topcoat for ArF immersion exposure preferably has a refractive index close to the refractive index of the immersion liquid. From the standpoint of approximating the refractive index to that of the immersion liquid, the topcoat preferably contains a fluorine atom. Also, in view of transparency and refractive index, the topcoat is preferably a thin film.

The topcoat is preferably unmixable with the photosensitive film and further unmixable with the immersion liquid. From this standpoint, when the immersion liquid is water, the topcoat solvent is preferably a medium that is sparingly soluble in the solvent used for the photosensitive composition and insoluble in water. Furthermore, when the immersion liquid is an organic solvent, the topcoat may be either water-soluble or water-insoluble.

The pattern forming method according to an embodiment of the present invention comprises steps of forming a photosensitive film from the photosensitive composition of the present invention, and subjecting the photosensitive film to double exposure and development.

The pattern forming method according to an embodiment of the present invention comprises steps of forming a photosensitive film from the photosensitive composition of the present invention, and subjecting the photosensitive film to immersion double exposure and development.

Furthermore, the pattern forming method according to an embodiment of the present invention comprises steps of forming a photosensitive film from the photosensitive composition of the present invention, further forming a surface hydrophobizing resin as an overlayer of the photosensitive film, and subjecting the photosensitive film to immersion double exposure and development. The double exposure process as used in the present invention is, as described in JP-A-2002-75857, a process of performing exposure twice on the same photosensitive film, which is a method of dividing the pattern in the exposure field into two pattern groups and performing the exposure in twice for respective pattern groups divided. In the specific dividing method, as shown in FIG. 1, two masks having a pattern of 60-nm line and 180-nm space are used and exposure is performed twice by displacing the masks by 120 nm to form a 60-nm 1:1 line-and-space pattern. In general, as the pitch of the pattern (in the 60-nm 1:1 line-and-space pattern, the pitch is 120 nm) becomes narrow, the optical resolution decreases. However, in the double exposure, the divided respective patterns come to give a pitch of 2 times the pitch in the original pattern and the resolution is enhanced.

The photosensitive composition of the present invention may be applied to a multilayer resist process (particularly, a three-layer resist process). The multilayer resist process comprises the following steps:

(a) forming a lower resist layer comprising an organic material on a to-be-processed substrate, (b) sequentially stacking on the lower resist layer an intermediate layer and an upper resist layer comprising an organic material capable of crosslinking or decomposing upon irradiation with radiation, and (c) forming a predetermined pattern on the upper resist layer and then sequentially etching the intermediate layer, the lower layer and the substrate.

An organopolysiloxane (silicone resin) or $SiO_2$ coating solution (SOG) is generally used for the intermediate layer. As for the lower layer resist, an appropriate organic polymer film is used, but various known photoresists may be used. Examples thereof include various series such as FH Series and FHi Series produced by Fujifilm Arch Co., Ltd., and PFI Series produced by Sumitomo Chemical Co., Ltd.

The film thickness of the lower resist layer is preferably from 0.1 to 4.0 μm, more preferably from 0.2 to 2.0 μm, still more preferably from 0.25 to 1.5 μm. The film thickness is preferably 0.1 μm or more in view of antireflection or dry etching resistance and preferably 4.0 μm or less in view of aspect ratio or pattern collapse of the fine pattern formed.

EXAMPLES

The present invention is described in greater detail below by referring to Examples, but the present invention should not be construed as being limited thereto.

Synthesis Example 1

Synthesis of Compound A-2

6.32 Gram of 4-hydroxybenzoic acid was dissolved in 100 mL of N-methylpyrrolidone, 6.96 g of diaza(1,3)bicyclo [5.4.0]undecane was added thereto, and the resulting mixture was cooled to 0° C. in a nitrogen stream. Thereto, 50 mL of an N-methylpyrrolidone solution having dissolved therein 15 g of 1,12-dibromododecane was added dropwise over 0.2 hours, and the obtained reaction solution was stirred at 0° C. for 2 hours and further stirred at 50° C. for 4 hours. After adding 200 mL of ethyl acetate, the organic layer was washed, in sequence, twice with an aqueous saturated sodium hydrogencarbonate solution and twice with water and dried over sodium sulfate. The solvent was concentrated, and the residue was purified by column chromatography ($SiO_2$, hexane/ethyl acetate=2/1) to obtain 10.2 g of 12-bromododecyl 4-hydroxybenzoate as a transparent oil. Thereafter, 4.62 g of the oil and 3.79 g of 1,1,2,2,3,3-hexafluoropropane-1,3-disulfonyl difluoride were dissolved in 100 mL of acetonitrile, and the resulting solution was cooled to 0° C. Thereto, 50 mL of an acetonitrile solution having dissolved therein 1.83 g of diaza (1,3)bicyclo[5.4.0]undecane was added dropwise over 0.5 hours, and the obtained reaction solution was stirred at 0° C. for 1 hour and further stirred at room temperature for 3 hours. After adding 200 mL of ethyl acetate, the organic layer was washed, in sequence, twice with an aqueous saturated sodium hydrogencarbonate solution and twice with water and dried over sodium sulfate. The solvent was concentrated, and the transparent oil as residue was dissolved in a mixed solution of 100 ml of methanol and 50 ml of acetone. Thereto, 10 g of sodium hydrogencarbonate as solid was added, and the mixture was stirred at 40° C. for 5 hours. After adding 200 mL of ethyl acetate, the organic layer was washed, in sequence, twice with saturated brine and twice with water and dried over sodium sulfate. The residue was recrystallized from hexane to obtain 5.0 g of sodium 3-((4-((12-bromododecyloxy)carbonyl)phenoxy)sulfonyl)-1,1,2,2,3,3-hexafluoropropane-1-sulfonate as a white solid. Thereafter, 3.0 g of this solid was dissolved in 100 mL of acetonitrile, and 0.81 g of methacrylic acid, 1.44 g of diaza(1,3)bicyclo[5.4.0]undecane and 50 mL of methanol were sequentially added thereto, followed by stirring at 70° C. for 3 hours in a nitrogen stream. After adding 200 mL of ethyl acetate, the organic layer was washed, in sequence, twice with an aqueous saturated sodium hydrogencarbonate solution and twice with water and dried over sodium sulfate. The solvent was concentrated to obtain 2.82 g of sodium 3-((4-((12-(methacryloyloxy)dodecyloxy)carbonyl)phenoxy)sulfonyl)-1,1,2,2,3,3-hexafluoropropane-1-sulfonate. Furthermore, 3.64 g of this solid was dissolved in 50 mL of methanol, and 1.77 g of triphenylsulfonium bromide was added thereto, followed by stirring at room temperature for 3 hours. After adding 200 mL of chloroform, the organic layer was washed with water, and the solvent was concentrated, as a result, 4.1 g of a transparent oily compound was obtained. $^1$H-NMR (300 MHz, $CDCl_3$) δ 1.26-1.45 (m, 14H), 1.67 (m, 2H), 1.76 (quintet, 2H), 1.94 (s, 3H), 4.13 (m, 4H), 4.32 (t, 2H), 5.54 (s, 1H), 6.09 (s, 1H), 7.55 (d, 2H), 7.69-7.78 (m, 15H), 8.11 (d, 2H), $^{19}$F-NMR (300 MHz, $CDCl_3$) δ -107.0 (m, 2F), -114.0 (m, 2F), -118.4 (m, 2F).

Synthesis Example 2

Synthesis of Compound A-18

12.4 Gram of 4-(2-aminoethyl)phenol and 9.15 g of triethylamine were dissolved in 100 mL of N-methylpyrrolidone, and the solution was cooled to 0° C. in a nitrogen stream. Thereto, 9.45 g of methacryloyl chloride was added dropwise over 0.2 hours, and the obtained reaction solution was stirred at 0° C. for 1 hour and further stirred at room temperature for 4 hours. After adding 500 mL of ethyl acetate, the organic layer was washed, in sequence, twice with an aqueous saturated sodium hydrogencarbonate solution and twice with water and dried over sodium sulfate. The solvent was concentrated to obtain 12.2 g of N-(4-hydroxyphenethyl) methacrylamide as a brown oil. Thereafter, 7.49 g of the oil and 11.5 g of 1,1,2,2,3,3-hexafluoropropane-1,3-disulfonyl difluoride were dissolved in 100 mL of THF, and the resulting solution was cooled to 0° C. Thereto, 4.43 g of triethylamine was added dropwise over 0.3 hours, and the obtained reaction solution was stirred at 0° C. for 1 hour and further stirred at room temperature for 3 hours. After adding 200 mL of ethyl acetate, the organic layer was washed, in sequence, twice with an aqueous saturated sodium hydrogencarbonate solution and twice with water and dried over sodium sulfate. The solvent was concentrated, and the brown oil as residue was dissolved in 100 ml of methanol. Thereto, 10 g of sodium hydrogencarbonate as solid was added, and the mixture was stirred at 50° C. for 6 hours. After adding 200 mL of ethyl acetate, the organic layer was washed, in sequence, twice with saturated brine and twice with water and dried over sodium sulfate to obtain 15.7 g of 3-((4-(2-methacrylamido)ethyl)phenoxy) sulfonyl)-1,1,2,2,3,3-hexafluoropropane-1-sulfonylfluoride as a brown oil. Thereafter, 7.29 g of this brown oil was dissolved in 100 mL of methanol, and 4.81 g of triphenylsulfonium bromide was added thereto, followed by stirring at room temperature for 3 hours. After adding 200 mL of chloroform, the organic layer was washed with water, and the solvent was concentrated, as a result, 10.1 g of a brown transparent oily compound was obtained. $^1$H-NMR (300 MHz, $CDCl_3$) δ 1.91 (s, 3H), 2.87 (t, 2H), 3.50 (quartet, 2H), 5.27 (s, 1H), 5.66 (s, 1H), 6.39 (bs, 1H), 7.14 (d, 2H), 7.23 (d, 2H), 7.67-7.76 (m, 15H), $^{19}$F-NMR (300 MHz, $CDCl_3$) δ -107.4 (m, 2F), -114.0 (m, 2F), -118.1 (m, 2F).

Synthesis Example 3

Synthesis of Compound A-46

6.95 Gram of N-(4-hydroxyphenethyl)methacrylamide and 10.7 g of 1,1,2,2,3,3-hexafluoropropane-1,3-disulfonyldifluoride were dissolved in 80 mL of THF, and 80 mL of triethylamine was added thereto. The resulting mixture was stirred at 50° C. for 2 hours, and 5.56 g of trifluoromethanesulfonamide was added thereto. The mixture was further stirred at 80° C. for 4 hours. After adding 200 mL of ethyl acetate, the organic layer was washed, in sequence, twice with dilute hydrochloric acid and twice with water and dried over sodium sulfate. The solvent was concentrated, and the brown oil as residue was dissolved in 200 ml of methanol. Thereto, 10 g of sodium hydrogencarbonate as solid was added, and the mixture was stirred at 50° C. for 4 hours. After adding 200 mL of ethyl acetate, the organic layer was washed, in sequence, twice with saturated brine and twice with water and dried over sodium sulfate to obtain 12.2 g of N-(trifluoromethanesulfonyl)-1,1,2,2,3,3-hexafluoro-3-((4-(2-(methacrylamido)ethyl)phenoxy)sulfonyl)-1-propanesulfonamide solution salt as a brown oil. Thereafter, 12.2 g of this brown oil was dissolved in 100 mL of methanol, and 6.43 g of triphenylsulfonium bromide was added thereto, followed by stirring at room temperature for 3 hours. After adding 200 mL of chloroform, the organic layer was washed with water, and the solvent was concentrated, as a result, 14.0 g of a brown transparent oily compound was obtained. $^1$H-NMR (300 MHz, $CDCl_3$) δ 1.91 (s, 3H), 2.87 (t, 2H), 3.50 (quartet, 2H), 5.28 (s, 1H), 5.66 (s, 1H), 6.05 (bs, 1H), 7.20 (d, 2H), 7.27 (d, 2H), 7.63-7.77 (m, 15H), $^{19}$F-NMR (300 MHz, $CDCl_3$) δ -78.65 (s, 3F), -107.8 (m, 2F), -112.4 (t, 2F), -118.0 (m, 2F).

Synthesis Example 4

Synthesis of Compound A-116

10.0 Gram (43.4 mmol) of 2-methacryloyloxyethyl succinate, 10.0 g (52.1 mmol) of 1-ethyl-3-(3-dimethylaminopropyl)carbodiimide hydrochloride and 7.04 g (52.1 mmol) of 1-hydroxy-1H-benzotriazole were dissolved in 120 mL of N,N-dimethylformamide, and the resulting solution was cooled to 0° C. in a nitrogen stream and stirred for 0.5 hours. Subsequently, 5.95 g (43.4 mmol) of 4-(2-aminoethyl)phenol was added thereto, and the mixture was stirred at room temperature for 1 hour and further stirred at 60° C. for 4 hours. After adding 200 mL of ethyl acetate, the organic layer was washed, in sequence, three times with an aqueous saturated sodium hydrogencarbonate solution and twice with water and dried over sodium sulfate. The solvent was concentrated to obtain 14.0 g of 2-methacryloyloxyethyl 3-(4-hydroxyphenethylcarbamoyl)propanoate as a brown oil. Thereafter, 6.7 g (19.18 mmol) of this oil and 7.28 g (23.02 mmol) of 1,1,2,2,3,3-hexafluoropropane-1,3-disulfonyl difluoride were dissolved in 100 mL of tetrahydrofuran (THF), and the resulting solution was cooled to 0° C. Thereto, 2.91 g of triethylamine was added dropwise over 0.3 hours, and the obtained reaction solution was stirred at 0° C. for 1 hour and further stirred at room temperature for 12 hours. Thereafter, 50 mL of triethylamine and 5.72 g (38.36 mmol) of trifluoromethanesulfonamide were added thereto, and the mixture was stirred at 50° C. for 4 hours. After adding 200 mL of ethyl acetate, the organic layer was washed, in sequence, twice with dilute hydrochloric acid and twice with water and dried over sodium sulfate. The solvent was concentrated, and the residue was purified by column chromatography ($SiO_2$, ethyl acetate) to obtain 14.4 g of a brown oil. This brown oil was dissolved in 50 mL of methanol, and 5.64 g of triphenylsulfonium bromide was added thereto, followed by stirring at room temperature for 3 hours. After adding 200 mL of chloroform, the organic layer was washed with water, the solvent was concentrated, and the residue was purified by column chromatography ($SiO_2$, ethyl acetate/methanol=6/1), as a result, 8.16 g of a brown transparent oily compound was obtained. $^1$H-NMR (300 MHz, $CDCl_3$) δ 1.93 (s, 3H), 2.45 (t, 2H), 2.65 (t, 2H), 2.82 (t, 2H), 3.44 (q, 2H), 4.32 (bs, 4H), 5.58 (s, 1H), 6.08 (t, 1H), 6.11 (s, 1H), 7.15 (d, 2H), 7.23 (d, 2H), 7.62-7.79 (m, 15H), $^{19}$F-NMR (300 MHz, $CDCl_3$) δ −78.7 (s, 3F), −107.8 (m, 2F), −112.4 (t, 2F), −118.0 (m, 2F).

Other compounds represented by formula (I) were synthesized in the same manner.

Synthesis Example of Polymer

Synthesis Example 5

Synthesis of Resin (P-1)

In a nitrogen stream, 11.27 g of cyclohexanone was charged into a three-neck flask and heated at 80° C. Thereto, a solution obtained by dissolving 7.80 g of norbornane lactone methacrylate, 3.56 g of 3-hydroxyadamantyl methacrylate, 7.31 g of 1-ethyl-cyclopentyl methacrylate, 9.50 g of Compound (A-2), 2.03 g of 1-dodecanethiol and 1.15 g of polymerization initiator V-601 (produced by Wako Pure Chemical Industries, Ltd.) in 101.4 g of cyclohexanone was added dropwise over 6 hours. After the completion of dropwise addition, the reaction was further allowed to proceed at 80° C. for 2 hours. The resulting reaction solution was left standing to cool and then, added dropwise to a mixed solution of 900 ml of hexane/100 ml of ethyl acetate over 20 minutes, and the powder precipitated was collected by filtration and dried, as a result, 21.2 g of Resin (P-1) was obtained. The weight average molecular weight of the obtained resin was 2,000 in terms of standard polystyrene and the polydispersity (Mw/Mn) was 1.2.

Synthesis Example 6

Synthesis of Resin (P-6)

In a nitrogen stream, 4.10 g of cyclohexanone was charged into a three-neck flask and heated at 80° C. Thereto, a solution obtained by dissolving 3.56 g of 4-oxa-5-oxo-6-cyanotricyclo[4.2.1.0<3.7>]non-2-yl 2-methylprop-2-enoate, 0.91 g of 3,5-dihydroxy-1-adamantyl 2-methylprop-2-enoate, 3.03 g of 2-cyclohexylpropan-2-yl methacrylate, 2.74 g of Compound (A-18) and 0.66 g of polymerization initiator V-601 (produced by Wako Pure Chemical Industries, Ltd.) in 36.9 g of cyclohexanone was added dropwise over 6 hours. After the completion of dropwise addition, the reaction was further allowed to proceed at 80° C. for 2 hours. The resulting reaction solution was left standing to cool and then, added dropwise to a mixed solution of 400 ml of hexane/100 ml of ethyl acetate over 20 minutes, and the powder precipitated was collected by filtration. The obtained powder was dissolved in 30.5 g of cyclohexanone, and the solution was added dropwise to a mixed solution of 400 ml of methanol/100 ml of water over 20 minutes. The powder precipitated was collected by filtration and dried, as a result, 7.21 g of Resin (P-6) was obtained. The weight average molecular weight of the obtained resin was 3,500 in terms of standard polystyrene and the polydispersity (Mw/Mn) was 1.3.

Synthesis Example 7

Synthesis of Resin (P-11)

In a nitrogen stream, 13.9 g of cyclohexanone was charged into a three-neck flask and heated at 80° C. Thereto, a solution obtained by dissolving 25.66 g of 10,10-dimethyl-3,7,9,11-tetraoxa-4-oxotricyclo[6.4.0.0<2,6>]undec-5-yl 2-methylprop-2-enoate, 8.96 g of Compound (A-46) and 1.85 g of polymerization initiator V-601 (produced by Wako Pure Chemical Industries, Ltd.) in 124.6 g of cyclohexanone was added dropwise over 6 hours. After the completion of dropwise addition, the reaction was further allowed to proceed at 80° C. for 2 hours. The resulting reaction solution was left standing to cool and then, added dropwise to 2,000 ml of methanol over 60 minutes, and the powder precipitated was collected by filtration and dried, as a result, 25.6 g of Resin (P-11) was obtained. The weight average molecular weight of the obtained resin was 10,000 in terms of standard polystyrene and the polydispersity (Mw/Mn) was 1.8.

Synthesis Example 8

Synthesis of Resin (P-24)

In a nitrogen stream, 4.37 g of cyclohexanone was charged into a three-neck flask and heated at 80° C. Thereto, a solution obtained by dissolving 3.462 g of 4-oxa-5-oxo-6-cyanotricyclo[4.2.1.0<3.7>]non-2-yl 2-methylprop-2-enoate, 0.883 g of 3,5-dihydroxy-1-adamantyl 2-methylprop-2-enoate, 2.944 g of 2-cyclohexylpropan-2-yl methacrylate, 3.629 g of Compound (A-116) and 0.6447 g of polymerization initiator V-601 (produced by Wako Pure Chemical Industries, Ltd.) in 39.3 g of cyclohexanone was added dropwise over 6 hours. After the completion of dropwise addition, the reaction was further allowed to proceed at 80° C. for 2 hours. The resulting reaction solution was left standing to cool and then, added dropwise to 500 ml of hexane over 20 minutes, and the powder precipitated was collected by filtration. The obtained powder was added to 500 ml of methanol, and the mixture was stirred for 90 minutes. The powder was collected by filtration and dried, as a result, 7.11 g of Resin (P-24) was obtained. The weight average molecular weight of the obtained resin was 5,000 in terms of standard polystyrene and the polydispersity (Mw/Mn) was 1.4.

Other resins were synthesized in the same manner.

Regarding Resins (P-1) to (P-28) of the component (A) and Resins (1) to (23) of the component (A') as a resin used in combination, which were used in Examples, the monomers used for the synthesis of each resin, the compositional ratio, the weight average molecular weight and the polydispersity are shown in Tables 2 and 3 below.

TABLE 2

| Resin | Monomer (1) | Monomer (2) | Monomer (3) | Monomer (4) | Compositional Ratio (by mol) | Mw | Mw/Mn |
|---|---|---|---|---|---|---|---|
| P-1 | (structure) | (structure with OH) | (structure) | A-2 | 35/15/40/10 | 2000 | 1.2 |
| P-2 | (structure) | A-18 | | | 90/10 | 3700 | 1.3 |
| P-3 | (structure) | (structure with OH) | A-83 | | 50/40/10 | 3600 | 1.4 |
| P-4 | (structure) | (structure) | A-2 | | 30/50/20 | 5600 | 1.6 |

TABLE 2-continued

| Resin | Monomer (1) | Monomer (2) | Monomer (3) | Monomer (4) | Compositional Ratio (by mol) | Mw | Mw/Mn |
|---|---|---|---|---|---|---|---|
| P-5 | (methacrylate with 2-cyclohexylpropan-2-yl ester) | A-46 | | | 90/10 | 29000 | 2.0 |
| P-6 | (methacrylate with cyanolactone norbornane) | (methacrylate with dihydroxyadamantane) | (methacrylate with 2-cyclohexylpropan-2-yl ester) | A-18 | 40/10/40/10 | 3500 | 1.3 |
| P-7 | (methacrylate with cyanolactone norbornane) | (methacrylate with dihydroxyadamantane) | (methacrylic acid) | A-46 | 40/20/30/10 | 7500 | 1.8 |
| P-8 | (methacrylate with tricyclodecanyl group) | (methacrylate with hydroxyadamantane) | (methacrylate with 2-adamantylpropan-2-yl ester) | A-105 | 30/30/10/30 | 4600 | 1.5 |
| P-9 | (acrylate with lactone norbornane) | (methacrylate with dihydroxyadamantane) | (methacrylate with 2-adamantylpropan-2-yl ester) | A-111 | 40/20/30/10 | 1500 | 1.2 |

TABLE 2-continued

| Resin | Monomer (1) | Monomer (2) | Monomer (3) | Monomer (4) | Compositional Ratio (by mol) | Mw | Mw/Mn |
|---|---|---|---|---|---|---|---|
| P-10 | (structure) | (structure) | A-66 | | 40/40/20 | 3200 | 1.4 |
| P-11 | (structure) | A-46 | | | 90/10 | 10000 | 1.8 |
| P-12 | (structure) | (structure) | A-22 | | 40/55/5 | 16000 | 2.1 |
| P-13 | (structure) | (structure) | (structure) | A-57 | 30/35/30/5 | 2600 | 1.2 |
| P-14 | (structure) | (structure) | (structure) | A-57 | 40/30/25/5 | 5700 | 1.8 |

TABLE 2-continued

| Resin | Monomer (1) | Monomer (2) | Monomer (3) | Monomer (4) | Compositional Ratio (by mol) | Mw | Mw/Mn |
|---|---|---|---|---|---|---|---|
| P-15 | | | | A-60 | 40/20/35/5 | 6600 | 2.0 |
| P-16 | | | | A-60 | 40/40/10/10 | 3000 | 1.3 |
| P-17 | | | | A-63 | 40/30/28/2 | 4600 | 1.4 |
| P-18 | | | | A-65 | 30/20/48/2 | 2900 | 1.3 |
| P-19 | | | | A-55 | 30/30/30/10 | 2400 | 1.2 |
| P-20 | | | | A-55 | 35/35/29/1 | 5200 | 1.4 |

TABLE 2-continued

| Resin | Monomer (1) | Monomer (2) | Monomer (3) | Monomer (4) | Compositional Ratio (by mol) | Mw | Mw/Mn |
|---|---|---|---|---|---|---|---|
| P-21 | | | | A-56 | 40/20/35/5 | 6300 | 1.3 |
| P-22 | | | | A-96 | 30/25/25/20 | 10900 | 2.3 |
| P-23 | | | | A-75 | 40/20/30/10 | 9900 | 1.5 |
| P-24 | | | | A-116 | 40/10/40/10 | 5000 | 1.4 |
| P-25 | | | | A-116 | 40/20/20/20 | 8500 | 1.6 |

TABLE 2-continued

| Resin | Monomer (1) | Monomer (2) | Monomer (3) | Monomer (4) | Compositional Ratio (by mol) | Mw | Mw/Mn |
|---|---|---|---|---|---|---|---|
| P-26 | (structure) | (structure) | (structure) | A-46 | 40/10/30/20 | 4500 | 1.5 |
| P-27 | (structure) | (structure) | (structure) | A-121 | 50/10/30/10 | 4500 | 1.5 |
| P-28 | (structure) | (structure) | (structure) | A-122 | 50/20/20/10 | 8100 | 1.6 |
| Comparative Examples ||||||||
| R1 | (structure) | (structure) | (structure) | — | 40/30/30 | 8600 | 2.2 |
| R2 | (structure) | (structure) | (structure) | — | 50/20/30 | 6400 | 1.8 |

TABLE 2-continued

| Resin | Monomer (1) | Monomer (2) | Monomer (3) | Monomer (4) | Compositional Ratio (by mol) | Mw | Mw/Mn |
|---|---|---|---|---|---|---|---|
| R3 | (structure) | (structure) | (structure) | — | 50/10/40 | 7000 | 1.9 |

TABLE 3

| Resin | Monomer (1) | Monomer (2) | Monomer (3) | Monomer (4) | Compositional Ratio (by mol) | Mw | Mw/Mn |
|---|---|---|---|---|---|---|---|
| 1 | (structure) | (structure) | (structure) | (structure) | 35/15/35/15 | 10000 | 1.9 |
| 2 | (structure) | (structure) | (structure) | (structure) | 40/5/45/10 | 8900 | 1.9 |
| 3 | (structure) | (structure) | (structure) | | 40/30/30 | 12000 | 1.8 |
| 4 | (structure) | (structure) | (structure) | | 40/20/40 | 8900 | 1.9 |

TABLE 3-continued

| Resin | Monomer (1) | Monomer (2) | Monomer (3) | Monomer (4) | Compositional Ratio (by mol) | Mw | Mw/Mn |
|---|---|---|---|---|---|---|---|
| 5 | (structure) | (structure) | (structure) | | 50/20/30 | 10200 | 2.3 |
| 6 | (structure) | (structure) | (structure) | (structure) | 40/10/40/10 | 8900 | 1.7 |
| 7 | (structure) | (structure) | (structure) | (structure) | 20/20/50/10 | 7800 | 1.7 |
| 8 | (structure) | (structure) | (structure) | (structure) | 40/10/40/10 | 9800 | 1.8 |
| 9 | (structure) | (structure) | (structure) | (structure) | 40/20/30/10 | 9800 | 1.6 |

TABLE 3-continued

| Resin | Monomer (1) | Monomer (2) | Monomer (3) | Monomer (4) | Compositional Ratio (by mol) | Mw | Mw/Mn |
|---|---|---|---|---|---|---|---|
| 10 | | | | | 40/30/30 | 13000 | 1.8 |
| 11 | | | | | 40/30/30 | 3600 | 1.4 |
| 12 | | | | | 40/20/30/10 | 7000 | 1.6 |
| 13 | | | | | 30/35/30/5 | 5500 | 1.9 |
| 14 | | | | | 40/30/30 | 9800 | 2.0 |

TABLE 3-continued

| Resin | Monomer (1) | Monomer (2) | Monomer (3) | Monomer (4) | Compositional Ratio (by mol) | Mw | Mw/Mn |
|---|---|---|---|---|---|---|---|
| 15 | | | | | 40/20/40 | 7700 | 2.1 |
| 16 | | | | | 30/30/40 | 8800 | 2.6 |
| 17 | | | | | 40/30/30 | 9000 | 2.1 |
| 18 | | | | | 30/20/40/10 | 5800 | 2.2 |
| 19 | | | | | 30/30/40 | 9800 | 2.1 |

TABLE 3-continued

| Resin | Monomer (1) | Monomer (2) | Monomer (3) | Monomer (4) | Compositional Ratio (by mol) | Mw | Mw/Mn |
|---|---|---|---|---|---|---|---|
| 20 | | | | | 35/35/30 | 9800 | 2.1 |
| 21 | | | | | 50/20/30 | 5100 | 1.6 |
| 22 | | | | | 30/25/25/20 | 8900 | 1.8 |
| 23 | | | | | 40/20/40 | 7500 | 1.6 |

Examples 1 to 30 and Comparative Examples 1 to 5

Preparation of Resist

The components shown in Table 4-1 below were dissolved in a solvent to prepare a solution having a solid content concentration of 5 mass %, and the obtained solution was filtered through a polyethylene filter having a pore size of 0.1 µm to prepare a photosensitive composition. The photosensitive compositions prepared were evaluated by the following methods, and the results are shown in Table 4-2. As for each component in the Table, the ratio when using a plurality of kinds is a ratio by mass.

Incidentally, in Table 4-1, when the photosensitive composition contained a hydrophobic resin (HR), the mode of addition is denoted by "added", and when the photosensitive composition did not contain a hydrophobic resin (HR) and after the formation of a photosensitive film, a topcoat protective film containing a hydrophobic resin (HR) was formed as an overlayer of the film, the mode of addition is denoted by "TC".

Image Performance Test:
(Exposure Condition (1): Normal Dry Exposure)

An organic antireflection film, ARC29A (produced by Nissan Chemical Industries, Ltd.), was applied on a silicon wafer and baked at 205° C. for 60 seconds to form an antireflection film having a film thickness of 78 nm, and the photosensitive composition prepared was applied thereon and baked at 130° C. for 60 seconds to form a photosensitive film having a film thickness of 120 nm. The obtained wafer was exposed using an ArF excimer laser scanner (PAS5500/1100, manufactured by ASML, NA: 0.75) through a 6% halftone mask having a 65-nm 1:1 line-and-space pattern. Thereafter, the photosensitive film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (2): Normal Immersion Exposure)

An organic antireflection film, ARC29A (produced by Nissan Chemical Industries, Ltd.), was applied on a silicon wafer and baked at 205° C. for 60 seconds to form an antireflection film having a film thickness of 78 nm, and the photosensitive composition prepared was applied thereon and baked at 130° C. for 60 seconds to form a resist film having a film thickness of 120 nm. The obtained wafer was exposed using an ArF excimer laser immersion scanner (PAS5500/1250i, manufactured by ASML, NA: 0.85) through a 6% halftone mask having a 65-nm 1:1 line-and-space pattern. The immersion liquid used was ultrapure water. Thereafter, the photosensitive film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (3): Dry Double Exposure)

An organic antireflection film, ARC29A (produced by Nissan Chemical Industries, Ltd.), was applied on a silicon wafer and baked at 205° C. for 60 seconds to form an antireflection film having a film thickness of 78 nm, and the photosensitive composition prepared was applied thereon and baked at 130° C. for 60 seconds to form a photosensitive film having a film thickness of 120 nm. The obtained wafer was subjected to first exposure by using an ArF excimer laser scanner (PAS5500/1100, manufactured by ASML, NA: 0.75) through a 6% halftone mask having a 60 nm space-and-180 nm line pattern and further to second exposure through the same pattern as in the first mask by displacing the mask by 120 nm such that the space was arranged between a space and a space at the first exposure. Thereafter, the photosensitive film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (4): Immersion Double Exposure)

An organic antireflection film, ARC29A (produced by Nissan Chemical Industries, Ltd.), was applied on a silicon wafer and baked at 205° C. for 60 seconds to form an antireflection film having a film thickness of 78 nm, and the photosensitive composition prepared was applied thereon and baked at 130° C. for 60 seconds to form a photosensitive film having a film thickness of 120 nm. The obtained wafer was subjected to first exposure by using an ArF excimer laser immersion scanner (PAS5500/1250i, manufactured by ASML, NA: 0.85) through a 6% halftone mask having a 50 nm space-and-150 nm line pattern and further to second exposure through the same pattern as in the first mask by displacing the mask by 100 nm such that the space was arranged between a space and a space at the first exposure. The immersion liquid used was ultrapure water. Thereafter, the photosensitive film was heated at 130° C. for 60 seconds, developed with an aqueous tetramethylammonium hydroxide solution (2.38 mass %) for 30 seconds, rinsed with pure water and spin-dried to obtain a resist pattern.

When the addition mode of the hydrophobic resin (HR) is "TC", the following operation was performed after the formation of the photosensitive film.
<Topcoat Forming Method>

The hydrophobic resin (HR) shown in Table 4-1 was dissolved in a solvent and applied by a spin coater on the photosensitive film above, and the wafer was heated at 115° C. for 60 seconds to form a topcoat layer having a film thickness of 0.05 µm. At this time, the topcoat was observed whether coating unevenness was present or not, and it was confirmed that the topcoat was uniformly applied without coating unevenness.

The abbreviations of solvents are as follows.
SL-1: 2-Ethylbutanol
SL-2: Perfluorobutyltetrahydrofuran
Pattern Profile:

The pattern profile was observed through a scanning microscope (S-4800, manufactured by Hitachi, Ltd.).
Line Edge Roughness (LER):

In the measurement of line edge roughness (nm), the line-and-space pattern (1/1) was observed by a critical dimension scanning electron microscope (SEM) and with respect to the range of 5 µm of the longitudinal edge, the distance from the reference line where the edge should be present was measured at 50 points by Critical Dimension SEM (S-8840, manufactured by Hitachi Ltd.) and after determining the standard deviation, 3σ was computed. A smaller value indicates higher performance.

[Pattern Collapse (PC)]

The exposure dose for reproducing a line-and-space 1/1 mask pattern in target dimension was taken as an optimal exposure dose and with respect to a line-and-space 1:1 dense pattern, the line width at which the pattern was resolved without collapse to a finer mask size than that when exposed with the optimal exposure dose was defined as a limiting pattern collapse line width. A smaller value indicates that a finer pattern is resolved without collapse, namely, pattern collapse (PC (nm)) is less liable to occur and the performance is higher.

[Evaluation of Development Defect]

Using a defect inspection apparatus, KLA 2360 (trade name), manufactured by KLA Tencor Ltd., measurement was performed in a random mode by setting the pixel size of the defect inspection apparatus to 0.16 μm and the threshold value to 20 so as to detect development defects extracted from the difference produced by superposing pixel units with a reference image. The number of development defects per unit area (defects/cm$^2$) was computed. The sample was rated A when the value was less than 0.5, rated B when from 0.5 to 0.8, and rated C when more than 0.8. A smaller value indicates higher performance.

TABLE 4-1

| | Resin (A) | (g) | Compound (C) | (g) | Acid Generator (B) | (g) | Resin (A') (10 g) | Basic Compound | (g) |
|---|---|---|---|---|---|---|---|---|---|
| Example | | | | | | | | | |
| 1 | P-1 | (6.0) | II-1 | (1.0) | — | (—) | 1 | PEA | (0.02) |
| 2 | P-2 | (5.0) | II-2 | (2.0) | z60, 38 | (0.1/0.05) | 2 | DCMA | (0.02) |
| 3 | P-3 | (15.0) | II-3 | (1.0) | z63 | (0.1) | 3 | TOA | (0.01) |
| 4 | P-4 | (7.0) | II-4 | (1.0) | z78 | (0.2) | 4 | PBI | (0.02) |
| 5 | P-5 | (11.1) | II-5 | (2.0) | z38 | (0.2) | 5 | PEA/DIA | (0.01/0.005) |
| 6 | P-6 | (4.5) | II-6 | (4.5) | z69 | (0.4) | 6 | TOA | (0.005) |
| 7 | P-7 | (2.0) | II-10 | (0.5) | z66 | (0.2) | 7 | PEA | (0.01) |
| 8 | P-8 | (3.0) | II-11 | (0.6) | z60, 68 | (0.2/0.2) | 8 | PEA/DIA | (0.01/0.01) |
| 9 | P-9 | (3.0) | II-12 | (1.0) | z69 | (0.1) | 9 | PEA | (0.02) |
| 10 | P-10 | (3.0) | II-7 | (2.0) | z66 | (0.2) | 10 | DHA | (0.02) |
| 11 | P-11 | (4.5) | II-8 | (0.6) | z50 | (0.3) | 11 | PEA | (0.02) |
| 12 | P-12 | (5.0) | II-9 | (2.0) | z61 | (0.3) | 12 | TPSA | (0.01) |
| 13 | P-13 | (1.5) | II-22 | (0.3) | z72 | (0.1) | 13 | TMEA | (0.02) |
| 14 | P-14 | (7.0) | II-23 | (0.5) | z38 | (0.2) | 14 | PEA | (0.02) |
| 15 | P-15 | (7.0) | II-19 | (2.0) | z69 | (0.2) | 15 | PEA | (0.02) |
| 16 | P-16 | (2.0) | II-20 | (1.0) | z78 | (0.2) | 16 | PEA/DIA | (0.01/0.005) |
| 17 | P-17 | (3.0) | II-21 | (0.3) | z60, 68 | (0.2/0.2) | 17 | PEA | (0.01) |
| 18 | P-18 | (3.0) | II-13 | (0.3) | z68 | (0.2) | 18 | TPA | (0.01) |
| 19 | P-19 | (2.0) | II-14 | (1.0) | z60 | (0.2) | 19 | TBAH | (0.02) |
| 20 | P-20 | (7.0) | — | (—) | — | (—) | — | TPI | (0.02) |
| 21 | P-21 | (4.5) | II-16 | (2.0) | z70 | (0.2) | 21 | PEA | (0.02) |
| 22 | P-22 | (1.0) | — | (—) | z72 | (0.4) | 22 | PBI | (0.01) |
| 23 | P-23 | (5.5) | — | (—) | — | (—) | 23 | DBN | (0.02) |
| 24 | P-24 | (7.0) | 1-5 | (2.0) | z72 | (0.01) | 6 | TBAH | (0.02) |
| 25 | P-25 | (6.5) | 6-1 | (2.0) | z38 | (0.2) | 7 | TPI | (0.02) |
| 26 | P-26 | (7.0) | 1-5 | (0.3) | z69 | (0.2) | 8 | PEA | (0.02) |
| 27 | P-28 | (8.5) | — | (—) | z69 | (0.2) | 9 | PEA/DIA | (0.01/0.005) |
| 28 | P-1 | (6.0) | 4-1 | (1.0) | — | (—) | 1 | PEA | (0.02) |
| 29 | P-6 | (4.5) | 2-6 | (4.5) | z69 | (0.4) | 6 | TOA | (0.005) |
| 30 | P-11 | (4.5) | 5-4 | (0.6) | z50 | (0.3) | 11 | PEA | (0.02) |
| Comparative Example | | | | | | | | | |
| 1 | — | (—) | — | (—) | z38 | (0.15) | 1 | PEA/DIA | (0.01/0.005) |
| 2 | — | (—) | — | (—) | z60 | (0.4) | 3 | DIA | (0.03) |
| 3 | — | (—) | — | (—) | z38 | (0.2) | 10 | PEA | (0.03) |
| 4 | — | (—) | II-19 | (2.0) | z78 | (0.2) | 22 | TBAH | (0.04) |
| 5 | — | (—) | II-20 | (1.0) | z38 | (0.2) | 20 | PBI | (0.01) |

| | Surfactant (0.03 g) | Solvent | (ratio by mass) | Dissolution Inhibiting Compound (g) | Hydrophobic Resin (HR) | Mode of Addition | (g) or (Solvent) |
|---|---|---|---|---|---|---|---|
| Example | | | | | | | |
| 1 | W-4 | A1/B1 | (80/20) | | HR-80 | added | (0.2) |
| 2 | W-4 | A1 | (100) | | HR-11, 73 | added | (0.1/0.05) |
| 3 | W-6 | A1/B1 | (80/20) | LCB (0.15) | HR-22 | added | (0.1) |
| 4 | W-4 | A1/B1 | (80/20) | | HR-5 | added | (0.2) |
| 5 | W-4 | A1 | (100) | | HR-20 | added | (0.2) |
| 6 | W-2 | A1/B1 | (60/40) | | HR-83 | TC | (SL-2) |
| 7 | W-4 | A1/B1 | (80/20) | | HR-37 | added | (0.4) |
| 8 | W-4 | A1/B1 | (80/20) | | HR-30 | added | (0.3) |
| 9 | W-4 | A1 | (100) | | HR-47 | added | (0.1) |
| 10 | W-4 | A1 | (100) | | HR-51 | added | (0.2) |
| 11 | W-2 | A1/B1 | (80/20) | | HR-66 | added | (0.4) |
| 12 | W-4 | A1/A3 | (60/40) | | HR-44 | added | (0.1) |
| 13 | W-6 | A1/B1 | (80/20) | | HR-63 | added | (0.3) |
| 14 | W-4 | A1/B2 | (60/40) | | HR-15 | added | (0.2) |
| 15 | W-4 | A1/B1 | (80/20) | LCB (0.3) | HR-51 | added | (0.2) |
| 16 | W-6 | A1/B2 | (60/40) | | HR-65 | added | (0.2) |
| 17 | W-4 | A1/B1 | (80/20) | | HR-83 | TC | (SL-2) |
| 18 | W-4 | A1/B1 | (60/40) | | HR-83 | TC | (SL-2) |

TABLE 4-1-continued

|  |  |  |  |  |  |  |  |
|---|---|---|---|---|---|---|---|
| 19 | W-1 | A1 | (100) |  | HR-80 | added | (0.2) |
| 20 | W-4 | A1 | (100) |  | HR-80 | added | (0.2) |
| 21 | W-5 | A1/B1 | (60/40) |  | HR-80 | added | (0.2) |
| 22 | W-4 | A1/B1 | (60/40) |  | HR-11, 73 | added | (0.1/0.05) |
| 23 | W-6 | A1/B3 | (95/5) |  | HR-53 | TC | (SL-1) |
| 24 | W-6 | A1/A3 | (60/40) |  | HR-15 | added | (0.2) |
| 25 | W-4 | A1/B1 | (80/20) |  | HR-66 | added | (0.4) |
| 26 | W-4 | A1/B2 | (60/40) |  | HR-65 | added | (0.2) |
| 27 | W-1 | A1/B1 | (80/20) |  | HR-83 | TC | (SL-2) |
| 28 | W-4 | A1/B1 | (80/20) |  | HR-80 | added | (0.2) |
| 29 | W-2 | A1/B1 | (60/40) |  | HR-83 | TC | (SL-2) |
| 30 | W-2 | A1/B1 | (80/20) |  | HR-66 | added | (0.4) |
| Comparative Example |  |  |  |  |  |  |  |
| 1 | W-4 | A1/B1 | (60/40) |  | HR-22 | added | (0.15) |
| 2 | W-2 | A1/A3 | (60/40) | LCB (0.1) | HR-66 | added | (0.4) |
| 3 | W-4 | A1 | (100) |  | HR-83 | TC | (SL-2) |
| 4 | W-6 | A1/B1 | (80/20) |  | HR-47 | TC | (SL-1) |
| 5 | W-4 | A1 | (100) |  | HR-65 | added | (0.2) |

TABLE 4-2

|  | Exposure Condition (1) | | | | Exposure Condition (2) | | | |
|---|---|---|---|---|---|---|---|---|
|  | Pattern Profile | Pattern Collapse (nm) | LER (nm) | Development Defect | Pattern Profile | Pattern Collapse (nm) | LER (nm) | Development Defect |
| Example |  |  |  |  |  |  |  |  |
| 1 | rectangular | 32.0 | 4.3 | A | rectangular | 20.3 | 5.0 | A |
| 2 | rectangular | 33.2 | 4.6 | A | rectangular | 37.2 | 3.4 | A |
| 3 | rectangular | 34.8 | 5.0 | A | rectangular | 23.6 | 2.7 | A |
| 4 | rectangular | 26.7 | 3.0 | A | rectangular | 24.2 | 4.2 | A |
| 5 | rectangular | 32.4 | 2.6 | A | rectangular | 31.5 | 4.6 | A |
| 6 | rectangular | 30.8 | 2.8 | A | rectangular | 30.0 | 4.1 | A |
| 7 | rectangular | 23.8 | 3.9 | A | rectangular | 17.7 | 3.4 | A |
| 8 | rectangular | 27.6 | 3.0 | A | rectangular | 23.2 | 2.4 | A |
| 9 | rectangular | 24.1 | 3.8 | A | rectangular | 26.0 | 3.1 | A |
| 10 | rectangular | 19.6 | 4.2 | A | rectangular | 23.6 | 3.5 | A |
| 11 | rectangular | 27.4 | 4.6 | A | rectangular | 25.2 | 4.0 | A |
| 12 | rectangular | 19.7 | 3.0 | A | rectangular | 26.7 | 5.4 | A |
| 13 | rectangular | 21.4 | 3.4 | A | rectangular | 34.8 | 4.8 | A |
| 14 | rectangular | 19.3 | 4.8 | A | rectangular | 28.2 | 4.0 | A |
| 15 | rectangular | 19.4 | 4.4 | A | rectangular | 25.6 | 3.4 | A |
| 16 | rectangular | 30.6 | 3.2 | A | rectangular | 31.8 | 3.4 | A |
| 17 | rectangular | 30.4 | 4.9 | A | rectangular | 21.2 | 3.3 | A |
| 18 | rectangular | 22.0 | 5.0 | A | rectangular | 19.1 | 3.7 | A |
| 19 | rectangular | 31.8 | 3.6 | A | rectangular | 28.4 | 3.5 | A |
| 20 | rectangular | 28.0 | 3.6 | A | rectangular | 23.3 | 3.9 | A |
| 21 | rectangular | 29.4 | 5.1 | A | rectangular | 21.8 | 4.8 | A |
| 22 | rectangular | 35.1 | 3.4 | A | rectangular | 25.0 | 3.5 | A |
| 23 | rectangular | 20.3 | 4.2 | A | rectangular | 18.0 | 4.0 | A |
| 24 | rectangular | 30.3 | 4.5 | A | rectangular | 45.0 | 4.5 | A |
| 25 | rectangular | 35.6 | 4.6 | A | rectangular | 33.0 | 5.0 | A |
| 26 | rectangular | 40.6 | 4.3 | A | rectangular | 35.6 | 4.9 | A |
| 27 | rectangular | 50.1 | 4.9 | A | rectangular | 39.9 | 4.6 | A |
| 28 | rectangular | 29.0 | 4.3 | A | rectangular | 36.2 | 4.5 | A |
| 29 | rectangular | 30.6 | 6.2 | A | rectangular | 35.2 | 4.6 | A |
| 30 | rectangular | 30.9 | 5.5 | A | rectangular | 26.2 | 4.9 | A |
| Comparative Example |  |  |  |  |  |  |  |  |
| 1 | tapered | 65.4 | 12.3 | C | tapered | 54.0 | 9.9 | C |
| 2 | tapered | 91.5 | 10.9 | B | tapered | 56.6 | 10.5 | C |
| 3 | tapered | 76.3 | 9.9 | C | tapered | 78.7 | 12.5 | C |
| 4 | tapered | 93.1 | 11.1 | C | reverse tapered | 76.3 | 15.0 | C |
| 5 | reverse tapered | 73.9 | 8.9 | C | reverse tapered | 84.3 | 12.5 | C |

TABLE 4-2-continued

|  | Exposure Condition (3) | | | | Exposure Condition (4) | | | |
| --- | --- | --- | --- | --- | --- | --- | --- | --- |
|  | Pattern Profile | Pattern Collapse (nm) | LER (nm) | Development Defect | Pattern Profile | Pattern Collapse (nm) | LER (nm) | Development Defect |
| Example | | | | | | | | |
| 1 | rectangular | 36.4 | 3.4 | A | rectangular | 20.0 | 5.3 | A |
| 2 | rectangular | 34.8 | 4.6 | A | rectangular | 20.6 | 4.4 | A |
| 3 | rectangular | 26.4 | 4.2 | A | rectangular | 23.0 | 5.0 | A |
| 4 | rectangular | 27.2 | 4.4 | A | rectangular | 28.2 | 2.9 | A |
| 5 | rectangular | 30.8 | 5.2 | A | rectangular | 33.8 | 3.1 | A |
| 6 | rectangular | 26.4 | 4.8 | A | rectangular | 30.9 | 4.0 | A |
| 7 | rectangular | 25.3 | 4.7 | A | rectangular | 28.4 | 2.9 | A |
| 8 | rectangular | 25.8 | 4.3 | A | rectangular | 24.4 | 4.4 | A |
| 9 | rectangular | 22.3 | 5.2 | A | rectangular | 26.4 | 4.0 | A |
| 10 | rectangular | 28.2 | 4.3 | A | rectangular | 28.2 | 5.8 | A |
| 11 | rectangular | 26.0 | 4.2 | A | rectangular | 29.0 | 5.2 | A |
| 12 | rectangular | 24.4 | 5.1 | A | rectangular | 30.6 | 3.2 | A |
| 13 | rectangular | 27.4 | 3.2 | A | rectangular | 27.9 | 3.7 | A |
| 14 | rectangular | 38.0 | 4.6 | A | rectangular | 28.4 | 4.1 | A |
| 15 | rectangular | 35.6 | 3.8 | A | rectangular | 23.2 | 3.4 | A |
| 16 | rectangular | 27.6 | 4.1 | A | rectangular | 30.4 | 3.5 | A |
| 17 | rectangular | 29.6 | 3.8 | A | rectangular | 19.4 | 4.0 | A |
| 18 | rectangular | 31.2 | 4.6 | A | rectangular | 25.0 | 3.5 | A |
| 19 | rectangular | 22.8 | 2.8 | A | rectangular | 22.1 | 3.4 | A |
| 20 | rectangular | 27.0 | 3.2 | A | rectangular | 27.9 | 3.6 | A |
| 21 | rectangular | 28.9 | 3.7 | A | rectangular | 25.6 | 3.9 | A |
| 22 | rectangular | 36.0 | 3.1 | A | rectangular | 28.8 | 3.3 | A |
| 23 | rectangular | 26.8 | 3.2 | A | rectangular | 24.3 | 3.9 | A |
| 24 | rectangular | 39.0 | 3.9 | A | rectangular | 38.9 | 4.5 | A |
| 25 | rectangular | 36.8 | 4.8 | A | rectangular | 40.8 | 5.0 | A |
| 26 | rectangular | 34.5 | 4.5 | A | rectangular | 26.8 | 6.8 | A |
| 27 | rectangular | 40.2 | 4.9 | A | rectangular | 39.9 | 6.5 | A |
| 28 | rectangular | 39.6 | 4.4 | A | rectangular | 25.1 | 6.3 | A |
| 29 | rectangular | 32.1 | 5.2 | A | rectangular | 35.0 | 6.6 | A |
| 30 | rectangular | 39.0 | 4.8 | A | rectangular | 40.0 | 6.8 | A |
| Comparative Example | | | | | | | | |
| 1 | reverse tapered | 75.1 | 10.9 | C | tapered | 71.8 | 12.3 | C |
| 2 | reverse tapered | 73.3 | 10.4 | C | tapered | 79.7 | 10.4 | C |
| 3 | tapered | 73.9 | 12.6 | C | tapered | 76.3 | 13.3 | C |
| 4 | tapered | 76.3 | 11.6 | C | tapered | 66.1 | 9.3 | C |
| 5 | reverse tapered | 66.1 | 8.9 | C | reverse tapered | 93.1 | 11.5 | C |

The denotations in the Table are as follows.
[Basic Compound]
TPI: 2,4,5-Triphenylimidazole
TPSA: Triphenylsulfonium acetate
DIA: 2,6-Diisopropylaniline
DCMA: Dicyclohexylmethylamine
TPA: Tripentylamine
TBAH: Tetrabutylammonium hydroxide
TMEA: Tris(methoxyethoxyethyl)amine
PEA: N-Phenyldiethanolamine
TOA: Trioctylamine
DBN: 1,5-Diazabicyclo[4.3.0]non-5-ene
PBI: 2-Phenyl benzimidazole
DHA: N,N-Dihexylaniline
[Surfactant]
W-1: Megaface F176 (produced by Dainippon Ink & Chemicals, Inc.) (fluorine-containing)
W-2: Megaface R08 (produced by Dainippon Ink & Chemicals, Inc.) (fluorine- and silicon-containing)
W-4: Troysol S-366 (produced by Troy Chemical)
W-5: PF656 (produced by OMNOVA, fluorine-containing)
W-6: PF6320 (produced by OMNOVA, fluorine-containing)
[Solvent]
A1: Propylene glycol monomethyl ether acetate
A3: Cyclohexanone
B1: Propylene glycol monomethyl ether
B2: Ethyl lactate
B3: Propylene carbonate
[Dissolution Inhibiting Compound]
LCB: tert-Butyl lithocholate As apparent from the results in Table 4-2, the photosensitive composition of the present invention exhibits good performance in terms of pattern profile and LER not only in normal exposure (dry exposure) but also in immersion exposure and at the same time, exhibits good performance in terms of pattern profile and LER also in double exposure.

INDUSTRIAL APPLICABILITY

According to the present invention, a photosensitive composition ensuring good performance in terms of pattern profile and line edge roughness and reduction of pattern collapse and development defect not only in normal exposure (dry exposure) but also in immersion exposure, a pattern forming method using the photosensitive composition, and a compound for use in the photosensitive composition can be provided. Also, a photosensitive composition suitable for double exposure, ensuring good performance in terms of pattern profile and line edge roughness and reduction of pattern collapse and development defect in double exposure, a pattern forming method using the photosensitive composition, and a compound for use in the photosensitive composition can be provided.

While the invention has been described in detail and with reference to specific embodiments thereof, it will be apparent to one skilled in the art that various changes and modifications can be made therein without departing from the spirit and scope of the present invention.

This application is based on Japanese Patent Application (Japanese Patent Application No. 2007-245332) filed on Sep. 21, 2007 and Japanese Patent Application (Japanese Patent Application No. 2008-009840) filed on Jan. 18, 2008, the contents of which are incorporated herein by way of reference.

The invention claimed is:

1. A photosensitive composition, comprising:
   (A) a resin containing a repeating unit derived from a compound represented by the following formula (I), the compound of formula (I) being an acrylic acid derivative, a methacrylic acid derivative or a styrene derivative, and the resin being capable of producing an acid group upon irradiation with an actinic ray or radiation:

Z-A-X-B-R    (I)

wherein Z represents a group capable of becoming an acid group resulting from leaving of a cation upon irradiation with an actinic ray or radiation;
   A represents an alkylene group;
   X represents —SO$_2$— or —SO—;
   B represents a single bond, an oxygen atom or —N(Rx)-;
   Rx represents a hydrogen atom or a monovalent organic group;
   R represents a monovalent organic group substituted by Y;
   when B represents —N(Rx)-, R and Rx may combine with each other to form a ring; and
   Y is a group having a structure having one addition polymerizable unsaturated bond, the structure being selected from the group consisting of an acrylic acid ester, a methacrylic acid ester and a vinyl structure.

2. The photosensitive composition according to claim 1, wherein B in formula (I) represents an oxygen atom or —N(Rx)-.

3. The photosensitive composition according to claim 1, wherein A in formula (I) contains a fluorine atom.

4. The photosensitive composition according to claim 1, wherein Z in formula (I) represents a salt of an organic acid group selected from the group consisting of a sulfonic acid group, an imide acid group and a methide acid group.

5. The photosensitive composition according to claim 1, wherein Y in formula (I) is selected from the group consisting of structures each having one addition-polymerizable unsaturated bond which are selected from the group consisting of an acrylic acid ester and a methacrylic acid ester.

6. The photosensitive composition according to claim 1, wherein the compound represented by formula (I) is a sulfonium salt compound or an iodonium salt compound.

7. The photosensitive composition according to claim 1, which further comprises:
   a hydrophobic resin (HR).

8. The photosensitive composition according to claim 1, which further comprises:
   (C) a compound capable of decomposing by an action of an acid to generate an acid.

9. A pattern forming method, comprising:
   forming a photosensitive film from the photosensitive composition according to claim 1; and
   exposing and developing the photosensitive film.

10. The pattern forming method according to claim 9, further comprising:
    forming a topcoat as an overlayer of the photosensitive film before subjecting the photosensitive film to the exposure and development,
    wherein the exposure is immersion exposure.

11. The pattern forming method according to claim 9, wherein the exposure is immersion exposure.

12. A photosensitive composition, comprising:
    (A) a resin containing a repeating unit derived from a compound represented by the following formula (I), the resin being capable of producing an acid group upon irradiation with an actinic ray or radiation:

Z-A-X-B-R    (I)

wherein Z represents a group capable of becoming an acid group resulting from leaving of a cation upon irradiation with an actinic ray or radiation which is a salt of an organic acid group selected from the group consisting of an imide acid group and a methide acid group;
    A represents an alkylene group which contains a fluorine atom;
    X represents a single bond or a heteroatom-containing divalent linking group;
    B represents a single bond, an oxygen atom or —N(Rx)-;
    Rx represents a hydrogen atom or a monovalent organic group;
    R represents a monovalent organic group substituted by Y;
    when B represents —N(Rx)-, R and Rx may combine with each other to form a ring; and
    Y is a group having a radical polymerizable unsaturated bond.

13. The photosensitive composition according to claim 12, wherein X in formula (I) represents a linking group selected from the group consisting of a single bond, —SO$_2$—, —SO— and —CO—.

* * * * *